US012778809B2

(12) United States Patent
Seddon et al.

(10) Patent No.: US 12,778,809 B2
(45) Date of Patent: Nov. 3, 2026

(54) MULTIPLE FLUID PATHWAY CONNECTOR WITH FOAM SUPPORTS

(71) Applicant: KCI Licensing, Inc., San Antonio, TX (US)

(72) Inventors: James Killingworth Seddon, Wimborne (GB); Christopher Brian Locke, Bournemouth (GB); Timothy Mark Robinson, Shillingstone (GB); Benjamin Andrew Pratt, Poole (GB); Colin John Hall, Poole (GB); Justin Rice, Denver, CO (US)

(73) Assignee: KCI Licensing Inc., San Antonio, TX (US)

( * ) Notice: Subject to any disclaimer, the term of this patent is extended or adjusted under 35 U.S.C. 154(b) by 698 days.

(21) Appl. No.: 17/792,649

(22) PCT Filed: Jan. 27, 2021

(86) PCT No.: PCT/IB2021/050620
§ 371 (c)(1),
(2) Date: Jul. 13, 2022

(87) PCT Pub. No.: WO2021/152473
PCT Pub. Date: Aug. 5, 2021

(65) Prior Publication Data

US 2023/0338194 A1 Oct. 26, 2023

Related U.S. Application Data

(60) Provisional application No. 62/967,160, filed on Jan. 29, 2020.

(51) Int. Cl.
*A61F 13/05* (2024.01)
*A61F 13/00* (2024.01)
(Continued)

(52) U.S. Cl.
CPC ........ *A61F 13/05* (2024.01); *A61F 13/00987* (2013.01); *A61F 13/01021* (2024.01); *A61L 15/425* (2013.01)

(58) Field of Classification Search
CPC ........ A61M 1/00; A61M 27/00; A61M 39/05; B32B 7/10; A61F 13/00; A61F 13/02; A61F 13/05; A61F 1/85; A61F 1/92
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |

(Continued)

FOREIGN PATENT DOCUMENTS

| | | | |
|---|---|---|---|
| AU | 550575 | B2 | 3/1986 |
| CA | 2005436 | A1 | 6/1990 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Michele Kidwell

(57) ABSTRACT

Disclosed embodiments relate to devices and systems for providing negative-pressure therapy, instillation, and/or pressure-sensing at a tissue site, and to methods of manufacturing such devices and systems. In some embodiments, a fluid bridge may comprise a first layer of foam with a plurality of supports extending from at least an inner surface, and a second layer. The first and second layers may be coupled together around the perimeter to form one or more enclosed fluid pathways, for example extending from a port
(Continued)

to an aperture. In some embodiments, at least the first layer may be formed of closed-cell foam.

19 Claims, 27 Drawing Sheets

(51) Int. Cl.
*A61F 13/01* (2024.01)
*A61L 15/42* (2006.01)

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,198,801 B2 12/2015 Weston
9,211,365 B2 12/2015 Weston
9,289,542 B2 3/2016 Blott et al.
12,239,779 B2 * 3/2025 Pratt ........................ A61M 1/96
2002/0077661 A1 6/2002 Saadat
2002/0115951 A1 8/2002 Norstrem et al.
2002/0120185 A1 8/2002 Johnson
2002/0143286 A1 10/2002 Tumey
2009/0254054 A1 * 10/2009 Blott ........................ A61M 1/85 604/317
2014/0163491 A1 6/2014 Schuessler et al.
2015/0080788 A1 3/2015 Blott et al.
2015/0196431 A1 * 7/2015 Dunn .................... A61M 1/916 604/319
2016/0158067 A1 * 6/2016 Heaton ............. A61F 13/01025 29/592
2016/0199550 A1 * 7/2016 Seddon ................... A61M 1/92 604/319
2019/0343687 A1 11/2019 Locke et al.

FOREIGN PATENT DOCUMENTS

CA 2476953 * 11/2003 ............... C08K 3/22
DE 26 40 413 A1 3/1978
DE 43 06 478 A1 9/1994
EP 0100148 A1 2/1984
EP 0117632 A2 9/1984
EP 0161865 A2 11/1985

(56) References Cited

FOREIGN PATENT DOCUMENTS

| | | | | | |
|---|---|---|---|---|---|
| EP | 0358302 | A2 | 3/1990 | | |
| GB | 692578 | A | 6/1953 | | |
| GB | 2195255 | A | 4/1988 | | |
| GB | 2 197 789 | A | 6/1988 | | |
| GB | 2 220 357 | A | 1/1990 | | |
| GB | 2 235 877 | A | 3/1991 | | |
| GB | 2 329 127 | A | 3/1999 | | |
| GB | 2 333 965 | A | 8/1999 | | |
| WO | 80/02182 | A1 | 10/1980 | | |
| WO | 87/04626 | A1 | 8/1987 | | |
| WO | 90/010424 | A1 | 9/1990 | | |
| WO | 93/009727 | A1 | 5/1993 | | |
| WO | 94/20041 | A1 | 9/1994 | | |
| WO | 96/05873 | A1 | 2/1996 | | |
| WO | 97/18007 | A1 | 5/1997 | | |
| WO | 99/13793 | A1 | 3/1999 | | |
| WO | 1018967 | A1 | 7/2000 | | |
| WO | 2017/087163 | * | 5/2017 | ............. | A61F 13/00 |
| WO | 2017/205556 | * | 11/2017 | ............. | A61F 13/00 |
| WO | 2019/084006 | A1 | 5/2019 | | |
| WO | 2020/055945 | * | 3/2020 | ............. | A61F 13/00 |

OTHER PUBLICATIONS

Chariker, Mark E., M.D., et al; "Effective Management of incisional and cutaneous fistulae with closed suction wound drainage"; Contemporary Surgery, vol. 34, Jun. 1989, pp. 59-63.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A.C.® Therapy Clinical Guidelines: A Reference Source for Clinicians; Jul. 2007.

International Search Report and Written Opinion Corresponding to Application No. PCT/IB2021/050620, mailed Mar. 16, 2021.

* cited by examiner

MULTIPLE FLUID PATHWAY CONNECTOR WITH FOAM SUPPORTS

CROSS-REFERENCE TO RELATED APPLICATIONS

This application claims the benefit of priority to U.S. Provisional Application No. 62/967,160, filed on Jan. 29, 2020, which is incorporated herein by reference in its entirety.

TECHNICAL FIELD

The invention set forth in the appended claims relates generally to tissue treatment systems and more particularly, but without limitation, to low-profile distribution components for providing negative-pressure therapy and/or instillation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound or a cavity can be washed out with a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter. Some embodiments are illustrative of an apparatus or system for delivering both negative pressure and instillation to a tissue site, which can be used in conjunction with low-profile distribution components.

For example, in some embodiments, a low-profile bridge or dressing interface may be configured to allow application of negative pressure and instillation fluid alternately, through separate pathways. Some embodiments may also comprise a separate pressure-sensing pathway. In some embodiments, the bridge may comprise two or more stacked layers coupled about a perimeter to form an enclosed space that may form one or more fluid pathways. In some embodiments, at least the first layer may be formed of foam, such as closed-cell foam. In some embodiments, the second layer may be formed of a polymeric film or of closed-cell foam. Some embodiments may further comprise a third stacked layer, which may form another fluid pathway. In some embodiments, the third layer may be formed of polymeric film or of closed-cell foam. The bridge may include a port, for example in a proximal end, and an aperture, for example in a distal end, and the one or more fluid pathways may extend and provide fluid communication between the port and the aperture. In some embodiments, one or more barriers between the first and second layers may form a plurality of side-by-side adjacent fluid pathways, which may be pneumatically isolated except at their distal ends. For example, a single bridge may include two separate pathways formed by the barrier: a negative-pressure pathway and an instillation pathway. In some embodiments, a slot may extend between the side-by-side adjacent pathways, which may allow folding of the bridge and/or improved flexibility. At least the negative-pressure pathway may include open pathway features, configured to maintain an open pathway in the negative-pressure pathway. For example, the open pathway features may be thermoformed closed-cell foam structures, which may include a plurality of foam supports configured to prevent collapse of the negative-pressure pathway in some embodiments. In some embodiments, the instillation pathway and the negative-pressure pathway may be in fluid communication through their distal ends.

More generally, some apparatus embodiments may relate to managing fluid at a tissue site, and may comprise: a first layer comprising an outer surface, an inner surface, and a first plurality of supports extending from the inner surface, wherein the first layer is formed of foam; a second layer in stacked relationship with the first layer and oriented to be adjacent to the first plurality of supports, wherein the first layer and the second layer define at least one fluid pathway therebetween; an aperture configured to provide fluid communication between the at least one fluid pathway and the tissue site; and a port configured to provide fluid communication between the at least one fluid pathway and a negative-pressure source. In some embodiments, the first layer may be formed of closed-cell foam. In some embodiments, the first layer and the second layer may be coupled around a perimeter. In some embodiments, each of the first plurality of supports may have a height, and the height may be substantially the same for all of the first plurality of supports. In some embodiments, the first layer or the second layer may comprise a perimeter wall having a height equal to the height of the first plurality of supports.

In some embodiments, the second layer may comprise or consist essentially of a film. In other embodiments, the second layer may comprise or consist essentially of foam, for example being formed of closed-cell foam. The second layer may be a substantially flat sheet, in some embodiments. In other embodiments, the second layer may comprise an inner surface, an outer surface, and a second plurality of supports extending from the inner surface. In some embodiments, the first plurality of supports may be aligned with and in stacked relationship with the second plurality of supports. Some embodiments may further comprise a first barrier between the inner surface of the first layer and an inner surface of the second layer, wherein the at least one fluid pathway comprises a first fluid pathway and a second fluid pathway formed by the first barrier. In some embodiments, the first fluid pathway may be configured to be in fluid communication with a negative-pressure source through the port; the second fluid pathway may be configured to be in fluid communication with an instillation source or a pressure sensor through the port; and the first fluid pathway and the second fluid pathway may be pneumatically isolated except through a recessed space configured to provide fluid communication between the aperture, the first fluid pathway, and the second fluid pathway. Some embodiments may further comprise a second barrier between the inner surface of the first layer and the inner surface of the second layer, wherein: the at least one fluid pathway may further comprise a third fluid pathway formed by the second barrier; the third fluid pathway may be pneumatically isolated except through the recessed space; and the third fluid pathway may be configured to be in fluid communication with a pressure sensor through the port.

In some embodiments, the first plurality of supports and/or second plurality of supports may be configured to support the first fluid pathway to resist collapse under negative pressure (e.g. during negative-pressure therapy, with negative pressure applied by the negative-pressure source). In some embodiments, the first plurality of supports may be coupled to the second layer. In some embodiments, the first plurality of supports may be coupled to the second plurality of supports. Some embodiments may further comprise an affixation surface located on the outer surface around the aperture. In some embodiments, the first layer may further comprise a slot between and separating the first fluid pathway and the second fluid pathway. Some embodiments may further comprise a third layer in stacked relationship with the first layer and the second layer in order to form an additional fluid pathway extending between the port and the recessed space, wherein the additional fluid pathway is pneumatically isolated except at the recessed space. The third layer may be coupled to either the first layer or the second layer around the perimeter. In some embodiments, the third layer may comprise or consist essentially of a film. In other embodiments, the third layer may comprise or consist essentially of foam, such as closed-cell foam. In some embodiments, the at least one fluid pathway may be coated with an anticoagulant agent and/or with a hydrophobic surface treatment. In some embodiments, one or more of the at least one fluid pathway may comprise a valve. Some embodiments may further comprise a bulb element configured to collapse, for example to be substantially flat with the outer surface, when experiencing negative pressure (e.g. from the negative-pressure source), and to project outward in the absence of negative pressure.

Some embodiments may relate to an apparatus for managing fluid at a tissue site, and the apparatus may comprise: a first layer comprising an outer surface, an inner surface, and a first plurality of supports extending from the inner surface, wherein the first layer is formed of closed-cell foam; a second layer of closed-cell foam in stacked relationship with the first layer and oriented to be adjacent to the first plurality of supports, wherein the first layer and the second layer are coupled around a perimeter to define at least one fluid pathway; an aperture configured to provide fluid communication between the at least one fluid pathway and the tissue site; and a port configured to provide fluid communication between the at least one pathway and a negative-pressure source; wherein the second layer is a substantially flat sheet.

Some embodiments may relate to an apparatus for managing fluid at a tissue site, and the apparatus may comprise: a first layer comprising an outer surface, an inner surface, and a first plurality of supports extending from the inner surface, wherein the first layer is formed of closed-cell foam; a second layer in stacked relationship with the first layer and oriented to be adjacent to the first plurality of supports, a third layer in stacked relationship with the first layer and the second layer, wherein the first layer and the second layer are coupled around a perimeter to define at least one fluid pathway, and the third layer is coupled to either the first layer or the second layer around the perimeter to define an additional fluid pathway; an aperture configured to provide fluid communication between the at least one fluid pathway, the additional fluid pathway, and the tissue site; and a port configured to provide fluid communication between the at least one pathway and a negative-pressure source. In some embodiments, the port may further be configured to provide fluid communication between the additional fluid pathway and an instillation source or a pressure sensor. In some embodiments, the third layer may comprise or consist essentially of a polymer film. In other embodiments, the third layer may comprise or consist essentially of closed-cell foam.

Systems for managing fluid at a tissue site is also described herein, wherein some example embodiments may include a negative-pressure source; and a bridge fluidly coupled to the negative-pressure source. In some embodiments, the bridge may comprise an apparatus similar to the embodiments described above. For example, the bridge may comprise: a spacer layer comprising an outer surface, an inner surface, and a plurality of supports extending from the inner surface, wherein the spacer layer is formed of foam; a cover layer in stacked relationship with the spacer layer and oriented to be adjacent to the plurality of supports, wherein the spacer layer and the cover layer define at least one fluid pathway therebetween; an aperture configured to provide fluid communication between the at least one fluid pathway and the tissue site; and a port configured to provide fluid communication between the at least one fluid pathway and the negative-pressure source. Some embodiments may further comprise an instillation source, wherein the at least one fluid pathway comprises a negative-pressure pathway in fluid communication with the negative-pressure source and an instillation pathway in fluid communication with the instillation source. Some embodiments may further comprising a pressure sensor, wherein the at least one fluid pathway comprises a negative-pressure pathway in fluid communication with the negative-pressure source and a sensing pathway in fluid communication with the pressure sensor.

Methods for manufacturing fluid bridges are also described herein, wherein some example embodiments may include: forming a first layer of foam, such as closed-cell foam, having a plurality of supports extending outward from a first surface; stacking a second layer with the first layer, wherein the plurality of supports contact the second layer; and coupling the first layer and the second layer around a perimeter to form an enclosed space therebetween. In some embodiments, the second layer may comprise or consist essentially of either foam, such as closed-cell foam, or a polymeric film. In some embodiments, the second layer may be substantially a flat sheet, and all of the supports may be formed entirely in the first layer. Some embodiments may further comprise forming an aperture in a distal end of the bridge, and forming a port in a proximal end of the bridge. In some embodiments, the port may be in fluid communication with the aperture. Some embodiments may further comprise forming a barrier between the first layer and the second layer, wherein: the barrier is configured to divide the enclosed space into two fluid pathways extending from the port to the aperture; and the two fluid pathways are pneumatically isolated except at the aperture. Some embodiments may further comprise forming two barriers between the first layer and the second layer, wherein: the two barriers are configured to divide the enclosed space into three independent fluid pathways extending from the port to the aperture; and the three independent fluid pathways are pneumatically isolated except at the distal end. In some embodiments, forming the first layer may comprise: providing a sheet of foam; and creating the plurality of supports, perimeter walls, and/or the one or more barriers in the first surface by one of the following: thermoforming, compression molding, vacuum forming, embossing, and combinations thereof. In some embodiments, the supports, perimeters walls, and/or one or more barriers may be simultaneously formed, for example from a single sheet of foam. In some embodiments, the first layer may comprise or consist essentially of closed-cell foam. Some embodiments may further comprise forming the perimeter walls between the first layer and second layer, wherein the perimeter walls and the plurality of supports have an identical height. In some embodiments, coupling the first layer and the second layer may comprise sealingly coupling the first layer and the second layer at the perimeter walls. Some embodiments may further comprise coupling the supports to the second layer.

Some embodiments may further comprise providing a third layer, stacking the third layer with the first layer and the second layer, and coupling the third layer to either the first layer or the second layer around the perimeter to form another pathway. When the third layer is stacked atop the second layer, the method may further comprise the step of forming an opening, which may be configured to provide fluid communication between a third pathway (e.g. formed between the third layer and the second layer) and the aperture, in the distal end of the second layer. In some embodiments, the third layer may comprise or consist essentially of either foam, such as closed-cell foam, or a polymeric film.

In some embodiments, the first layer may be a double-sided spacer layer, and the method may further comprise the step of forming the first layer to also have a plurality of supports extending from a second surface. Some method embodiments may further comprise the step of forming one or more openings, which may be configured to provide fluid communication with the aperture, in the distal end of the double-sided spacer layer. In some embodiments, the second layer may be a separator layer, and forming the separator layer may comprise forming (e.g. by welds) channel walls (which may define a channel between the walls) and an opening in the distal end of the channel Some embodiments may further comprise providing an upper layer and a lower layer, stacking the layers (e.g. with the lower layer beneath the double-sided spacer layer, the separator layer above the double-sided spacer layer, and the upper layer above the separator layer), and/or coupling the upper and lower layers. In some embodiments, providing the lower layer may comprise forming the aperture in the distal end of the lower layer. The upper layer may be stacked and coupled to the channel walls of the separator layer, to enclose the channel (which may be configured to serve as the instillation pathway). The openings in the double-sided spacer layer may be configured to provide fluid communication between the aperture and the opening in the channel, and to provide fluid communication between the aperture and the enclosed area around the channel (e.g. between the double-sided spacer layer and the separator layer). In some embodiments, the upper layer and the lower layer may comprise or consist essentially of a polymeric film. In some embodiments, the separator layer may comprise a polymeric film, which may be selected to allow coupling (e.g. welding) to the foam of the double-sided spacer layer. In some embodiments, the upper layer and/or the lower layer may comprise perimeter walls (e.g. a raised lip around the perimeter), configured to allow the upper layer and the lower layer to enclose the double-sided spacer layer and the separator layer.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but it may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
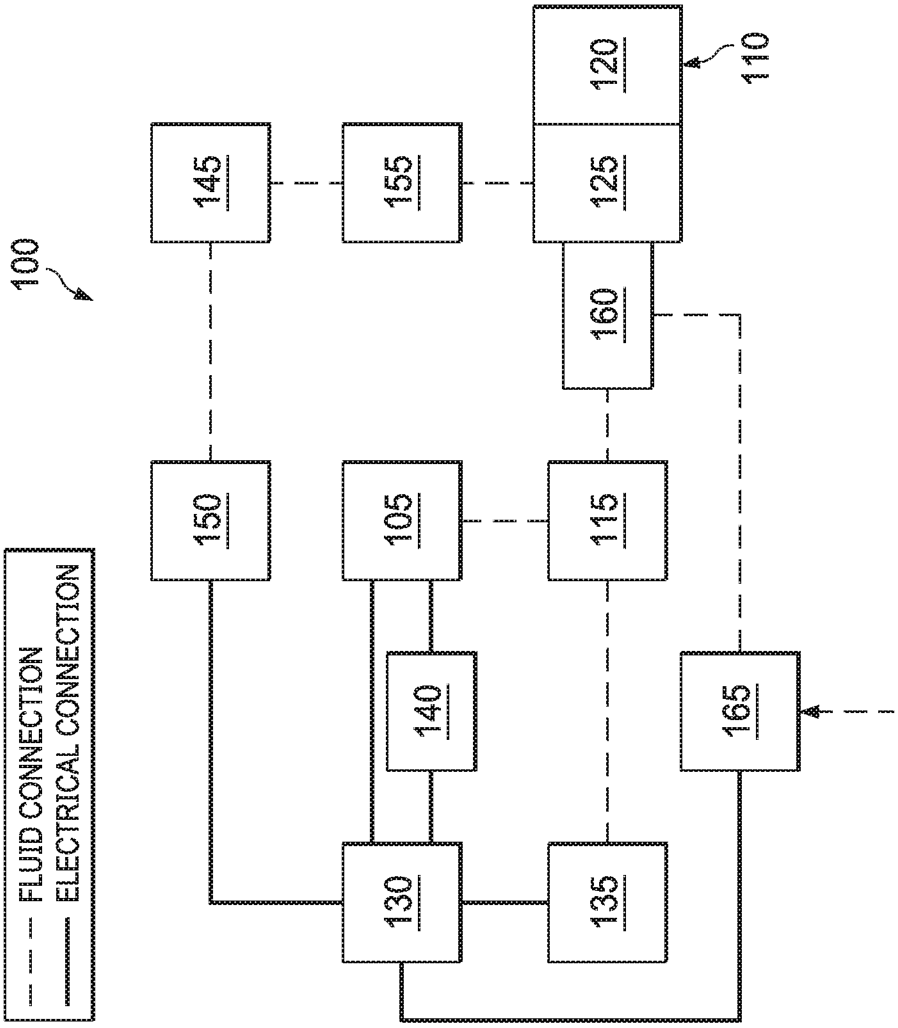
FIG. 1 is a functional block diagram of an example embodiment of a therapy system that can provide negative-pressure treatment and instillation treatment in accordance with this specification.

FIG. 1 is a simplified functional block diagram of an example embodiment of a therapy system 100 that can provide negative-pressure therapy with instillation of topical treatment solutions to a tissue site in accordance with this specification.

The term "tissue site" in this context broadly refers to a wound, defect, or other treatment target located on or within tissue, including, but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a source or supply of negative pressure, such as a negative-pressure source 105, and one or more distribution components. A distribution component is preferably detachable and may be disposable, reusable, or recyclable. A dressing, such as a dressing 110, and a fluid container, such as a container 115, are examples of distribution components that may be associated with some examples of the therapy system 100. As illustrated in the example of FIG. 1, the dressing 110 may comprise or consist essentially of a tissue interface 120, a cover 125, or both in some embodiments.

A fluid conductor is another illustrative example of a distribution component. A "fluid conductor," in this context, broadly includes a tube, pipe, hose, conduit, or other structure with one or more lumina or open pathways adapted to convey a fluid between two ends. A tube, for example, is generally an elongated, flexible structure with a cylindrical lumen, but the geometry and rigidity may vary. Moreover, some fluid conductors may be molded into or otherwise integrally combined with other components. Distribution components may also include or comprise interfaces or fluid ports to facilitate coupling and de-coupling other components. In some embodiments, for example, a dressing interface may facilitate coupling a fluid conductor to the dressing 110. For example, such a dressing interface may be a SENSAT.R.A.C.™ Pad, available from Kinetic Concepts, Inc. of San Antonio, Texas.

The therapy system 100 may also include a regulator or controller, such as a controller 130. Additionally, the therapy system 100 may include sensors to measure operating parameters and provide feedback signals to the controller 130 indicative of the operating parameters. As illustrated in FIG. 1, for example, the therapy system 100 may include a first sensor 135 and a second sensor 140 coupled to the controller 130.

The therapy system 100 may also include a source of instillation solution. For example, a solution source 145 may be fluidly coupled to the dressing 110, as illustrated in the example embodiment of FIG. 1. The solution source 145 may be fluidly coupled to a positive-pressure source, such as a positive-pressure source 150, a negative-pressure source, such as the negative-pressure source 105, or both in some embodiments. A regulator, such as an instillation regulator 155, may also be fluidly coupled to the solution source 145 and the dressing 110 to ensure proper dosage of instillation solution (e.g. saline) to a tissue site. For example, the instillation regulator 155 may comprise a piston that can be pneumatically actuated by the negative-pressure source 105 to draw instillation solution from the solution source during a negative-pressure interval and to instill the solution to a dressing during a venting interval. Additionally or alternatively, the controller 130 may be coupled to the negative-pressure source 105, the positive-pressure source 150, or both, to control dosage of instillation solution to a tissue site. In some embodiments, the instillation regulator 155 may also be fluidly coupled to the negative-pressure source 105 through the dressing 110, as illustrated in the example of FIG. 1.

In some examples, a bridge 160 may fluidly couple the dressing 110 to the negative-pressure source 105, as illustrated in FIG. 1. In some embodiments, the bridge 160 may serve as the dressing interface. The therapy system 100 may also comprise a flow regulator, such as a regulator 165, fluidly coupled to a source of ambient air to provide a controlled or managed flow of ambient air. In some embodiments, the regulator 165 may be fluidly coupled to the tissue interface 120 through the bridge 160. In some embodiments, the regulator 165 may be positioned proximate to the container 115 and/or proximate a source of ambient air, where the regulator 165 is less likely to be blocked during usage.

Some components of the therapy system 100 may be housed within or used in conjunction with other components, such as sensors, processing units, alarm indicators, memory, databases, software, display devices, or user interfaces that further facilitate therapy. For example, in some embodiments, the negative-pressure source 105 may be combined with the controller 130, the solution source 145, and other components into a therapy unit.

In general, components of the therapy system 100 may be coupled directly or indirectly. For example, the negative-pressure source 105 may be directly coupled to the container 115 and may be indirectly coupled to the dressing 110 through the container 115. Coupling may include fluid, mechanical, thermal, electrical, or chemical coupling (such as a chemical bond), or some combination of coupling in some contexts. For example, the negative-pressure source 105 may be electrically coupled to the controller 130 and may be fluidly coupled to one or more distribution components to provide a fluid path to a tissue site. In some embodiments, components may also be coupled by virtue of physical proximity, being integral to a single structure, or being formed from the same piece of material.

A negative-pressure supply, such as the negative-pressure source 105, may be a reservoir of air at a negative pressure or may be a manual or electrically-powered device, such as a vacuum pump, a suction pump, a wall suction port available at many healthcare facilities, or a micro-pump, for example. "Negative pressure" generally refers to a pressure less than a local ambient pressure, such as the ambient pressure in a local environment external to a sealed therapeutic environment. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. References to increases in negative pressure typically refer to a decrease in absolute pressure, while decreases in negative pressure typically refer to an increase in absolute pressure. While the amount and nature of negative pressure provided by the negative-pressure source 105 may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

The container 115 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

A controller, such as the controller 130, may be a microprocessor or computer programmed to operate one or more components of the therapy system 100, such as the negative-pressure source 105. In some embodiments, for example, the controller 130 may be a microcontroller, which generally comprises an integrated circuit containing a processor core and a memory programmed to directly or indirectly control one or more operating parameters of the therapy system 100. Operating parameters may include the power applied to the negative-pressure source 105, the pressure generated by the negative-pressure source 105, or the pressure distributed to the tissue interface 120, for example. The controller 130 is also preferably configured to receive one or more input signals, such as a feedback signal, and programmed to modify one or more operating parameters based on the input signals.

Sensors, such as the first sensor 135 and the second sensor 140, are generally known in the art as any apparatus operable to detect or measure a physical phenomenon or property, and generally provide a signal indicative of the phenomenon or property that is detected or measured. For example, the first sensor 135 and the second sensor 140 may be configured to measure one or more operating parameters of the therapy system 100. In some embodiments, the first sensor 135 may be a transducer configured to measure pressure in a pneumatic pathway and convert the measurement to a signal indicative of the pressure measured. In some embodiments, for example, the first sensor 135 may be a piezo-resistive strain gauge. The second sensor 140 may optionally measure operating parameters of the negative-pressure source 105, such as a voltage or current, in some embodiments. Preferably, the signals from the first sensor 135 and the second sensor 140 are suitable as an input signal to the controller 130, but some signal conditioning may be appropriate in some embodiments. For example, the signal may need to be filtered or amplified before it can be processed by the controller 130. Typically, the signal is an electrical signal, but may be represented in other forms, such as an optical signal.

The tissue interface 120 can be generally adapted to partially or fully contact a tissue site. The tissue interface 120 may take many forms, and may have many sizes, shapes, or thicknesses, depending on a variety of factors, such as the type of treatment being implemented or the nature and size of a tissue site. For example, the size and shape of the tissue interface 120 may be adapted to the contours of deep and irregular shaped tissue sites. Any or all of the surfaces of the tissue interface 120 may have an uneven, coarse, or jagged profile.

In some embodiments, the tissue interface 120 may comprise or consist essentially of a manifold. A manifold in this context may comprise or consist essentially of a means for collecting or distributing fluid across the tissue interface 120 under pressure. For example, a manifold may be adapted to receive negative pressure from a source and distribute negative pressure through multiple apertures across the tissue interface 120, which may have the effect of collecting fluid from across a tissue site and drawing the fluid toward the source. In some embodiments, the fluid path may be reversed or a secondary fluid path may be provided to facilitate delivering fluid, such as fluid from a source of instillation solution, across a tissue site.

In some illustrative embodiments, a manifold may comprise a plurality of pathways, which can be interconnected to improve distribution or collection of fluids. In some illustrative embodiments, a manifold may comprise or consist essentially of a porous material having interconnected fluid pathways. Examples of suitable porous material that can be adapted to form interconnected fluid pathways (e.g., channels) may include cellular foam, including open-cell foam such as reticulated foam; porous tissue collections; and other porous material such as gauze or felted mat that generally include pores, edges, and/or walls. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the tissue interface 120 may comprise or consist essentially of reticulated foam having pore sizes and free volume that may vary according to needs of a prescribed therapy. For example, reticulated foam having a free volume of at least 90% may be suitable for many therapy applications, and foam having an average pore size in a range of 400-600 microns (40-50 pores per inch) may be particularly suitable for some types of therapy. The tensile strength of the tissue interface 120 may also vary according to needs of a prescribed therapy. For example, the tensile strength of foam may be increased for instillation of topical treatment solutions. The 25% compression load deflection of the tissue interface 120 may be at least 0.35 pounds per square inch, and the 65% compression load deflection may be at least 0.43 pounds per square inch. In some embodiments, the tensile strength of the tissue interface 120 may be at least 10 pounds per square inch. The tissue interface 120 may have a tear strength of at least 2.5 pounds per inch. In some embodiments, the tissue interface may be foam comprised of polyols, such as polyester or polyether, isocyanate, such as toluene diisocyanate, and polymerization modifiers, such as amines and tin compounds. In some examples, the tissue interface 120 may be reticulated polyurethane foam such as found in GRANUFOAM™ dressing or V.A.C. VERAFLO™ dressing, both available from Kinetic Concepts, Inc. of San Antonio, Texas.

The thickness of the tissue interface 120 may also vary according to needs of a prescribed therapy. For example, the thickness of the tissue interface may be decreased to reduce tension on peripheral tissue. The thickness of the tissue interface 120 can also affect the conformability of the tissue interface 120. In some embodiments, a thickness in a range of about 5 millimeters to 10 millimeters may be suitable.

The tissue interface 120 may be either hydrophobic or hydrophilic. In an example in which the tissue interface 120 may be hydrophilic, the tissue interface 120 may also wick fluid away from a tissue site, while continuing to distribute negative pressure to the tissue site. The wicking properties of the tissue interface 120 may draw fluid away from a tissue site by capillary flow or other wicking mechanisms. An example of a hydrophilic material that may be suitable is a polyvinyl alcohol, open-cell foam such as V.A.C. WHITEFOAM™ dressing available from Kinetic Concepts, Inc. of San Antonio, Texas. Other hydrophilic foams may include those made from polyether. Other foams that may exhibit hydrophilic characteristics include hydrophobic foams that have been treated or coated to provide hydrophilicity.

In some embodiments, the tissue interface 120 may be constructed from bioresorbable materials. Suitable bioresorbable materials may include, without limitation, a polymeric blend of polylactic acid (PLA) and polyglycolic acid (PGA). The polymeric blend may also include, without limitation, polycarbonates, polyfumarates, and capralactones. The tissue interface 120 may further serve as a scaffold for new cell-growth, or a scaffold material may be used in conjunction with the tissue interface 120 to promote cell growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 125 may provide a bacterial barrier and protection from physical trauma. The cover 125 may also be constructed from a material that can reduce evaporative losses and provide a fluid seal between two components or two environments, such as between a therapeutic environment and a local external environment. The cover 125 may comprise or consist of, for example, an elastomeric film or membrane that can provide a seal adequate to maintain a negative pressure at a tissue site for a given negative-pressure source. The cover 125 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide effective breathability and mechanical properties.

In some example embodiments, the cover 125 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained. The cover 125 may comprise, for example, one or more of the following materials: polyurethane (PU), such as hydrophilic polyurethane; cellulosics; hydrophilic polyamides; polyvinyl alcohol; polyvinyl pyrrolidone; hydrophilic acrylics; silicones, such as hydrophilic silicone elastomers; natural rubbers; polyisoprene; styrene butadiene rubber; chloroprene rubber; polybutadiene; nitrile rubber; butyl rubber; ethylene propylene rubber; ethylene propylene diene monomer; chlorosulfonated polyethylene; polysulfide rubber; ethylene vinyl acetate (EVA); co-polyester; and polyether block polymide copolymers. Such materials are commercially available as, for example, Tegaderm® drape, commercially available from 3M Company, Minneapolis Minnesota; polyurethane (PU) drape, commercially available from Avery Dennison Corporation, Pasadena, California; polyether block polyamide copolymer (PEBAX), for example, from Arkema S.A., Colombes, France; and Inspire 2301 and Inpsire 2327 polyurethane films, commercially available from Expopack Advanced Coatings, Wrexham, United Kingdom. In some embodiments, the cover 125 may comprise INSPIRE 2301 having an MVTR (upright cup technique) of 2600 $g/m^2/24$ hours and a thickness of about 30 microns.

An attachment device may be used to attach the cover 125 to an attachment surface, such as undamaged epidermis, a gasket, or another cover. The attachment device may take many forms. For example, an attachment device may be a medically-acceptable, pressure-sensitive adhesive configured to bond the cover 125 to epidermis around a tissue site. In some embodiments, for example, some or all of the cover 125 may be coated with an adhesive, such as an acrylic adhesive, which may have a coating weight of about 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The solution source 145 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 120 may be placed within, over, on, or otherwise proximate to a tissue site. If the tissue site is a wound, for example, the tissue interface 120 may partially or completely fill the wound, or it may be placed over the wound. The cover 125 may be placed over the tissue interface 120 and sealed to an attachment surface near a tissue site. For example, the cover 125 may be sealed to undamaged epidermis peripheral to a tissue site. Thus, the dressing 110 can provide a sealed therapeutic environment proximate to a tissue site, substantially isolated from the external environment, and the negative-pressure source 105 can reduce pressure in the sealed therapeutic environment. In some embodiments, the regulator 165 may control the flow of ambient air to purge fluids and exudates from the sealed therapeutic environment.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudate and other fluid flow toward lower pressure along a fluid path. Thus, the term "downstream"

typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications, such as by substituting a positive-pressure source for a negative-pressure source, and this descriptive convention should not be construed as a limiting convention.

Negative pressure applied across the tissue site through the tissue interface 120 in the sealed therapeutic environment can induce macro-strain and micro-strain in the tissue site. Negative pressure can also remove exudate and other fluid from a tissue site, which can be collected in container 115.

In some embodiments, the controller 130 may receive and process data from one or more sensors, such as the first sensor 135. The controller 130 may also control the operation of one or more components of the therapy system 100 to manage the pressure delivered to the tissue interface 120. In some embodiments, controller 130 may include an input for receiving a desired target pressure and may be programmed for processing data relating to the setting and inputting of the target pressure to be applied to the tissue interface 120. In some example embodiments, the target pressure may be a fixed pressure value set by an operator as the target negative pressure desired for therapy at a tissue site and then provided as input to the controller 130. The target pressure may vary from tissue site to tissue site based on the type of tissue forming a tissue site, the type of injury or wound (if any), the medical condition of the patient, and the preference of the attending physician. After selecting a desired target pressure, the controller 130 can operate the negative-pressure source 105 in one or more control modes based on the target pressure and may receive feedback from one or more sensors to maintain the target pressure at the tissue interface 120.

In some embodiments, the controller 130 may have a continuous pressure mode, in which the negative-pressure source 105 is operated to provide a constant target negative pressure for the duration of treatment or until manually deactivated. Additionally or alternatively, the controller may have an intermittent pressure mode. For example, the controller 130 can operate the negative-pressure source 105 to cycle between a target pressure and atmospheric pressure. In some examples, the target pressure may be set at a value of 135 mmHg for a specified period of time (e.g., 5 min), followed by a specified period of time (e.g., 2 min) of deactivation. The cycle can be repeated by activating the negative-pressure source 105, which can form a square wave pattern between the target pressure and atmospheric pressure.

In some example embodiments, the increase in negative pressure from ambient pressure to the target pressure may not be instantaneous. For example, the negative-pressure source 105 and the dressing 110 may have an initial rise time, which can vary depending on the type of dressing and therapy equipment being used. For example, the initial rise time for one therapy system may be in a range of about 20-30 mmHg/second and in a range of about 5-10 mmHg/second for another therapy system. If the therapy system 100 is operating in an intermittent mode, the repeating rise time may be a value substantially equal to the initial rise time.

In other examples, a target pressure can vary with time in a dynamic pressure mode. For example, the target pressure may vary in the form of a triangular waveform, varying between a negative pressure of 50 and 135 mmHg with a rise time set at a rate of +25 mmHg/min. and a descent time set at −25 mmHg/min. In other embodiments of the therapy system 100, the triangular waveform may vary between negative pressure of 25 and 135 mmHg with a rise time set at a rate of +30 mmHg/min and a descent time set at −30 mmHg/min.

In some embodiments, the controller 130 may control or determine a variable target pressure in a dynamic pressure mode, and the variable target pressure may vary between a maximum and minimum pressure value that may be set as an input prescribed by an operator as the range of desired negative pressure. The variable target pressure may also be processed and controlled by the controller 130, which can vary the target pressure according to a predetermined waveform, such as a triangular waveform, a sine waveform, or a saw-tooth waveform. In some embodiments, the waveform may be set by an operator as the predetermined or time-varying negative pressure desired for therapy.

Figure 2:
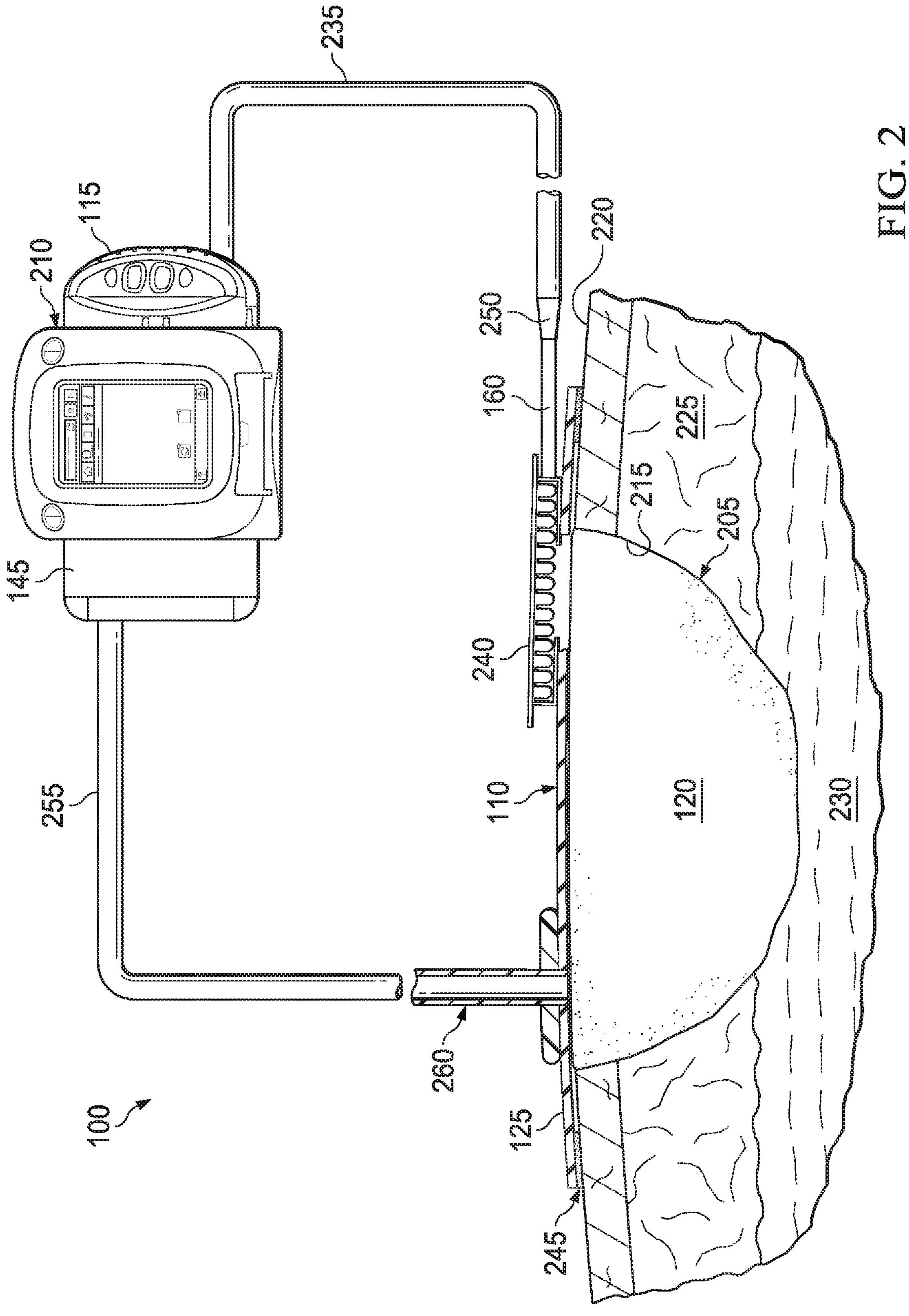
FIG. 2 is a schematic diagram of an example embodiment of the therapy system of FIG. 1 configured to apply negative pressure and treatment solutions to a tissue site.

FIG. 2 is a schematic diagram of an example embodiment of the therapy system 100 configured to apply negative pressure and treatment solutions to a tissue site 205. Some components of the therapy system 100 may be housed within or used in conjunction with other components, such as processing units, alarm indicators, memory, databases, software, display devices, or user interfaces that further facilitate therapy. For example, in some embodiments, the negative-pressure source 105 may be combined with the controller 130 and other components into a therapy unit, such as a therapy unit 210 illustrated in FIG. 2. The therapy unit 210 may be, for example, a V.A.C.ULTA™ Therapy Unit available from Kinetic Concepts, Inc. of San Antonio, Texas.

In the example of FIG. 2, the tissue site 205 is at least partially defined by a wound edge 215, which extends through an epidermal layer 220 and a dermal layer 225 and reaches into a hypodermis, or subcutaneous tissue 230. The therapy system 100 may be used to treat a wound of any depth, as well as many different types of wounds, including open wounds, incisions, or other tissue sites. Treatment of the tissue site 205 may include removal of fluids originating from the tissue site 205, such as exudates or ascites, or fluids instilled into the dressing to cleanse or treat the tissue site 205, such as antimicrobial solutions.

In the example of FIG. 2, a conduit 235 fluidly couples the container 115 to another fluid conductor, such as the bridge 160, which provides a fluid pathway between the conduit 235 and the tissue interface 120. The bridge 160 in the example of FIG. 2 is a substantially flat and flexible fluid conductor, but can also be compressed without occluding or blocking the fluid pathway between the conduit 235 and the tissue interface 120. In some embodiments, the bridge 160 may comprise or be coupled to an applicator 240 adapted to be positioned in fluid communication with the tissue interface 120 through an aperture in the cover 125. The cover 125 may be sealed to the epidermal layer 220 with an attachment device, such as an adhesive layer 245.

In some embodiments, the applicator 240 may be integral to the bridge 160. In other embodiments, the applicator 240 and the bridge 160 may be separate components that are coupled together to form a single device. In yet other embodiments, the applicator 240 and the bridge 160 may be separate components that may be used independently of each other in the therapy system 100.

The bridge 160 may have a substantially flat profile, and an adapter 250 may be configured to fluidly couple the bridge 160 to a tube or other round fluid conductor, such as the conduit 235 illustrated in the example of FIG. 2. In some embodiments, the adapter 250 may have one or more sealing valves, which can isolate the conduit 235 if separated from the bridge 160.

The example of FIG. 2 also illustrates a configuration of the therapy system 100 in which the solution source 145 is fluidly coupled to the tissue interface 120 through a conduit 255 and a dressing interface 260.

Figure 3A:
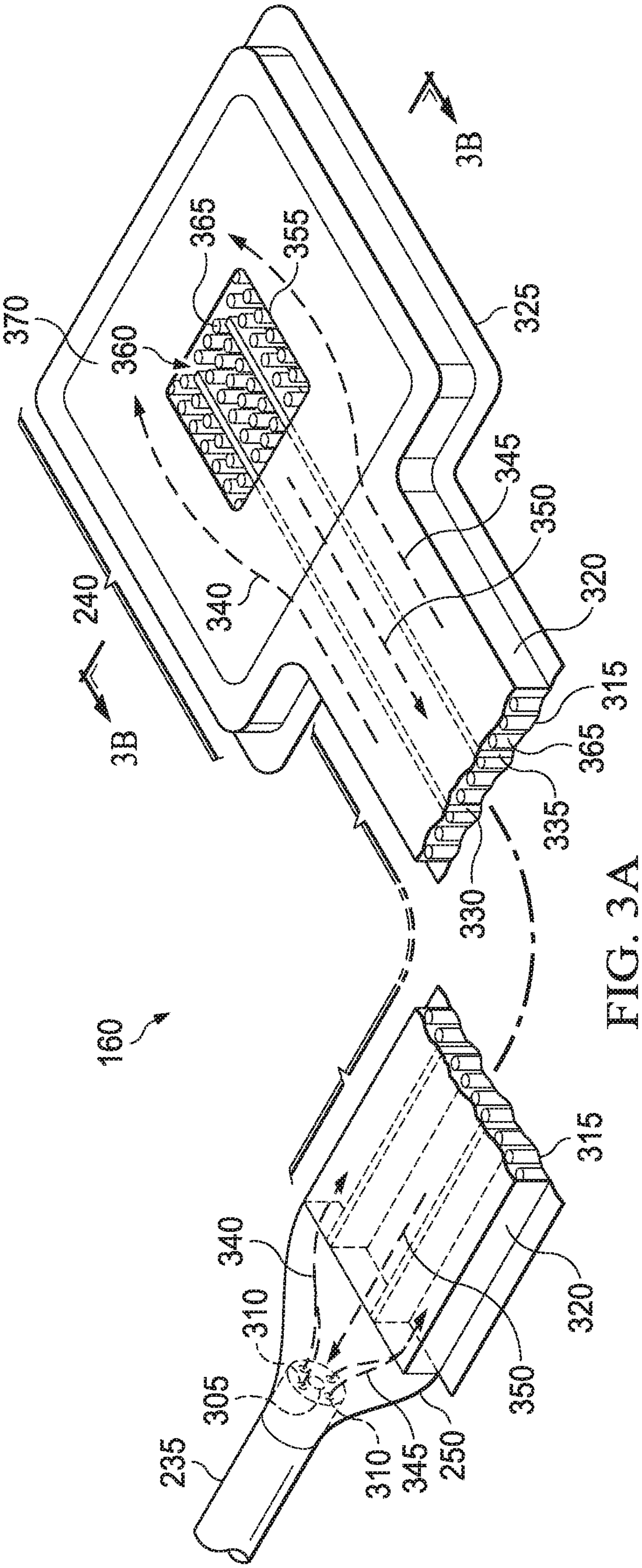
FIG. 3A is a segmented perspective bottom view of an example of a bridge that may be associated with some embodiments of the therapy system of FIG. 1.

FIG. 3A is a segmented perspective bottom view of an example of the bridge 160, illustrating additional details that may be associated with some embodiments. The bridge 160 of FIG. 3A generally has a low profile structure. FIG. 3A further illustrates features that may be associated with some embodiments of the applicator 240 of FIG. 2. The applicator 240 may be bulbous or any shape suitable for facilitating a connection to the dressing 110. The bridge 160 in the example of FIG. 3A is generally long and narrow. An adapter, such as the adapter 250, may fluidly couple the bridge 160 to a fluid conductor, such as the conduit 235. In some examples, the conduit 235 may be a multi-lumen tube in which a central lumen 305 is configured to couple the bridge 160 to a negative-pressure source, and one or more peripheral lumens 310 are configured to couple the bridge 160 to a sensor, such as the first sensor 135.

In some embodiments, the bridge 160 may comprise a liquid barrier formed from two layers. In FIG. 3A, for example, a periphery of a first layer 315 may be coupled to a second layer 320 to form a fluid path between two ends of the bridge 160, including the applicator 240. The first layer 315 and the second layer 320 may both be formed from or include a polymeric film of liquid-impermeable material. In some examples, the first layer 315, the second layer 320, or both may be formed from the same material as the cover 125. The first layer 315 and the second layer 320 may be coupled around the periphery of the bridge 160 to form the sealed space by welding (RF or ultrasonic), heat sealing, or adhesive bonding, such as acrylics or cured adhesives. For example, the first layer 315 and the second layer 320 may be welded together around the periphery of the bridge 160 and may form a flange 325 around the periphery of the bridge 160 as a result of the weld.

The bridge 160 of FIG. 3A may further comprise at least one barrier or wall, such as a first wall 330, between the first layer 315 and the second layer 320. In some embodiments, the first wall 330 may extend from the end of the bridge 160 adjacent to the adapter 250 into the applicator 240 to form at least two sealed spaces or fluid pathways between the first layer 315 and the second layer 320 within the bridge 160. In some examples, the bridge 160 may further comprise a second barrier, such as a second wall 335, between the first layer 315 and the second layer 320. In some embodiments, the second wall 335 also may extend from the end of the bridge 160 adjacent to the adapter 250 into the applicator 240. In some example embodiments, the first wall 330 and the second wall 335 may comprise a polymeric film coupled to the first layer 315 and the second layer 320. In some other example embodiments, the first wall 330 and the second wall 335 may comprise a weld (RF or ultrasonic), a heat seal, an adhesive bond, or a combination of any of the foregoing. In some embodiments, the first wall 330 and the second wall 335 may form distinct fluid pathways within the sealed space between the first layer 315 and the second layer 320. In FIG. 3A, for example, the first wall 330 and the second wall 335 define in part a first pathway 340, a second pathway 345, and a third pathway 350. Each of the first pathway 340, the second pathway 345, and the third pathway 350 generally has a first end, a second end, and a longitudinal axis. In some embodiments, one or more of the fluid pathways may be fluidly coupled or configured to be fluidly coupled to the peripheral lumens 310, which can provide a pressure feedback path to a sensor, such as the first sensor 135. The third pathway 350 may be fluidly coupled to or configured to be fluidly coupled to the central lumen 305.

In some example embodiments, the first pathway 340, the second pathway 345, and the third pathway 350 may be fluidly coupled to the conduit 235 through the adapter 250. For example, the third pathway 350 may be fluidly coupled to the conduit 235 so that the third pathway 350 can deliver negative pressure to the tissue interface 120. Each of the first pathway 340 and the second pathway 345 may be fluidly coupled to a separate one of the peripheral lumens 310. In other embodiments, the first pathway 340 and the second pathway 345 both may be fluidly coupled to a common space within the adapter 250, which can be fluidly coupled to one or more of the peripheral lumens 310. In some example embodiments, the first pathway 340, the second pathway 345, and the third pathway 350 may terminate within the applicator 240. In some embodiments, the first pathway 340, the second pathway 345, and the third pathway 350 may be in fluid communication with each other within the applicator 240 for delivering and sensing negative pressure associated with the tissue interface 120.

The bridge 160 may comprise an opening or aperture, such as an aperture 355, adapted to fluidly couple the sealed space of the bridge 160 to the tissue interface 120. In FIG. 3A, for example, the aperture 355 is disposed in the applicator 240. A recessed space 360 within the bridge 160 can be adapted to be in fluid communication with the tissue interface 120 through the aperture 355 in use. In the example of FIG. 3A, the portions of first layer 315 and the second layer 320 at least partially define the recessed space 360 within the sealed space of the applicator 240. In some example embodiments, the first wall 330 and the second wall 335 may extend only partially into the recessed space 360 so that the ends of the first wall 330 and the second wall 335 are exposed by the aperture 355 as shown in the example of FIG. 3A. In some embodiments, the first pathway 340 and the second pathway 345 may be in fluid communication with the recessed space 360. The third pathway 350 may also be in fluid communication with the recessed space 360 and can be adapted to deliver negative pressure to the tissue interface 120 through the recessed space 360. In some example embodiments (not shown), the first wall 330 and the second wall 335 may extend beyond the aperture 355 so that less of the first pathway 340 and the second pathway 345 are exposed to negative pressure delivered to the tissue interface 120 to prevent or reduce occlusions and/or blockages.

The bridge 160 may further comprise a means for supporting fluid paths under pressure. In some embodiments, the means of support may comprise a plurality of support features, such as a flexible projections, standoffs, nodes, cells, porous textile, porous foam, or some combination of features disposed in a fluid path. For example, the bridge 160 of FIG. 3A comprises a plurality of supports 365. Adjacent to the aperture 355, the supports 365 may be adapted to come in direct contact with the tissue interface 120 in some examples. Support features such as the supports 365 can provide a cushion to prevent the sealed spaces of the bridge 160 from collapsing as a result of external forces. In some example embodiments, the supports 365 may come in contact with the second layer 320, and in some other example embodiments, the top portion of the supports 365 may be coupled to the second layer 320. In some example embodiments, the supports 365 may be disposed only in the applicator 240, and other support features may be disposed in the bridge 160 between the applicator 240 and the conduit 235.

The bridge 160 of FIG. 3A may also comprise an affixation surface 370 surrounding the aperture 355, which can be coupled to the dressing 110 or directly to a tissue site in some examples. In some embodiments, a top drape (not shown) may be utilized to cover the applicator 240 for additional protection and support over the applicator 240 if applied to a tissue site. In some embodiments, a top drape may also be utilized to cover any adhesive that might be exposed. In some embodiments, a top drape may be similar to the cover 125. For example, a top drape may comprise or consist essentially of a polymer, such as a polyurethane film.

Figure 3B:
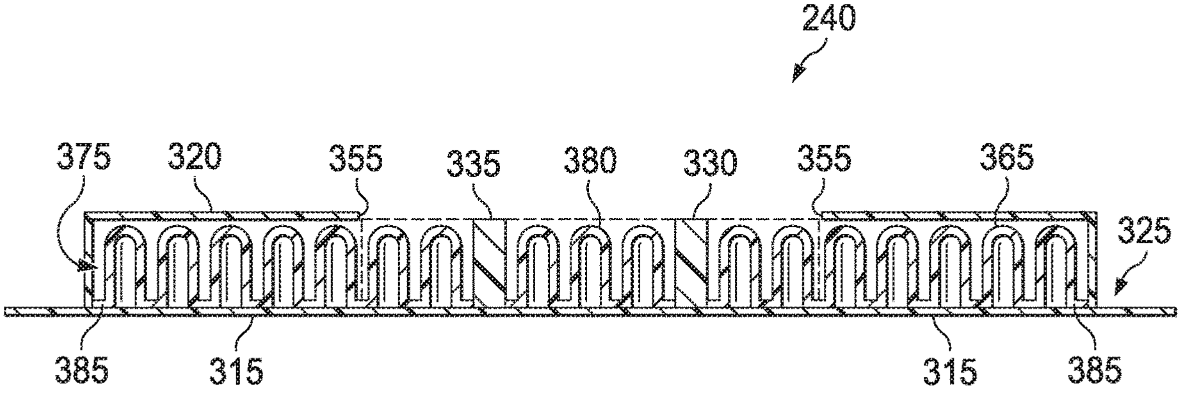
FIG. 3B is a schematic view of an applicator that may be associated with some embodiments of the bridge of FIG. 3A.

FIG. 3B is a schematic view of the applicator 240 of FIG. 3A, taken along line 3B-3B, illustrating additional details that may be associated with some embodiments. For example, some embodiments of the support features may be formed by sealing a spacer layer 375 to the first layer 315. In the example of FIG. 3B, each of the supports 365 comprises a standoff 380 in the spacer layer 375. In some embodiments, the standoffs 380 may be formed by blisters, bubbles, cells or other raised formations that extend above or below a base 385 of the spacer layer 375, for example. In some examples, the standoffs 380 may be vacuum-formed regions of the spacer layer 375.

The base 385 may be sealed to the first layer 315, and the standoffs 380 may extend from the first layer 315 toward the aperture 355 of the second layer 320 as illustrated in FIG. 3B. At least some of the supports 365 may be configured to come in direct contact with the tissue interface 120 through the aperture 355.

In some embodiments, the base 385 may be sealed to the first layer 315 so that the first layer 315 closes the standoffs 380. For example, the base 385 may be heat-sealed to the first layer 315 while the standoffs 380 may be vacuum-formed simultaneously. In other examples, the seal may be formed by adhesion between the first layer 315 and the spacer layer 375. Alternatively, the first layer 315 and the spacer layer 375 may be adhesively bonded to each other.

In general, the supports 365 are structured so that they do not completely collapse from apposition forces resulting from the application of negative pressure and/or external forces to the bridge 160. In some examples, the first layer 315 and the spacer layer 375 may be formed from separate sheets or film brought into superposition and sealed, or they may be formed by folding a single sheet onto itself with a heat-sealable surface facing inward. Any one or more of the first layer 315, second layer 320, and the spacer layer 375 also may be a monolayer or multilayer structure, depending on the application or the desired structure of the support features.

In some example embodiments, the standoffs 380 may be substantially airtight to inhibit collapsing of the standoffs 380 under negative pressure, which could block the flow of fluid through the bridge 160. For example, in the embodiment of FIG. 3B, the standoffs 380 may be substantially airtight and have an internal pressure that is an ambient pressure. In another example embodiment, the standoffs 380 may be inflated with air or other suitable gases, such as carbon dioxide or nitrogen. The standoffs 380 may be inflated to have an internal pressure greater than the atmospheric pressure to maintain their shape and resistance to collapsing under pressure and external forces. For example, the standoffs 380 may be inflated to a pressure up to about 25 psi above the atmospheric pressure.

In some embodiments, the first layer 315, the second layer 320, and the spacer layer 375 may each have a thickness within a range of 400 to 600 microns. For example, the first layer 315, the second layer 320, and the spacer layer 375 may be formed from thermoplastic polyurethane film having a thickness of about 500 microns. In some example embodiments, each may have a thickness of about 200 μm to about 600 μm. In some embodiments, a thickness of about 500 μm or about 250 μm may be suitable.

In some embodiments, one or more of the first layer 315, the second layer 320, and the spacer layer 375 may have a different thickness. For example, the thickness of the second layer 320 may be up to 50% thinner than the thickness of the spacer layer 375. If the fabrication process comprises injection molding, portions of the spacer layer 375 defining the standoffs 380 may have a thickness between about 400 μm and about 500 μm. However, if the standoffs 380 are fabricated by drawing a film, the spacer layer 375 proximate a top portion of the standoffs 380 may have a thickness as thin as 50 μm.

After the standoffs 380 have been fabricated, the walls of the standoffs 380 may have a thickness relative to the thickness of base 385. The relative thickness may be defined by a draw ratio, such as the ratio of the average height of the standoffs 380 to the average thickness of the spacer layer 375. In some example embodiments, the standoffs 380 may have a generally tubular shape, which may have been formed from the spacer layer 375 having various thicknesses and draw ratios. In some example embodiments, the spacer layer 375 may have an average thickness of 500 μm and the standoffs 380 may have an average height in a range between about 2.0 mm and 5.0 mm. Consequently, the standoffs 380 may have a draw ratio ranging from about 4:1 to about 10:1 for heights of 2.0 and 5.0 mm, respectively. In another example embodiment, the draw ratio may range from about 5:1 to about 13:1 where the thickness of the spacer layer 375 is an average of about 400 μm. In yet other example embodiments, the draw ratio may range from about 3:1 to about 9:1 where the thickness of the spacer layer 375 is an average of about 600 μm. In some embodiments, the standoffs 380 may have an average height in a range between about 1.0 mm and 4.0 mm, depending on the thickness of the spacer layer 375. The spacer layer 375 may have varying thicknesses and flexibilities, but is substantially non-stretchable so that the standoffs 380 maintain a generally constant volume if sealed to the first layer 315. Additionally, the standoffs 380 can support a load without bursting and can recover their original shape after a load is removed.

In some example embodiments, any one or more of the first layer 315, the second layer 320, and the spacer layer 375 may be formed from a non-porous, polymeric film that may comprise any flexible material that can be manipulated to form suitable support features, including various thermoplastic materials, e.g., polyethylene homopolymer or copolymer, polypropylene homopolymer or copolymer, etc. Non-limiting examples of suitable thermoplastic polymers may include polyethylene homopolymers, such as low density polyethylene (LDPE) and high density polyethylene (HDPE), and polyethylene copolymers such as, e.g., ionomers, EVA, EMA, heterogeneous (Zeigler-Natta catalyzed) ethylene/alpha-olefin copolymers, and homogeneous (metallocene, single-cite catalyzed) ethylene/alpha-olefin copolymers. Ethylene/alpha-olefin copolymers are copolymers of ethylene with one or more comonomers selected from $C_3$ to $C_{20}$ alpha-olefins, such as 1-butene, 1-pentene, 1-hexene, 1-octene, methyl pentene and the like, in which the polymer molecules comprise long chains with relatively few side chain branches, including linear low density polyethylene (LLDPE), linear medium density polyethylene (LMDPE), very low density polyethylene (VLDPE), and ultra-low density polyethylene (ULDPE). Various other materials may also be suitable, such as polypropylene homopolymer or polypropylene copolymer (e.g., propylene/ethylene copolymer), polyesters, polystyrenes, polyamides, polycarbonates, etc.

In some embodiments, the polymeric film may possess sufficient tensile strength to resist stretching under apposition forces created by negative-pressure therapy. The tensile strength of a material is the ability of material to resist stretching as represented by a stress-strain curve where stress is the force per unit area, i.e., pascals (Pa), newtons per square meter ($N/m^2$), or pounds per square inch (psi). The ultimate tensile strength (UTS) is the maximum stress the material can withstand while being stretched before failing or breaking. Many materials display a linear elastic behavior defined by a linear stress-strain relationship often extending up to a nonlinear region represented by the yield point, i.e., the yield strength of a material. For example, high density polyethylene (HDPE) has a high tensile strength and low-density polyethylene (LDPE) has a slightly lower tensile strength, which are suitable materials for the sheets of non-porous, polymeric film as set forth above. Linear low density polyethylene (LLDPE) may also be suitable for some examples because the material stretches very little as the force is increased up to the yield point of the material. Thus, the standoffs 380 or other support features can be configured to resist collapsing (or stretching) when subjected to an external force or pressure. For example, HDPE has a UTS of about 37 MPa and may have a yield strength that ranges from about 26-33 MPa depending on the thickness of the material, while LDPE has somewhat lower values.

In some example embodiments, one or more of the first layer 315, the second layer 320, and the spacer layer 375 may comprise or consist essentially of a thermoplastic polyurethane (TPU) film that is permeable to water vapor but impermeable to liquid. The film may be in various degrees breathable and may have MVTRs that are proportional to their thickness. For example, the MVTR may be at least 300 $g/m^2$ per twenty-four hours in some embodiments. For permeable materials, the permeability generally should be low enough to maintain a desired negative pressure for the desired negative-pressure treatment.

In some example embodiments, the thermoplastic polyurethane film may be, for example, a Platilon® thermoplastic polyurethane film available from Convestro LLC, which may have a UTS of about 60 MPa and may have a yield strength of approximately 11 MPa or greater than about 10 MPa depending on the thickness of the material. Therefore, in some example embodiments, it is desirable that the non-porous, polymeric film may have a yield strength greater than about 10 MPa, depending on the type and thickness of material. A material having a lower yield strength may be too stretchable and, therefore, more susceptible to breaking with the application of small amounts of compression and/or apposition forces.

Figure 3C:
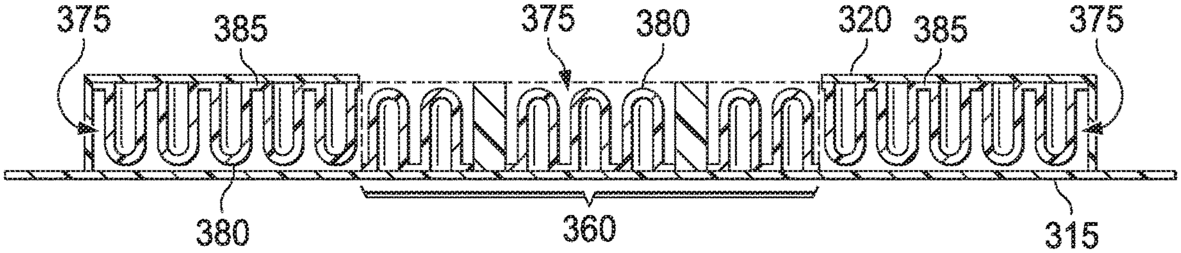
FIG. 3C is a schematic view of another example of an applicator that may be associated with some embodiments of the bridge of FIG. 3A.

FIG. 3C is a schematic view of another example of the applicator 240, illustrating details that may be associated with some embodiments. In the example of FIG. 3C, the applicator 240 has more than one spacer layer 375. At least some of the support features may be formed by sealing the base 385 of at least one of the spacer layers 375 to the second layer 320. Some of the supports 365 may extend from the second layer 320 toward the first layer 315 around the recessed space 360. In the example of FIG. 3C, all of the supports 365 around the recessed space 360 extend from the second layer 320 toward the first layer 315. At least some of the supports 365 may also extend from the first layer 315 toward the aperture 355 in the recessed space 360.

Figure 3D:
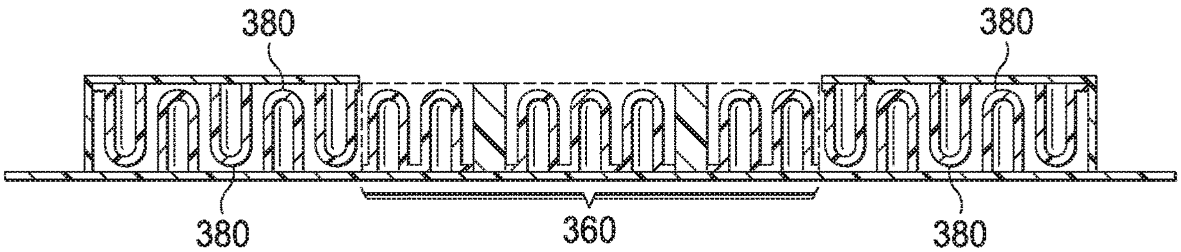
FIG. 3D is a schematic view of another example of an applicator that may be associated with some embodiments of the bridge of FIG. 3A.

FIG. 3D is a schematic view of another example of the applicator 240, illustrating additional details that may be associated with some embodiments. In the example of FIG. 3D, some of the supports 365 around the recessed space 360 extend from the second layer 320 toward the first layer 315, and some of the supports 365 around the recessed space 360 also extend from the first layer 315 toward the second layer 320. Some of the supports 365 also extend from the first layer 315 toward the aperture 355 in the recessed space 360.

Figure 4A:
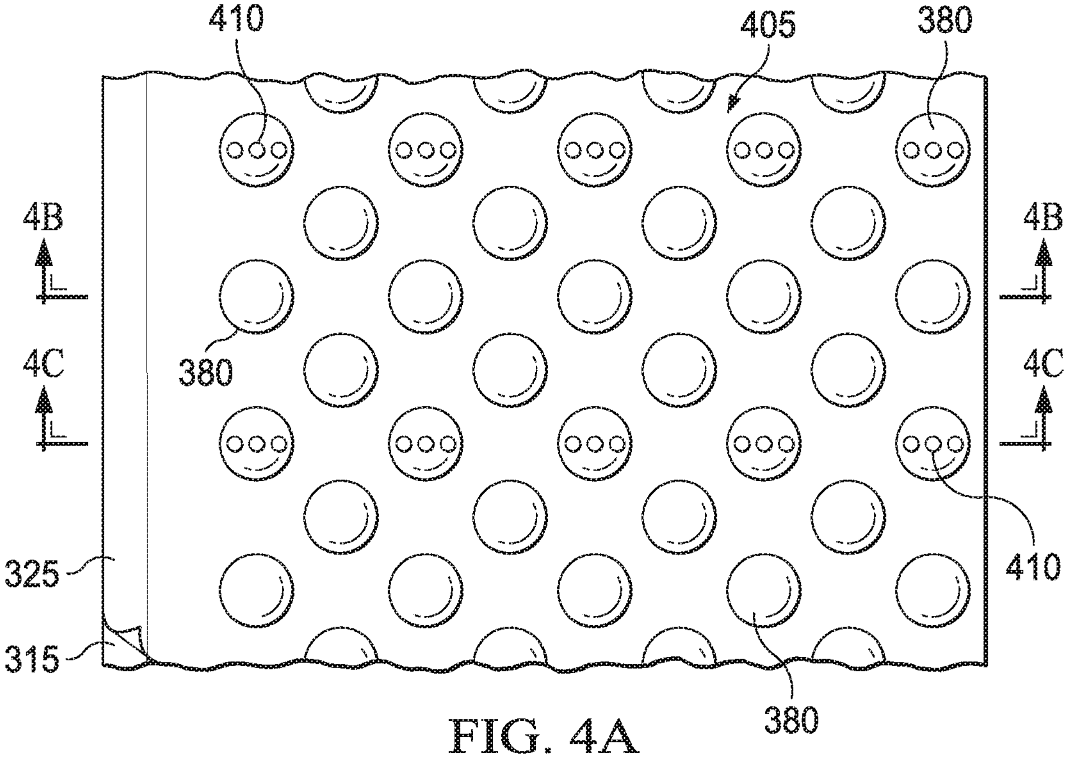
FIG. 4A is a schematic view of additional details that may be associated with various examples of support features in a bridge.

FIG. 4A is a schematic view of additional details that may be associated with various examples of support features in the bridge 160. For example, FIG. 4A illustrates a sealed region 405 between the standoffs 380. In some embodiments, the sealed region 405 may be formed by sealing portions of the spacer layer 375 to the first layer 315 or the second layer 320. In the example of FIG. 4A, the sealed region 405 may be formed by sealing the base 385 to the first layer 315 around the standoffs 380. As illustrated in the example of FIG. 4A, the standoffs 380 may have a circular edge proximate to the sealed region 405. In other embodiments, the standoffs 380 may have edges with other suitable shapes, such as rectangular, triangular, or hexagonal, or some combination of shapes. Additionally or alternatively, one or more of the standoffs 380 may be embossed with projections or nodes, such as the nodes 410 illustrated in the example of FIG. 4A.

The standoffs 380 in adjacent rows or columns may be staggered so that the standoffs 380 may be nested or packed together, as illustrated in the example of FIG. 4A. In other embodiments, the standoffs 380 may be arranged in other patterns suitable for the particular therapy being utilized. For example, the rows and columns of the standoffs 380 may be arranged in line to form an aligned, rectangular pattern so that there is more spacing between the standoffs 380. Increasing the spacing between the standoffs 380 may increase fluid flow within the fluid pathways of the bridge 160, whereas a nested arrangement may restrict fluid flow within the fluid pathways. For example, the standoffs 380 can be aligned to increase fluid flow of negative pressure being applied to a tissue interface and facilitate the removal of fluids and exudates within the recessed space 360. A nested pattern can facilitate pressure sensing within the recessed space 360 while impeding the inflow of fluids and exudates, which can reduce the possibility of blockage.

In some embodiments, distribution of the standoffs 380 may be characterized by a pitch, which can be defined by the center to center distance between each of the standoffs 380. For example, a pitch of about 1 mm to about 10 mm may be suitable for some configurations. In some embodiments, the pitch may be between about 2 mm and about 3 mm. Because the sealed region 405 can define an end of the standoffs 380, including a diameter of a circular end, and the pitch of the standoffs 380, the area of the spacer layer 375 having the standoffs 380 may also be determined as a percentage. For example, if each of the standoffs 380 has a diameter of about 1.0 mm and the pitch is about 2.0 mm, the coverage percentage is about 22% of the area of the spacer layer 375. In another example, if the diameter of each of the standoffs 380 is about 2.0 mm and the pitch is about 5.0 mm, the coverage percentage is about 14% of the area of the spacer layer 375. In yet another example, if the diameter of each of the standoffs 380 is about 1.5 mm, the pitch is about 2.0 mm, and the standoffs 380 are more tightly arranged such that there are about 28.5 standoffs in a 10 $mm^2$ section of the spacer layer 375, the coverage percentage is about 51% of the area of the spacer layer 375. Depending on the diameter, pitch, and arrangement of the standoffs 380, the coverage percentage may range between about 10% and about 60% of the surface area of the spacer layer 375. Support features having other shapes also may have a coverage percentage in generally the same range.

The size and pitch of the standoffs 380 also may be varied to effect change in the fluid flows through the fluid passageways. For example, the diameter and pitch of the standoffs 380 can be increased to increase fluid flow of negative pressure being applied to a tissue interface and facilitate the removal of fluids and exudates within the recessed space 360. The diameter, pitch, or both may be decreased to restrict fluid flow, which can reduce blockages, and facilitate pressure sensing within the recessed space 360.

Figure 4B:
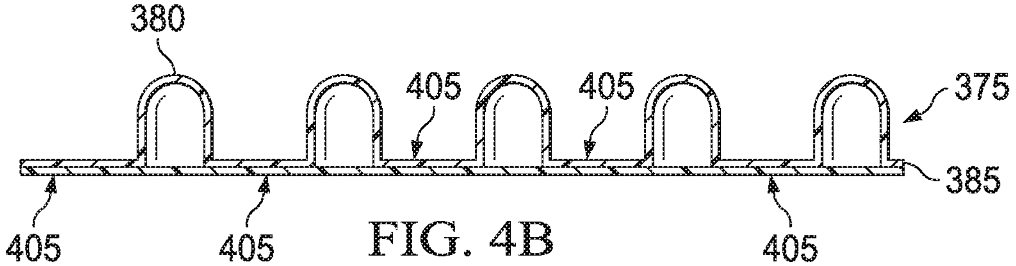
FIG. 4B is a schematic view of the support features of FIG. 4A taken along section 4B-4B, illustrating additional details that may be associated with some examples.

FIG. 4B is a schematic view of the support features of FIG. 4A taken along section 4B-4B, illustrating additional details that may be associated with some examples. In some embodiments, the standoffs 380 may have a hemispherical profile, as illustrated in the example of FIG. 4B. In other example embodiments, the standoffs 380 may be profiles that are conical, cylindrical, tubular having a flattened or hemispherical end, or geodesic. The standoffs 380 may be tubular in some embodiments, formed with generally parallel walls extending from the base 385 to a hemispherical or flat top portion of the standoffs 380. Alternatively, the walls of the standoffs 380 may taper or expand outwardly from the base 385. In some embodiments, the standoffs 380 that are generally hemispherical or tubular in shape may have a diameter between about 1.0 mm and about 10 mm. In some other embodiments, the standoffs 380 may have a diameter between about 2.0 mm and about 5.0 mm.

Figure 4C:
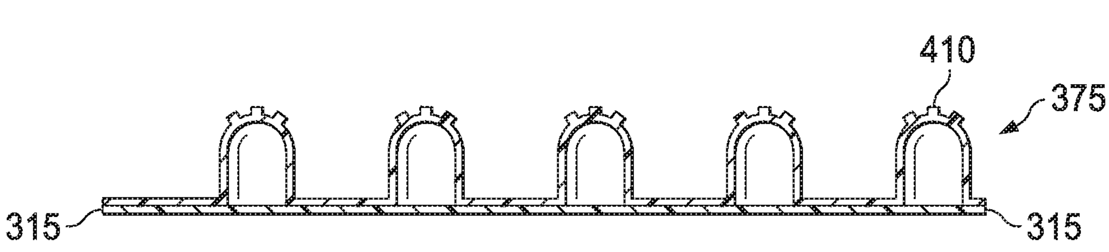
FIG. 4C is a schematic view of the example support features of FIG. 4A taken along section 4C-4C, illustrating additional details that may be associated with some embodiments.

FIG. 4C is a schematic view of the example support features of FIG. 4A taken along section 4C-4C, illustrating additional details that may be associated with some embodiments. In the example of FIG. 4C, the nodes 410 can be configured to contact the tissue interface 120 to enhance fluid flow to a tissue site. The nodes 410 may be flexible or rigid. In some embodiments, the nodes 410 may be formed from a substantially gas impermeable material, such as silicone. In other embodiments, the nodes 410 may be formed from a semi-gas permeable material. The nodes 410 may be formed from the same material as the spacer layer 375, and may be an integral part of the spacer layer 375. In some embodiments, the nodes 410 may be solid, while in other embodiments the projections may be hollow to increase flexibility. The nodes 410 may form a plurality of channels and/or voids to distribute reduced pressure and allow for fluid flow among the nodes 410. The nodes may be dimensioned to provide local load points evenly distributed at a tissue interface. The pattern and position of the nodes 410 may be uniform or non-uniform. The nodes may have different profiles, including, for example, the shape of a spike, cone, pyramid, dome, cylinder or rectangle.

Figure 5A:
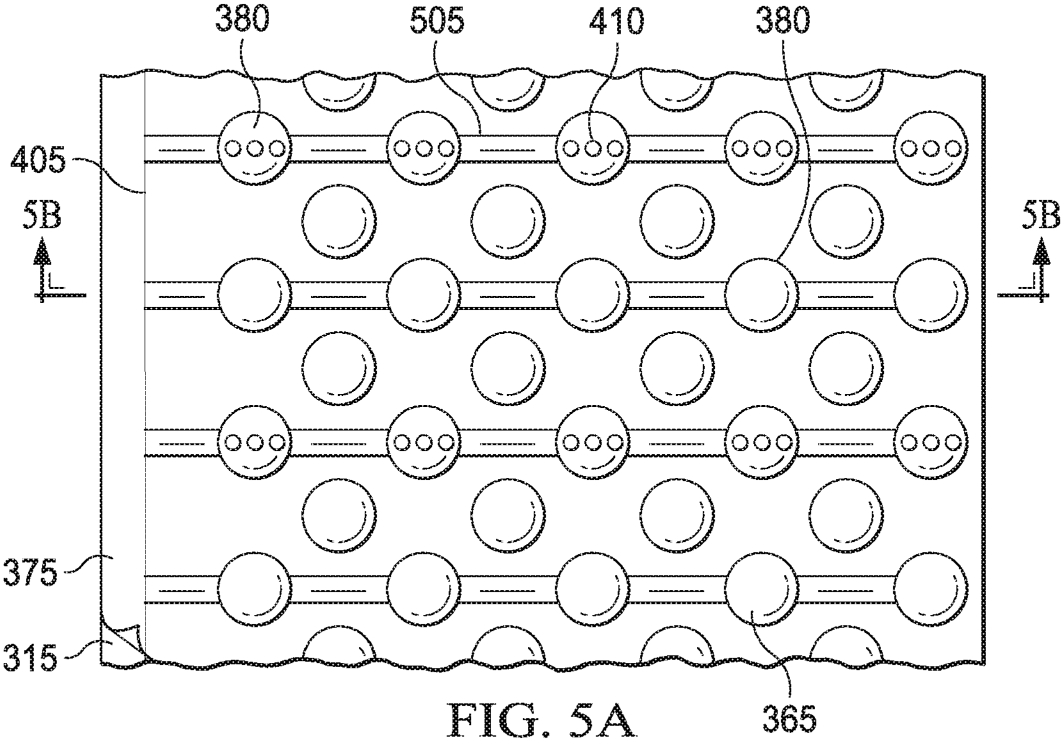
FIG. 5A is a schematic view of additional details that may be associated with some embodiments of a bridge in the therapy system of FIG. 1.

FIG. 5A is a schematic view of additional details that may be associated with some embodiments of the bridge 160. For example, in FIG. 5A one or more passageways 505 may be formed between the supports 365.

Figure 5B:
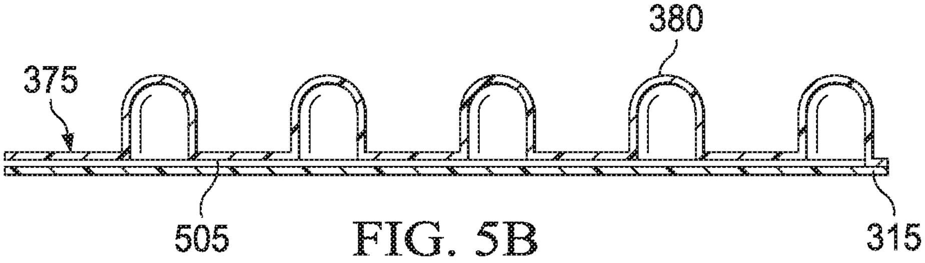
FIG. 5B is a schematic view taken along section 5B-5B of FIG. 5A, illustrating additional details that may be associated with some embodiments.

FIG. 5B is a schematic view taken along section 5B-5B of FIG. 5A, illustrating additional details that may be associated with some embodiments. For example, as seen in FIG.

5B, at least some of the standoffs 380 may be fluidly coupled through the passageways 505. The passageways 505 and the standoffs 380 can form a closed chamber. In some examples, a closed chamber may be formed by all of the standoffs 380 in a row fluidly coupled by the passageways 505 as shown in FIG. 5A and FIG. 5B. The closed chambers may be formed in alternating rows as also shown in FIG. 5A. The formation of closed chambers with the standoffs 380 can distribute apposition forces more equally.

Figure 6A:
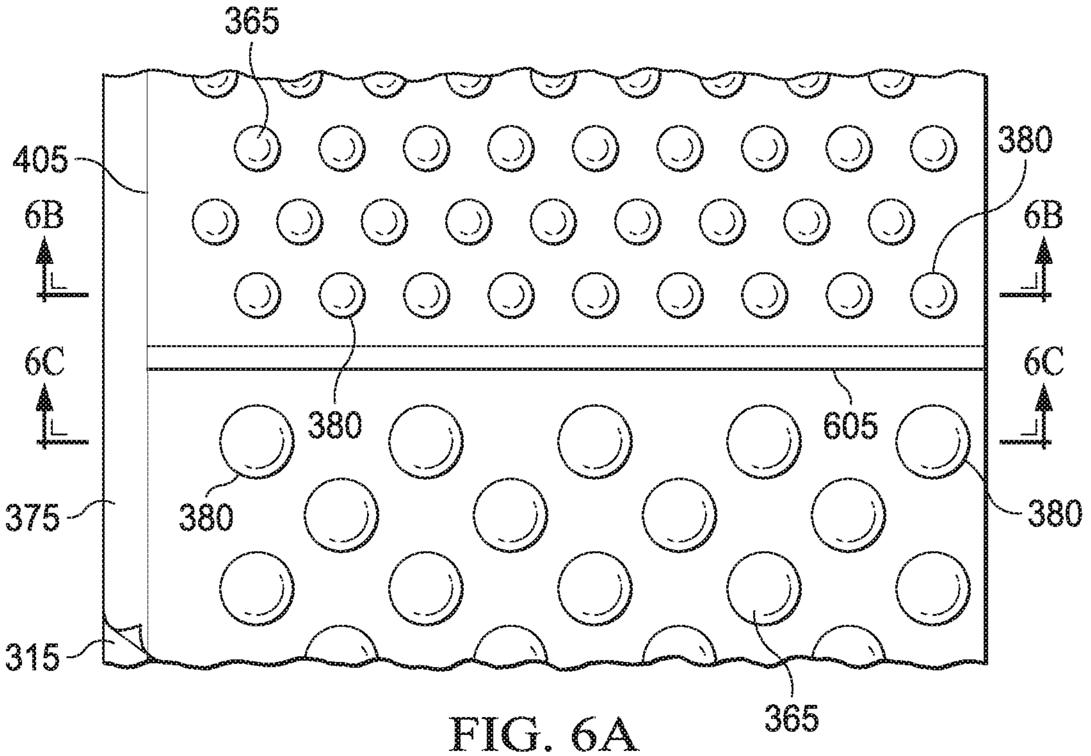
FIGS. 6A, 6B, and 6C illustrate other examples of features that may be associated with some embodiments of a bridge in the therapy system of FIG. 1.
Figure 6B:
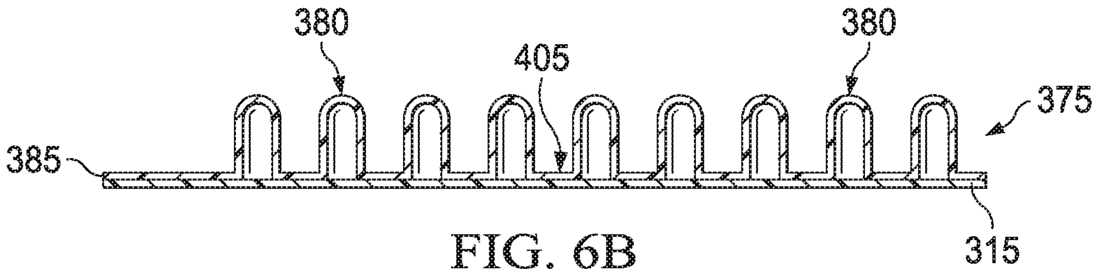
Figure 6C:
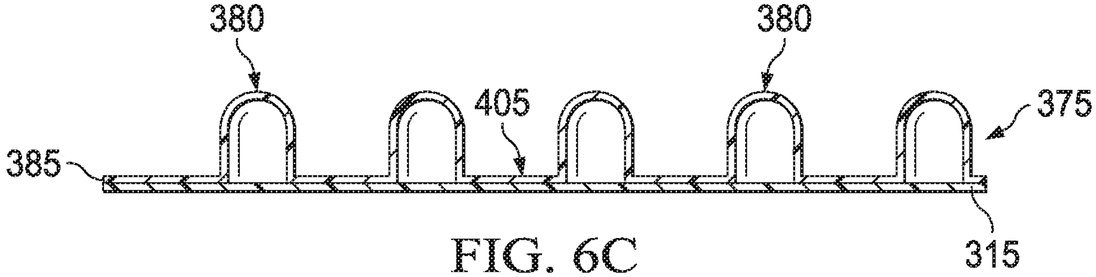

FIGS. 6A, 6B, and 6C illustrate other examples of features that may be associated with some embodiments of the bridge 160. In FIG. 6A, the first layer 315 and the spacer layer 375 define a nested arrangement of the supports 365. The example of FIG. 6A further illustrates that at least some of the supports 365 may additionally or alternatively have different sizes. For example, some of the supports 365 may have a diameter in the range between about 1 mm and about 10 mm, and some of the supports 365 may have a diameter in the range between about 1 mm and about 3 mm. In some embodiments, a wall 605 may be disposed between the some of the supports 365. For example, the wall 605 in the example of FIG. 6A is disposed between the supports 365 having different sizes. The supports 365 having a larger diameter and pitch may increase fluid flow to facilitate the removal of fluids and exudates within the recessed space 360 in some embodiments. In some embodiments, the supports 365 having a smaller diameter and pitch may restrict fluid flow to facilitate pressure sensing within the recessed space 360 while impeding the inflow of fluids and exudates into the first pathway 340. The arrangement and dimensions of the supports 365 may be tailored to manage the delivery of negative pressure to the tissue interface 120 and the measurement of pressure within the recessed space 360.

Figure 7:
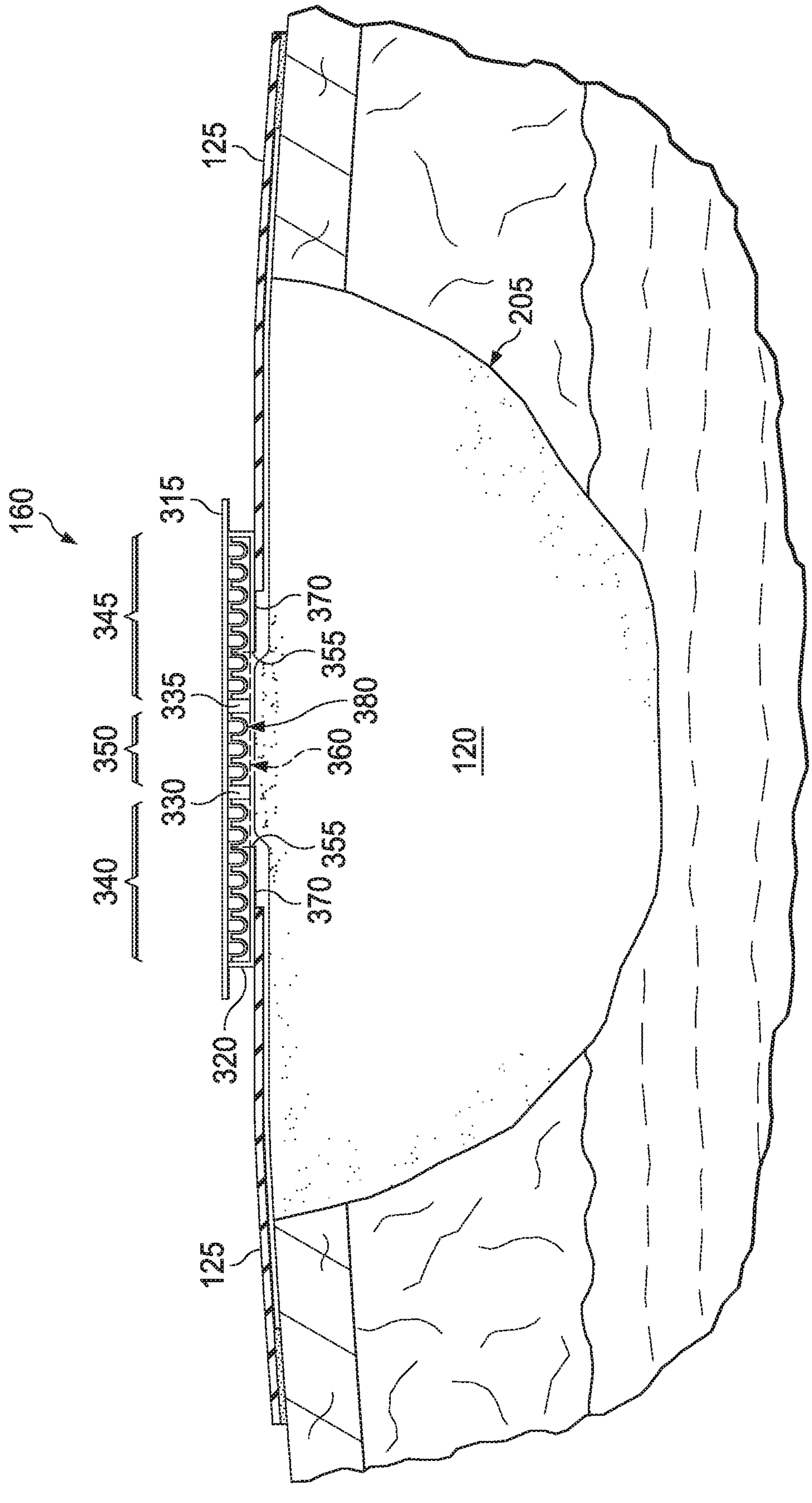
FIG. 7 is a schematic diagram of the bridge of FIG. 3A applied to a tissue site with negative pressure.

FIG. 7 is a schematic diagram of the bridge 160 of FIG. 3A applied to the tissue site 205 with negative pressure. The tissue interface 120 may be in fluid communication with the recessed space 360 through the aperture 355. The affixation surface 370 may be coupled to the cover 125 to seal and fluidly couple the recessed space 360 to the tissue interface 120. In the example of FIG. 7, the first wall 330 and the second wall 335 partially define the first pathway 340, the second pathway 345, and the third pathway 350 between the first layer 315 and the second layer 320.

Within the recessed space 360, the standoffs 380 can extend from the first layer 315 toward the tissue interface 120 and may be adapted to come in direct contact with the tissue interface 120 if negative pressure is applied to the bridge 160. Negative pressure can compress the bridge 160, and the first layer 315 and the second layer 320 can collapse toward each other because of the vacuum created within the standoffs 380. Although the standoffs 380 may change shape or flatten somewhat under negative pressure, the volume of the standoffs 380 remains substantially constant and can maintain fluid flow through the third pathway 350. The standoffs 380 can also provide a cushion to help prevent the sealed spaces of the bridge 160 from collapsing as a result of external forces. The standoffs 380 disposed in the third pathway 350 may be sized and arranged in a pattern that may increase fluid flow of negative pressure being applied to the tissue interface 120 to facilitate the removal of fluids and exudates within the recessed space 360. The standoffs 380 disposed in the first pathway 340 and the second pathway 345 may be sized and arranged in a pattern to facilitate pressure sensing within the recessed space 360 while impeding the inflow of fluids and exudates into the first pathway 340 and the second pathway 345 to reduce blockage conditions.

The standoffs 380 may have a variety of shapes, and may be sized and arranged in different patterns within the sealed space to enhance the delivery of negative pressure to the tissue interface 120 for a specific type of tissue site while optimizing pressure sensing and measurement of the negative pressure within the recessed space 360.

Figure 8:
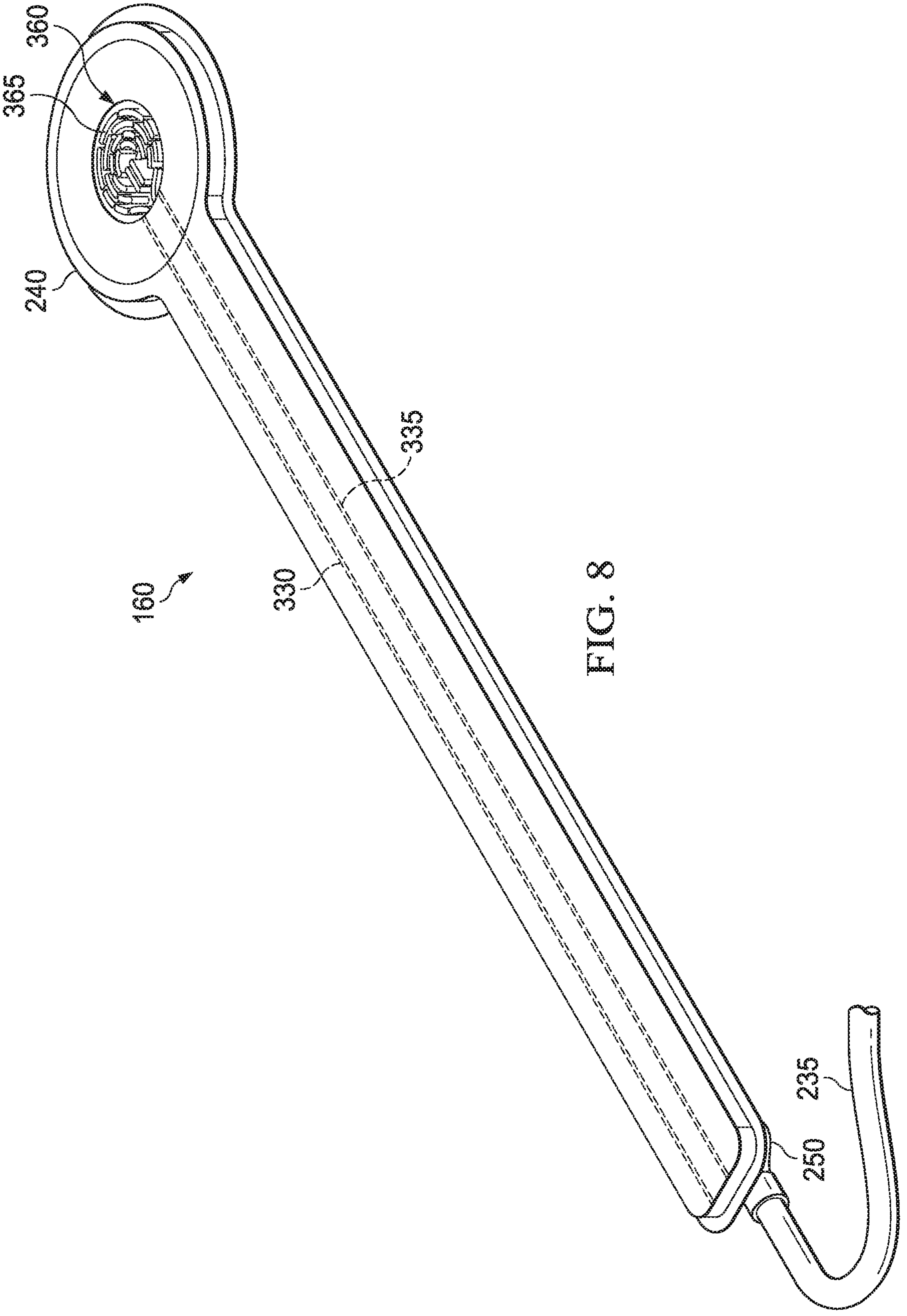
FIG. 8 is a perspective bottom view of another example of a bridge that may be associated with some embodiments of the therapy system of FIG. 1.

FIG. 8 is a perspective bottom view of another example of the bridge 160 having a low-profile structure that may be associated with some embodiments of the therapy system 100. As illustrated in the example of FIG. 8, the first wall 330 and the second wall 335 may extend lengthwise through the bridge 160 between the recessed space 360 and the adapter 250.

Figure 9A:
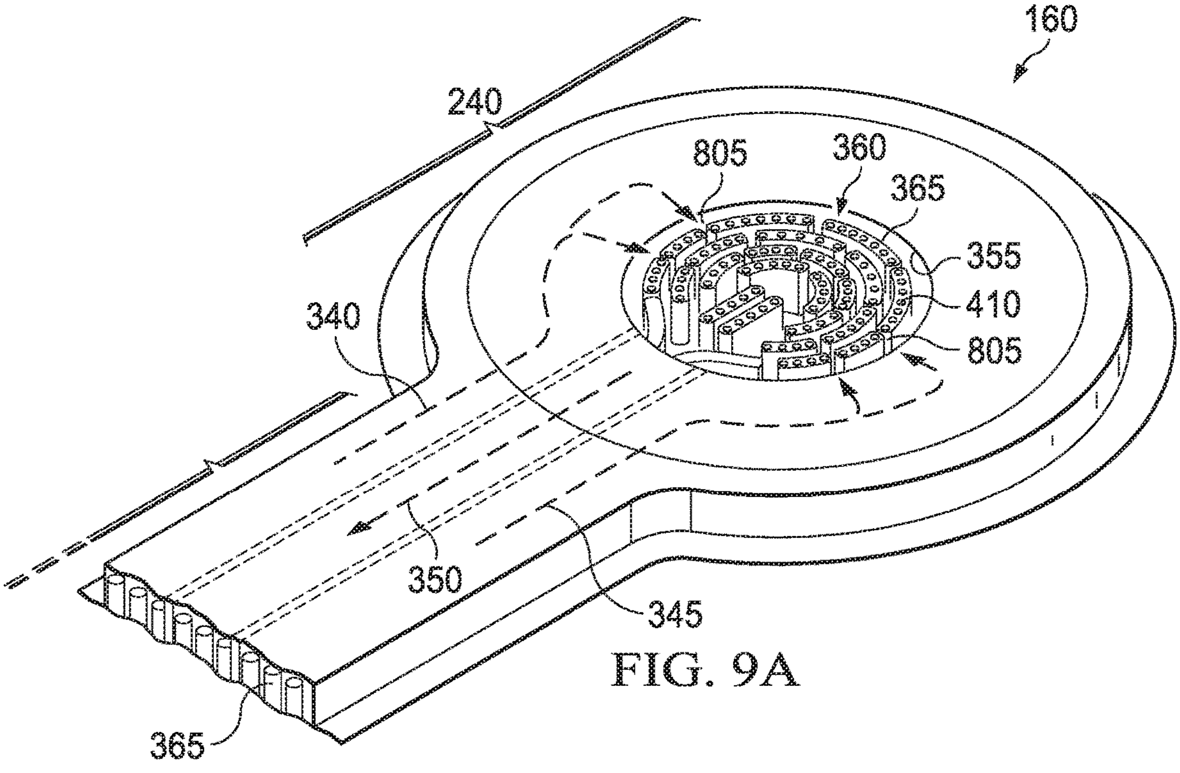
FIG. 9A and FIG. 9B are segmented perspective views of the bridge of FIG. 8.
Figure 9B:
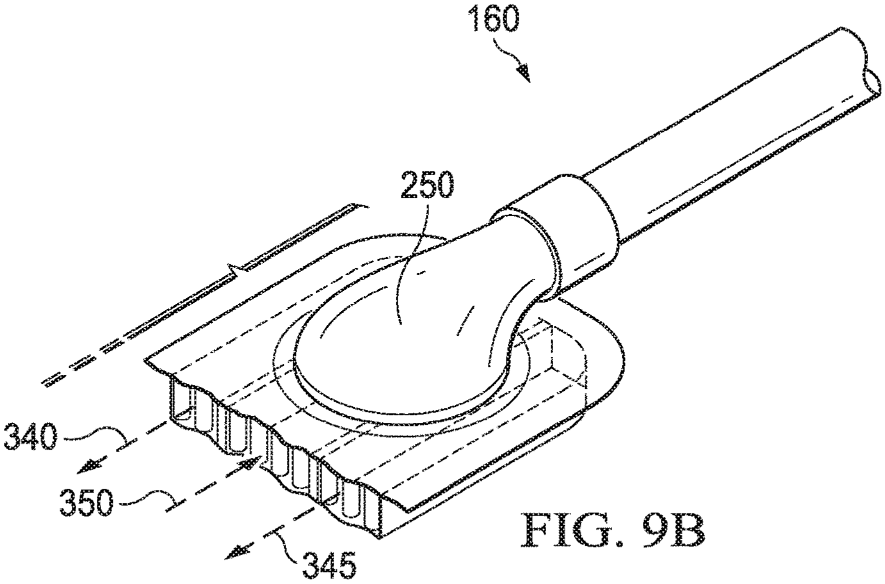

FIG. 9A and FIG. 9B are segmented perspective views of the bridge 160 of FIG. 8, illustrating additional details that may be associated with some examples. FIG. 9A is a bottom perspective view of an example of the applicator 240, illustrating a configuration having a circular profile. FIG. 9B is a top perspective view of an example of the adapter 250, which may have an elbow connector of semi-rigid material in some embodiments.

The aperture 355 of FIG. 9A is generally circular and opens to the recessed space 360. The supports 365 of FIG. 9A may have a generally elongated and arcuate profile and may be arranged in a generally concentric pattern within the recessed space 360. Some embodiments of the supports 365 may also comprise surface features, such as the nodes 410. The supports 365 disposed in the center of the recessed space 360 may be more aligned with the third pathway 350 to increase fluid flow of negative pressure being applied to the tissue interface 120 and facilitate the removal of fluids and exudates within the recessed space 360. In some embodiments, some of the supports 365 may be disposed around the aperture 355 to form a semicircular path opposite the third pathway 350, including spaces 805 between the supports 365. The semicircular alignment of the supports 365 may be positioned within the recessed space 360 to minimize contact with the flow of fluids passing through from the tissue interface 120 to the third pathway 350 if negative pressure is applied. Additionally, the spaces 805 may be sufficiently small for further restricting fluid flow into the first pathway 340 and the second pathway 345, as indicated by the dashed arrows. The spaces 805 can facilitate pressure sensing within the recessed space 360 while impeding the inflow of fluids and exudates into the first pathway 340 and the second pathway 345 to reduce the possibility of blockage. In some embodiments, a portion of the perimeter of the aperture 355 may be welded to an outer ring of the supports 365 to further restrict fluid flow to the first pathway 340 and the second pathway 345 and further impede the inflow of fluids and exudates without inhibiting pressure sensing within the recessed space 360.

Figure 10:
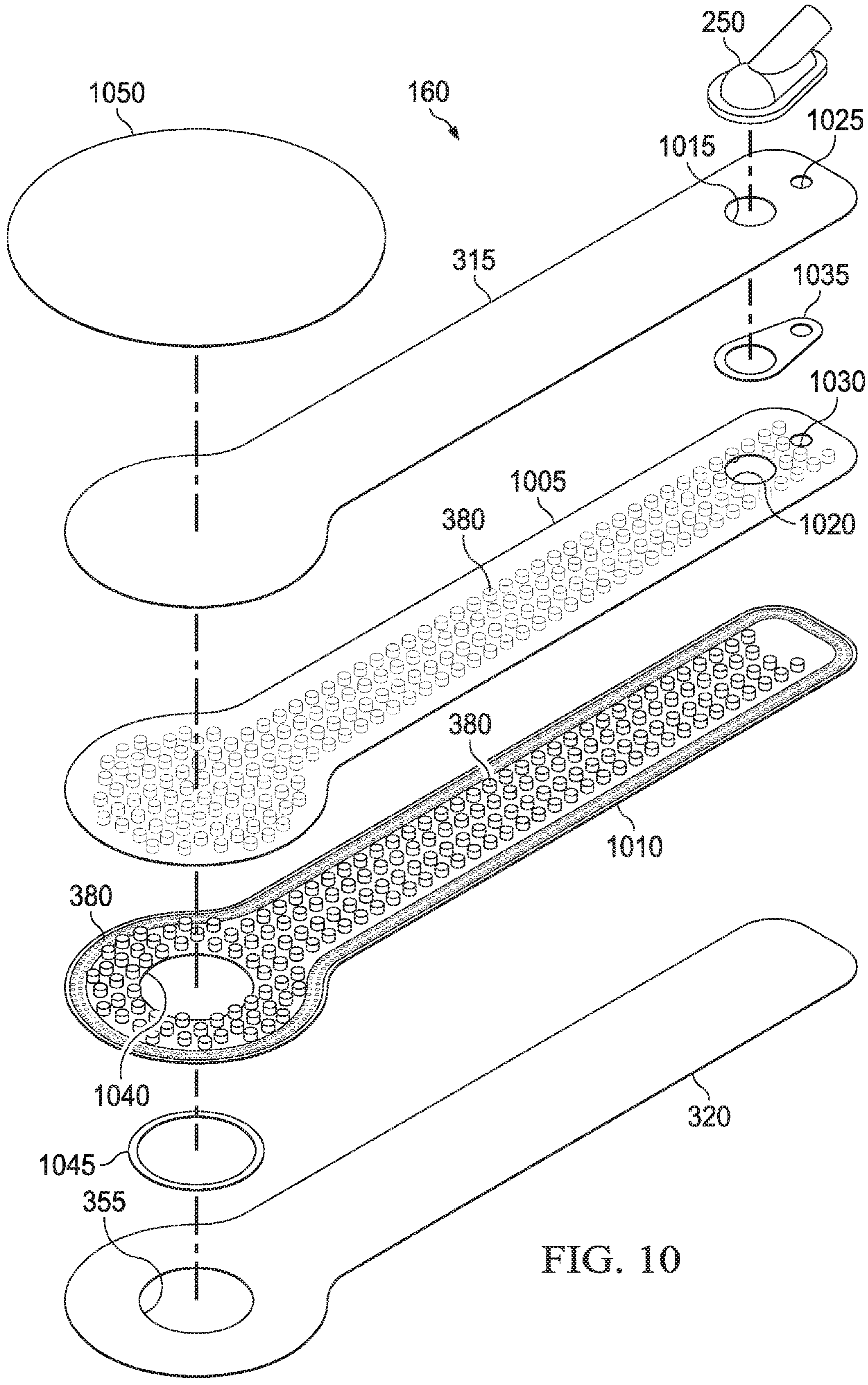
FIG. 10 is an assembly view of another example of a bridge that may be associated with some example embodiments of the therapy system of FIG. 1.

FIG. 10 is an assembly view of another example of the bridge 160 having a low-profile structure that may be associated with some example embodiments of the therapy system 100. In the example of FIG. 10, the bridge 160 comprises two spacer layers—a first spacer layer 1005 and a second spacer layer 1010—disposed between the first layer 315 and the second layer 320. In some embodiments, the first spacer layer 1005 and the second spacer layer 1010 may each be similar to spacer layer(s) 375. For example, standoffs 380 may be formed in each of the first spacer layer 1005 and the second spacer layer 1010. In the example of FIG. 10, the standoffs 380 in the first spacer layer 1005 are configured to extend toward the second spacer layer 1010, and the standoffs 380 in the second spacer layer 1010 are configured to extend toward the first spacer layer 1005. The first layer

315 may have a passage 1015, and the first spacer layer 1005 may have a passage 1020, through which fluids may flow to the adapter 250. The first layer 315 and the first spacer layer 1005 may additionally have a passage 1025 and a passage 1030, respectively, which may also be fluidly coupled to the adapter 250. The bridge 160 may further comprise a fluid exit bond 1035 to prevent leakage of fluids flowing through the passage 1015 and the passage 1020. The second spacer layer 1010 may have an aperture 1040 concentric with the aperture 355 of the second layer 320. The bridge 160 may further comprise a fluid exit bond 1045, which can prevent leakage of fluids flowing through the aperture 355 and the aperture 1040.

In some embodiments, a bridge cover 1050 may provide additional protection and support over the applicator 240 if the bridge 160 is applied to a tissue site. In some embodiments, the bridge cover 1050 may also cover any adhesive that might be exposed from applying the bridge 160 to a tissue site. In some embodiments, the bridge cover 1050 may be similar or analogous to the cover 125. For example, the bridge cover 1050 may be a polymer, such as a polyurethane film.

Figure 11A:
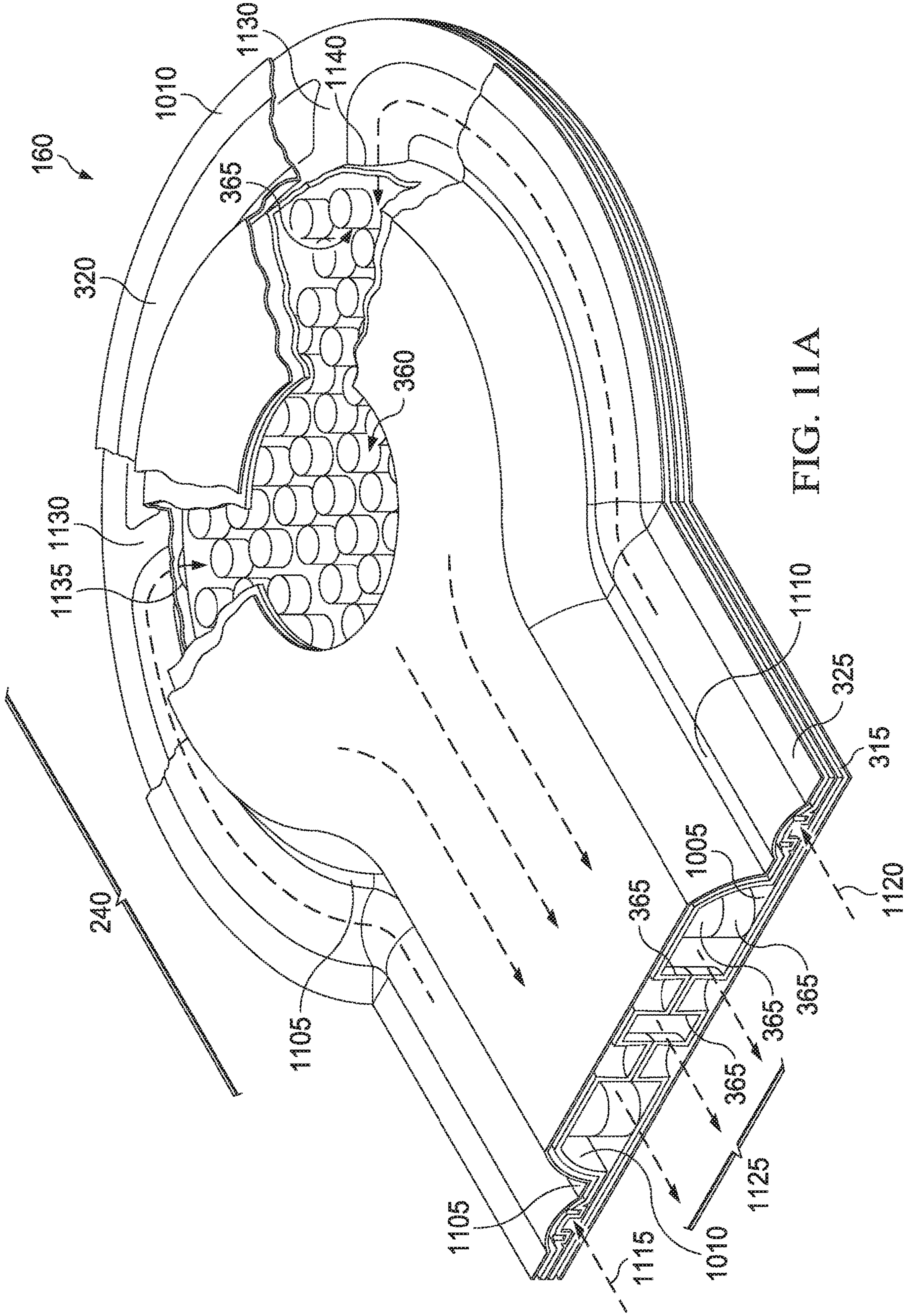
FIG. 11A is a segmented view of an assembled portion of the bridge in the example of FIG. 10, illustrating additional details that may be associated with some embodiments.

FIG. 11A is a segmented view of an assembled portion of the bridge 160 in the example of FIG. 10, illustrating additional details that may be associated with some embodiments. As illustrated in the example of FIG. 11A, the first layer 315, second layer 320, the first spacer layer 1005, and the second spacer layer 1010 may be assembled in a stacked relationship. For example, the first layer 315 may be coupled to the first spacer layer 1005, the second layer 320 may be coupled to the second spacer layer 1010, and a periphery of the first spacer layer 1005 may be coupled to a periphery of the second spacer layer 1010 to form the flange 325. The first spacer layer 1005 and the second spacer layer 1010 can be coupled to form a liquid barrier defining a fluid path along a longitudinal axis of the bridge 160.

Some embodiments of the bridge 160 may additionally comprise at least one barrier or wall, such as a first barrier 1105, interior to the flange 325. The first barrier 1105 may be formed by coupling the first spacer layer 1005 and the second spacer layer 1010. For example, the first spacer layer 1005 may be welded to the second spacer layer 1010 to form the first barrier 1105. In some embodiments, the first barrier 1105 may extend lengthwise through the bridge 160 into the applicator 240 to form at least two fluid paths between the first spacer layer 1005 and the second spacer layer 1010 within the bridge 160. In some examples, the bridge 160 may further comprise a second barrier, such as a second barrier 1110. The second barrier 1110 may be formed by coupling the first spacer layer 1005 and the second spacer layer 1010. In some embodiments, the second barrier 1110 also may extend lengthwise through the bridge 160 into the applicator 240. In some example embodiments, the first barrier 1105 and the second barrier 1110 may comprise a polymeric film coupled between the first layer 315 and the second layer 320. In some other example embodiments, the first barrier 1105 and the second barrier 1110 may comprise a weld (RF or ultrasonic), a heat seal, an adhesive bond, or a combination of any of the foregoing. The first barrier 1105 and the second barrier 1110 may be similar to the first wall 330 and the second wall 335 in some embodiments.

In some embodiments, barriers or walls interior to the flange 325 may form fluid pathways between the first spacer layer 1005 and the second spacer layer 1010. For example, in FIG. 11A, the first barrier 1105 and the second barrier 1110 cooperate with the flange 325 to form a first fluid conductor 1115, a second fluid conductor 1120, and a third fluid conductor 1125. In some applications, the first fluid conductor 1115 and the second fluid conductor 1120 may be coupled to a sensor to measure pressure, and the third fluid conductor 1125 may be coupled to a negative-pressure source. In some example embodiments, the first fluid conductor 1115 and the second fluid conductor 1120 may have a height having a value in a range between about 0.25 mm and about 3 mm. In some example embodiments, the first fluid conductor 1115 and the second fluid conductor 1120 may have a width having a value in a range between about 1 mm and about 7.5 mm. Thus, the first fluid conductor 1115 and the second fluid conductor 1120 may have a cross-sectional area having a value in a range between about 0.17 $mm^2$ and 16.77 $mm^2$. In some embodiments, the first fluid conductor 1115 and the second fluid conductor 1120 may have a cross-sectional area having a value in a range between about 0.1 $mm^2$ and 18 $mm^2$.

In some examples, each of the first barrier 1105 and the second barrier 1110 may extend an angular distance around the proximal end of the applicator 240 and cooperate with blocking walls of the flange 325, such as blocking walls 1130, to form extensions of the first fluid conductor 1115 and the second fluid conductor 1120. The extensions may be fluidly coupled to the recessed space 360. In the example of FIG. 11A, the first fluid conductor 1115 and the second fluid conductor 1120 are fluidly coupled to the recessed space 360 through passages, such as a through-hole 1135 and a through-hole 1140, respectively. In some examples, at least some of the supports may be disposed in one or both of the first fluid conductor 1115 and the second fluid conductor 1120. For example, some of the supports may be formed by the standoffs 380 disposed between the flange 325 and the first barrier 1105, and between the flange 325 and the second barrier 1110. Additionally or alternatively, the thickness of the spacer layer 1010 may be increased to provide additional structural support to the first fluid conductor 1115 and the second fluid conductor 1120. In some examples, the first fluid conductor 1115 and the second fluid conductor 1120 may comprise or be formed by tubes through or along the bridge 160. Some configurations may not have the first fluid conductor 1115 or the second fluid conductor 1120, or may have only one of the first fluid conductor 1115 and the second fluid conductor 1120.

Each of the first barrier 1105 and the second barrier 1110 can extend at least partially around the proximal end of the applicator 240 that form the first fluid conductor 1115 and the second fluid conductor 1120. For example, in some embodiments each of the first barrier 1105 and the second barrier 1110 can extend from about 45° to about 315° from the center of the third fluid conductor 1125 where the third fluid conductor 1125 is in fluid communication with the recessed space 360. In some embodiments, the angular distance may be different for each of the first fluid conductor 1115 and the second fluid conductor 1120. For example, the angular distance for each of the first fluid conductor 1115 and the second fluid conductor 1120 may be about 60° and 210°, respectively, from the third fluid conductor 1125.

In some example embodiments, the through-hole 1135 and the through-hole 1140 may be separated from each other by an angular distance of at least 90°, extending around the applicator 240 in a direction away from the third fluid conductor 1125. The spacing and disposition of the through-hole 1135 and the through-hole 1140 from each other, and from the third fluid conductor 1125, can allow the first fluid conductor 1115 and the second fluid conductor 1120 to better avoid the flow of fluids passing through from the tissue interface 120 to the third fluid conductor 1125 when negative pressure is applied. Additionally, the through-hole 1135 and the through-hole 1140 may be sufficiently small for further restricting fluid flow into the first fluid conductor 1115 and the second fluid conductor 1120. In some embodiments, the through-hole 1135 and the through-hole 1140 may have a cross-sectional area having a value in a range between about 0.17 $mm^2$ and 16.77 $mm^2$. In some embodiments, the through-hole 1135 and the through-hole 1140 may have a cross-sectional area having a value in a range between about 0.1 $mm^2$ and 18 $mm^2$ to further restrict fluid flow to the first fluid conductor 1115 and the second fluid conductor 1120 and impede the inflow of fluids and exudates without inhibiting pressure sensing within the recessed space 360.

Figure 11B:
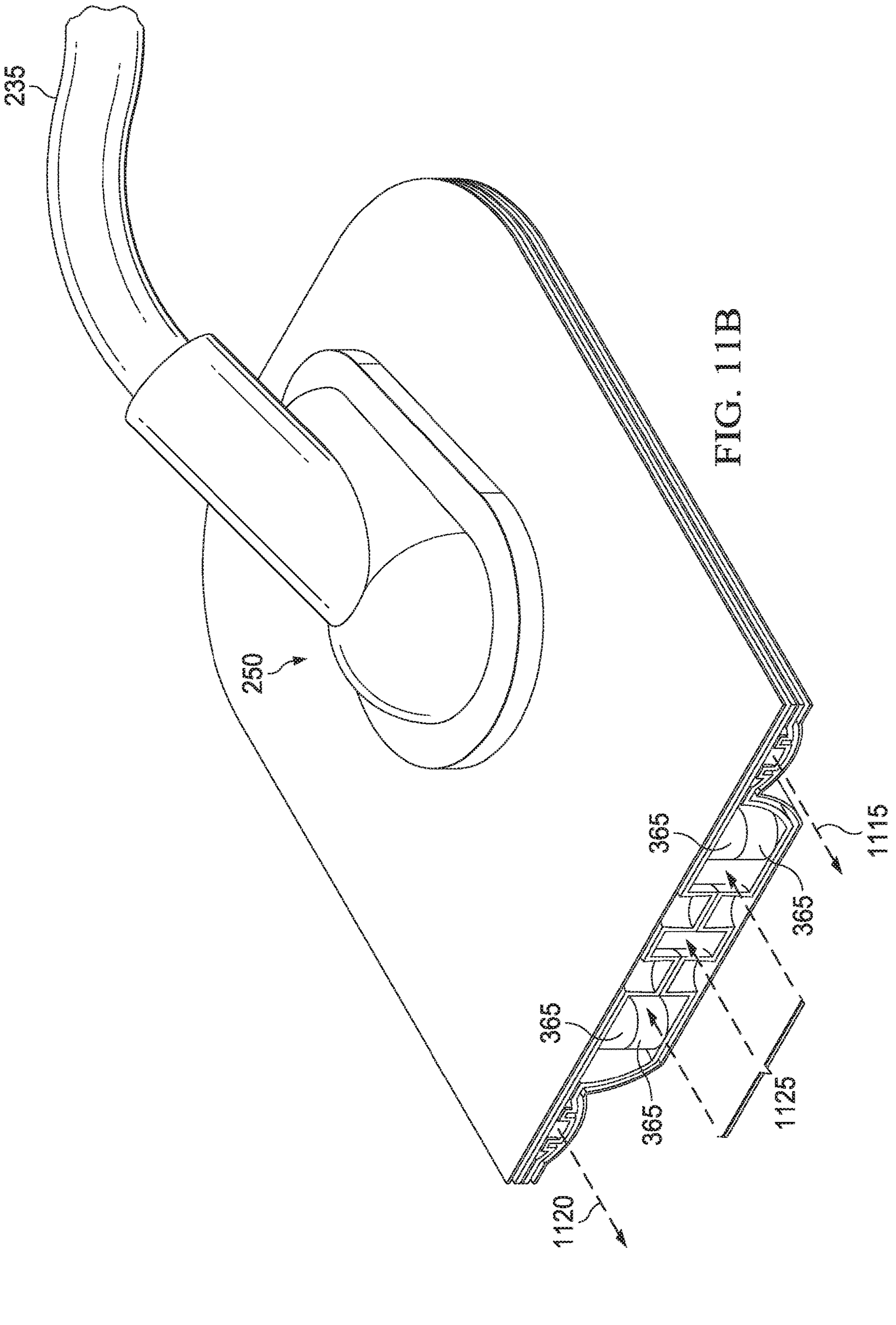
FIG. 11B is a segmented perspective view of portion of the bridge in the example of FIG. 10, illustrating additional details that may be associated with some embodiments.

FIG. 11B is a segmented perspective view of portion of the bridge 160 in the example of FIG. 10, illustrating additional details that may be associated with some embodiments. FIG. 11B further illustrates an example of the adapter 250 and the conduit 235 coupled to the bridge 160. Each of the first fluid conductor 1115 and the second fluid conductor 1120 may be fluidly coupled directly to the conduit 235 in some examples. In other examples, both of the first fluid conductor 1115 and the second fluid conductor 1120 may be fluidly coupled to a single space (not shown) within the adapter 250, which can be fluidly coupled to the conduit 235.

In the example of FIG. 11A and FIG. 11B, both the first fluid conductor 1115 and the second fluid conductor 1120 are fluidly separate from and parallel to the third fluid conductor 1125. The parallel orientation can minimize the vertical profile of the bridge 160, while still being resistant to collapsing under pressure that could block fluid flow through the fluid pathways.

Figure 12A:
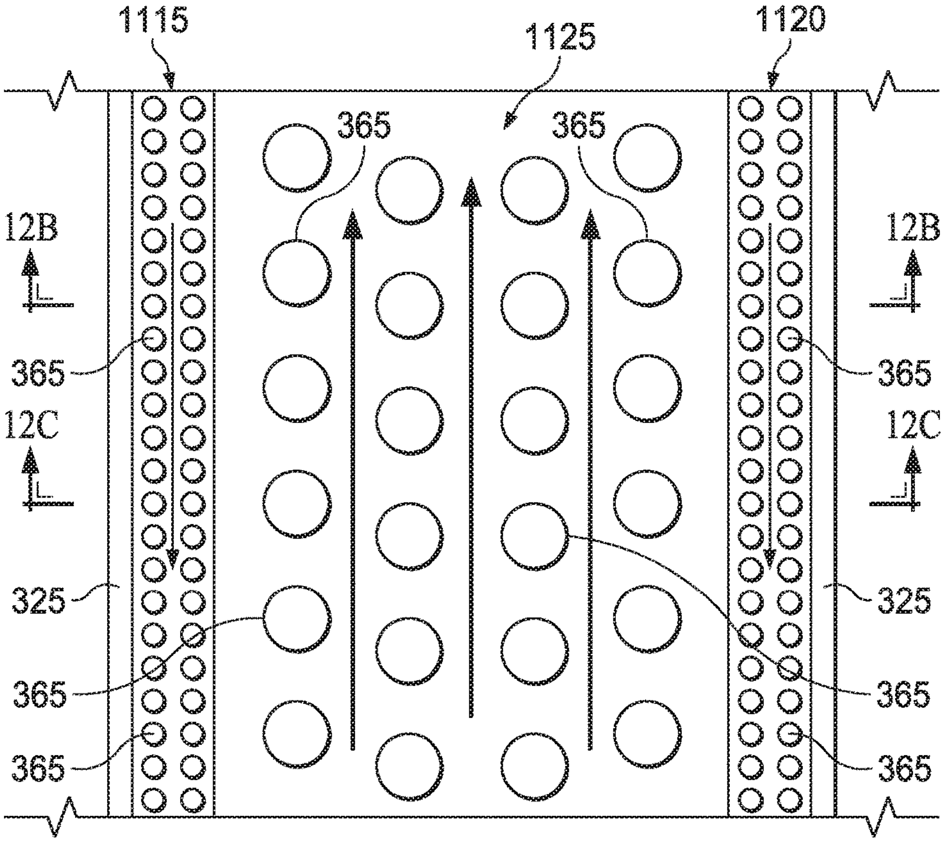
FIG. 12A is a schematic view of an example configuration of fluid pathways in the bridge of FIG. 10 as assembled, illustrating additional details that may be associated with some embodiments.
Figure 12B:
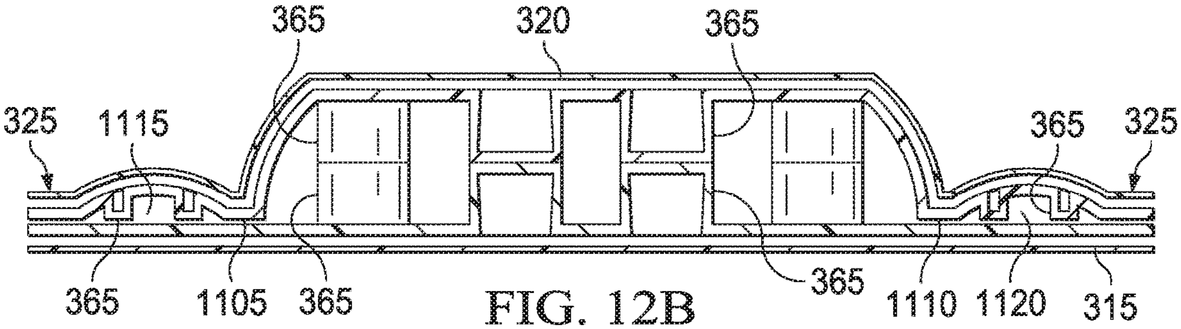
FIG. 12B is a schematic view taken along line 12B-12B of FIG. 12A.
Figure 12C:
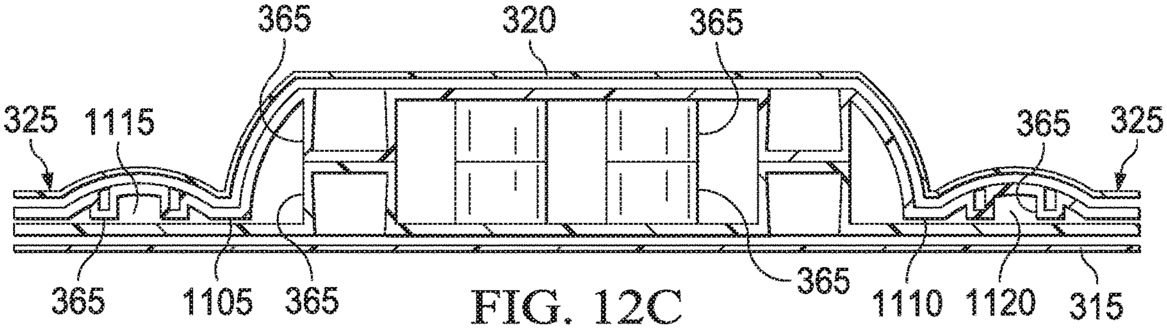
FIG. 12C is a schematic view taken along line 12C-12C of FIG. 12A.

FIG. 12A is a schematic view of an example configuration of fluid pathways in the bridge 160 of FIG. 10 as assembled, illustrating additional details that may be associated with some embodiments. FIG. 12B is a schematic view taken along line 12B-12B, and FIG. 12C is a schematic view taken along line 12C-12C. The supports 365 may have a variety of shapes, and may be sized and arranged in different patterns within the third fluid conductor 1125. For example, as illustrated in the examples of FIG. 12B and FIG. 12C, some of the supports 365 may extend from the first layer 315 and some of the supports 365 may extend from the second layer 320. In some embodiments, some of the supports 365 may be opposingly aligned. For example, at least some of the supports 365 can extend from the first layer 315 towards some of the supports 365 extending from the second layer 320, and some of the supports 365 in opposition may contact each other. In some embodiments, the bridge 160 may include more than one row of the supports 365. In the example of FIG. 12A, the bridge 160 has four rows of the supports 365, and the supports 365 forming outside rows are offset or staggered from the supports 365 forming the two inside rows. Each of the first barrier 1105 and the second barrier 1110 cooperate with the flange 325 to form the first fluid conductor 1115 and the second fluid conductor 1120. In some embodiments, some of the supports 365 may be disposed within one or both of the first fluid conductor 1115 and the second fluid conductor 1120.

The supports 365 disposed in the third fluid conductor 1125 may have a larger diameter and pitch than the supports 365 in the first fluid conductor 1115 and the second fluid conductor 1120, and may increase fluid flow to facilitate the removal of fluids and exudates within the recessed space 360. The supports 365 in the first fluid conductor 1115 and the second fluid conductor 1120 may have a noticeably smaller diameter and pitch than the supports 365 in the third fluid conductor 1125, and may restrict fluid flow to facilitate pressure sensing within the recessed space 360 while impeding the inflow of fluids and exudates into the first fluid conductor 1115 and the second fluid conductor 1120. The arrangement and dimensions of the supports 365 may be tailored to manage the delivery of negative pressure to the tissue interface 120 and the measurement of pressure within the recessed space 360.

Figure 13A:
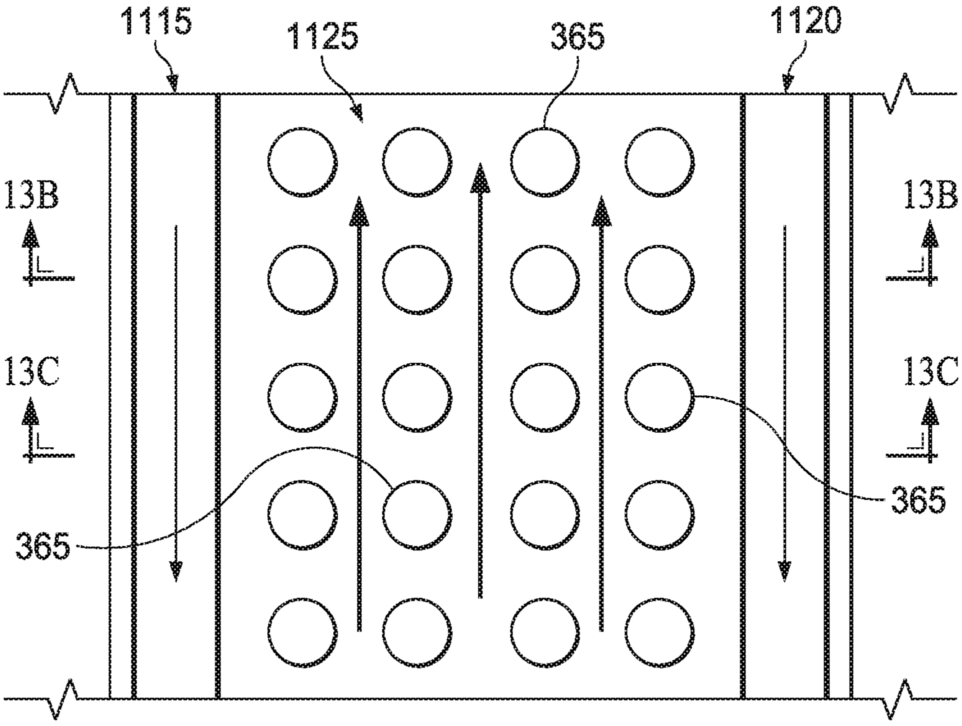
FIG. 13A is a schematic view of another example configuration of fluid pathways in the bridge of FIG. 10 as assembled, illustrating additional details that may be associated with some embodiments.
Figure 13B:
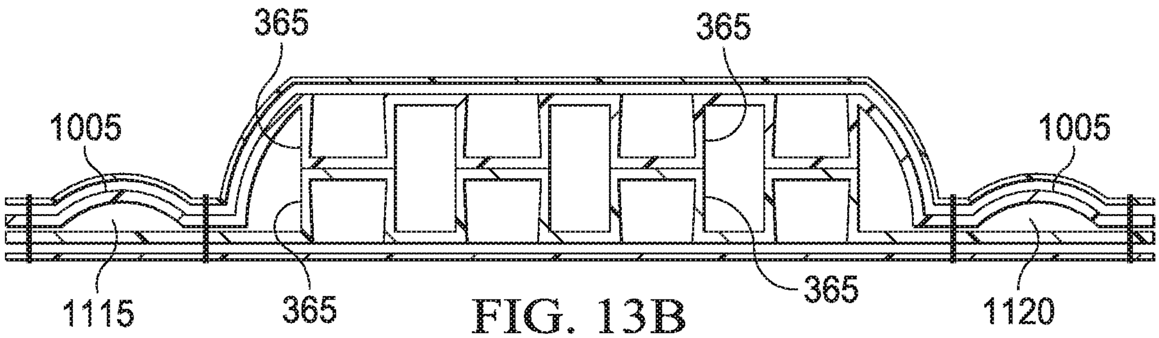
FIG. 13B is a schematic view taken along line 13B-13B of FIG. 13A.
Figure 13C:
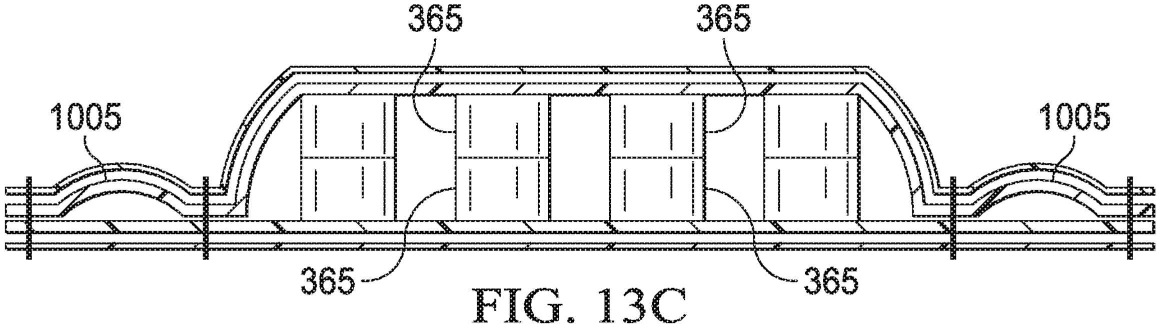
FIG. 13C is a schematic view taken along line 13C-13C of FIG. 13A.

FIG. 13A is a schematic view of another example configuration of fluid pathways in the bridge 160 of FIG. 10 as assembled, illustrating additional details that may be associated with some embodiments. FIG. 13B is a schematic view taken along line 13B-13B, and FIG. 13C is a schematic view taken along line 13C-13C. The example of FIG. 13A includes four rows of the supports 365, which are aligned both horizontally and vertically rather than being offset or staggered with each other. In some embodiments, the first fluid conductor 1115 and the second fluid conductor 1120 may be opened and supported by increasing the thickness of the first spacer layer 1005.

Figure 14:
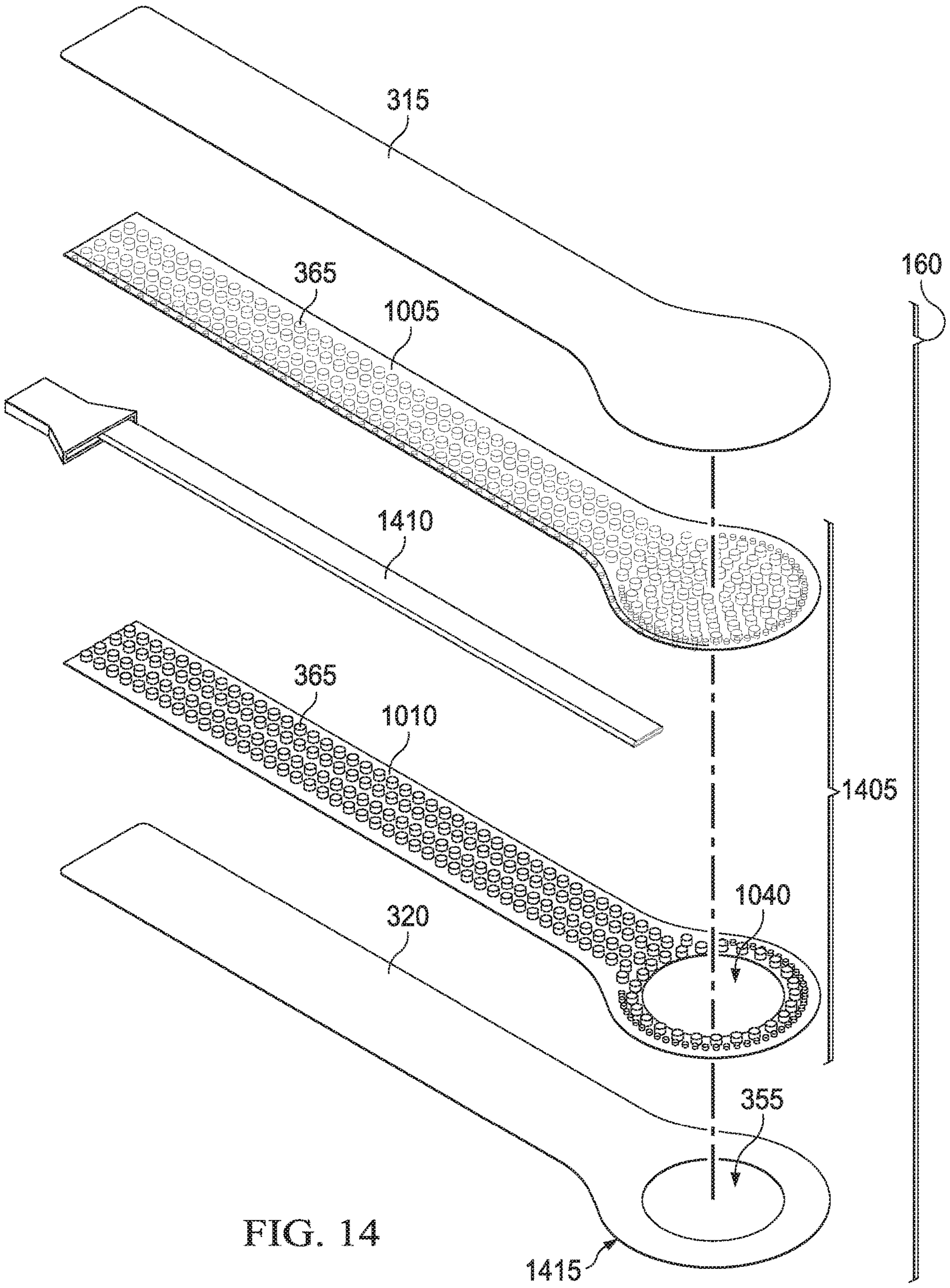
FIG. 14 is an assembly view of another example of a bridge for negative pressure therapy, which has integrated instillation, illustrating additional details that may be associated with some embodiments.

FIG. 14 is an assembly view of another example of the bridge 160 having a low-profile structure that may be associated with some example embodiments of the therapy system 100. The bridge 160 in FIG. 14 may be configured to provide instillation and negative-pressure therapy. For example, a negative-pressure pathway 1405 may be formed in the bridge 160, and an instillation pathway may be located within the negative-pressure pathway 1405. In the embodiment shown in FIG. 14, the bridge 160 may be similar to that shown in FIG. 10, but may further comprise an instillation pathway within an instillation conduit 1410 located within the negative-pressure pathway 1405.

For example, the bridge 160 in FIG. 14 may comprise the first layer 315, the first spacer layer 1005, the instillation conduit 1410 forming the instillation pathway, the second spacer layer 1010, and the second layer 320. In FIG. 14, the instillation conduit 1410 may be stacked between the first spacer layer 1005 and the second spacer layer 1010, with the supports 365 of the first spacer layer 1005 and the supports 365 of the second spacer layer 1010 extending inward towards the instillation conduit 1410. The first layer 315 may be adjacent to and in stacked relationship with the first spacer layer 1005, opposite the instillation conduit 1410. The second layer 320 may be adjacent to and in stacked relationship with the second spacer layer 1010, opposite the instillation conduit 1410. The first layer 315 and the second layer 320 may be sealed together about the perimeter, forming the enclosed negative-pressure pathway 1405 supported by the first spacer layer 1005 and the second spacer layer 1010, with the instillation conduit 1410 located within the negative-pressure pathway 1405 and between the supports 365 of the first spacer layer 1005 and the second spacer layer 1010.

In FIG. 14, the second layer 320 may comprise an aperture 355 configured to allow fluid communication between the negative-pressure pathway 1405 and the ambient environment. The aperture 355 in FIG. 14 may be located in a distal end 1415 of the bridge 160. Some embodiments may also comprise a second aperture 1040 located in the second spacer layer 1010 which may be concentric with the aperture 355 of the second layer 320. In some embodiments, the first layer 315 and the second layer 320 may be coupled to form the enclosed space of the negative-pressure pathway 1405 between the first layer 315 and the second layer 320. In some embodiments, the first layer 315 and the second layer 320 may each be formed of a film. Other embodiments may form the negative-pressure pathway 1405 as an open pathway using only a single spacer layer. Other embodiments may form the negative-pressure pathway 1405 by sealing the first spacer layer 1005 to the second spacer layer 1010 about the perimeter, for example without the need for any exterior film layers. Other embodiments may form the negative-pressure pathway 1405 between the first layer 315 and the second layer 320, while having the plurality of supports located therebetween without any spacer layer. For example, longitudinal tubular supports might be located between the first layer 315 and the second layer 320 in some alternate embodiments, along with the instillation conduit 1410.

In some embodiments, the instillation pathway and the negative pressure pathway may be located within a single bridge 160, as shown in FIG. 14. In some embodiments, the bridge 160 may be configured with a low profile. For example, the bridge 160 may have a height of approximately 5 millimeters. Some embodiments may have a height of less than approximately 5 millimeters. Some embodiments of the bridge 160 may have a length from approximately 200 millimeters to 500 millimeters.

Figure 15A:
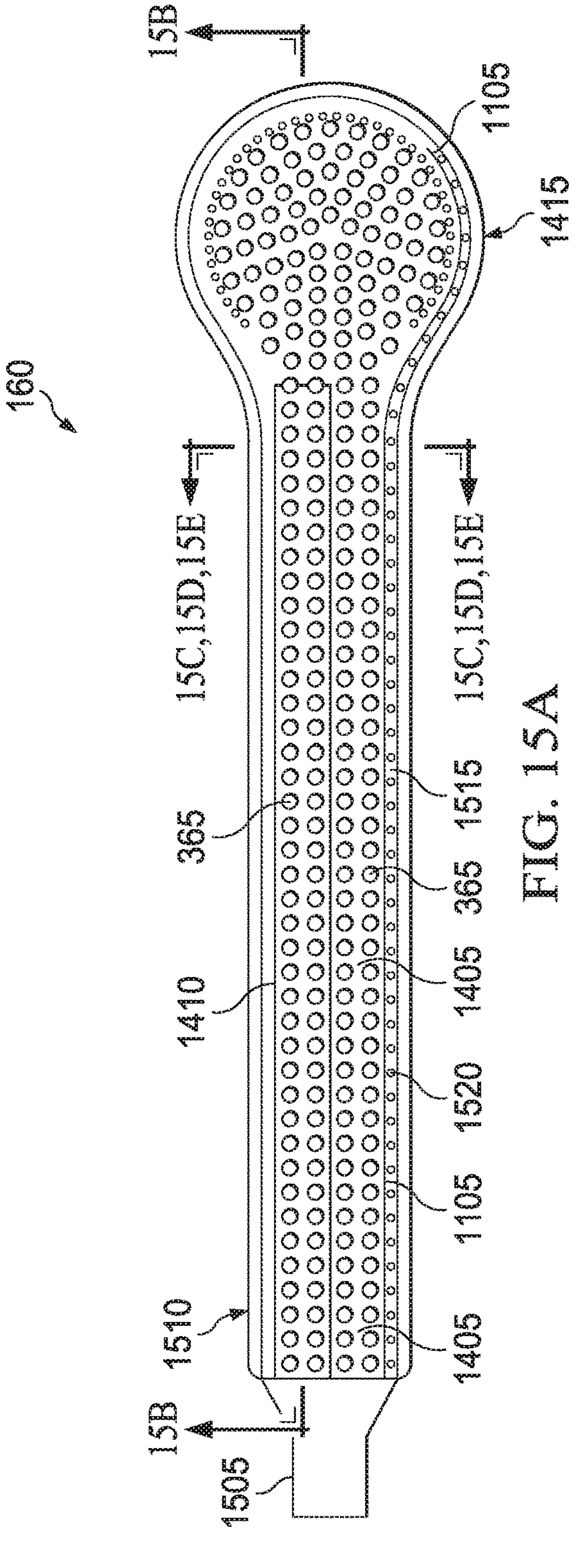
FIG. 15A is a plan view of the bridge of FIG. 14.

FIG. 15A is a plan view of the bridge 160 of FIG. 14, illustrating additional details that may be associated with some embodiments. As shown in FIG. 15A, the negative-pressure pathway 1405 is supported as an open pathway by the plurality of supports 365. In some embodiments, the plurality of supports 365 may be configured to support the negative-pressure pathway 1405 substantially along its entire length and/or width. For example, the supports 365 may be co-extensive with the negative-pressure pathway 1405. In some embodiments, the plurality of supports 365 may be arranged in rows, and the rows may be aligned and may extend longitudinally. For example, the rows may extend the length of the bridge 160, with longitudinally extending spaces of the negative-pressure pathway 1405 separating the rows. The row configuration of supports 365 may allow fluid flow longitudinally from one end of the negative-pressure pathway 1405 to the other, for example when the bridge 160 is under compression. For example, in the row configuration of supports 365, the longitudinally extending spaces may provide unobstructed flow channels of the negative-pressure pathway 1405 between the rows of supports 365.

In some embodiments, the bridge 160 may comprise a port 1505 configured to fluidly couple the negative-pressure pathway 1405 to a negative pressure source and fluidly couple the instillation conduit 1410 to an instillation source. For example, the port 1505 may be located in a proximal end 1510 of the bridge 160, and the negative-pressure pathway 1405 and the instillation conduit 1410 comprising the instillation pathway may each extend from the port 1505 to approximately the aperture in the distal end 1415. Some embodiments of the port 1505 may be similar to the adapter 250.

Some embodiments of the bridge 160 may comprise a pressure-sensing pathway 1515 that extends parallel to the negative-pressure pathway 1405. In some embodiments, the pressure-sensing pathway 1515 may be similar to the first pathway 340 or the second pathway 345 in FIG. 3A or the first fluid conductor 1115 or second fluid conductor 1120 in FIG. 11A. The pressure-sensing pathway 1515 may be pneumatically isolated from the negative-pressure pathway 1405 and the instillation pathway 1410 except through the aperture in the distal end 1415 of the bridge 160. For example, the port 1505 may further be configured to fluidly couple the pressure-sensing pathway 1515 to a pressure sensor, and the pressure-sensing pathway 1515 may extend from the port 1505 to approximately the aperture. In some embodiments, the pressure-sensing pathway 1515 may be formed by a barrier 1105 between the inner surface of the first layer 315 and the inner surface of the second layer 320 of the negative-pressure pathway 1405, for example forming the pressure-sensing pathway 1515 within the enclosed space of the negative-pressure pathway 1405. In some embodiments, a plurality of pressure-pathway supports 1520 may be located in the pressure sensing pathway. In FIG. 15A, for example, the plurality of pressure-pathway supports 1520 in the pressure-sensing pathway 1515 may be smaller than the plurality of supports 365 in the negative-pressure pathway 1405, and may be configured to support the pressure-sensing pathway 1515 against collapse.

Figure 15B:
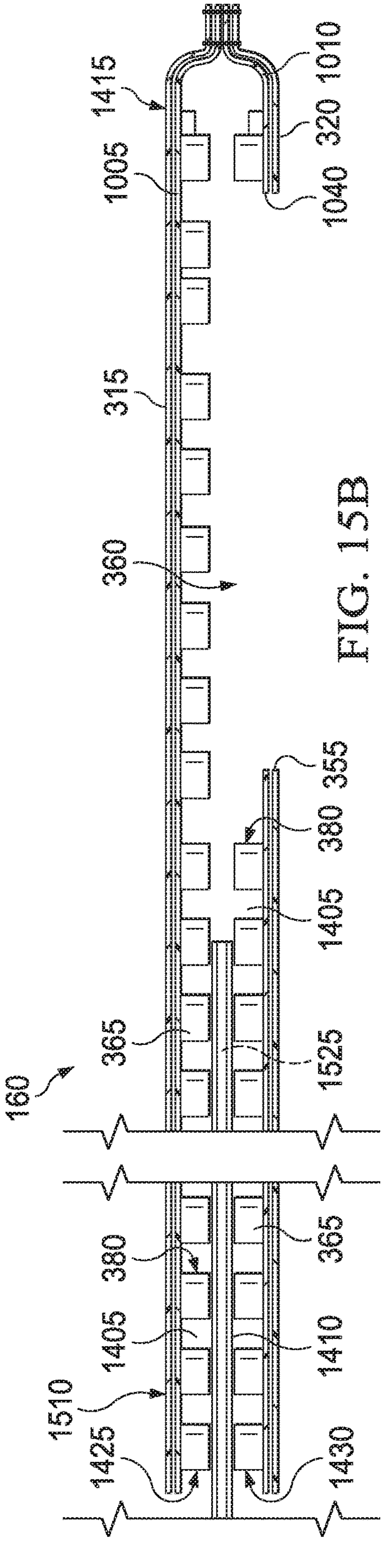
FIG. 15B is a schematic longitudinal cross-section slice view of the bridge of FIG. 15A.

FIG. 15B is a schematic longitudinal cross-section slice view of the bridge 160 of FIG. 15A, illustrating additional details that may be associated with some embodiments. FIG. 15B illustrates the distal end 1415 of the bridge 160 and shows the instillation conduit 1410 located within the negative-pressure pathway 1405 and extending longitudinally in the negative-pressure pathway 1405. For example, the instillation conduit 1410 may extend substantially the length of the negative-pressure pathway 1405. The instillation conduit 1410 may extend from the port to the recessed space 360 or aperture 355 in some embodiments. The instillation conduit 1410 may form an instillation pathway 1525, for example with the instillation pathway 1525 in FIG. 15B located within the instillation conduit 1410. The instillation pathway 1525 may be configured to allow flow of instillation fluid during the instillation process. As shown in FIG. 15B, the plurality of supports 365 of the bridge 160 may comprise a first plurality of supports 1425 and a second plurality of supports 1430. The instillation pathway 1525 may be located between the first plurality of supports 1425 and the second plurality of supports 1430. In some embodiments, the first plurality of support 1425 may be opposingly aligned with the second plurality of supports 1430, for example to support the negative-pressure pathway 1405. The instillation pathway 1525 may be located between at least a portion of the first plurality of supports 1425 and the second plurality of supports 1430. In some embodiments, the first spacer layer 1005 may comprise the first plurality of supports 1425, and the second spacer layer 1010 may comprise the second plurality of supports 1430. For example, the first plurality of supports 1425 may extend inward from an inner surface of the first spacer layer 1005, and the second plurality of supports 1430 may extend inward from an inner surface of the second spacer layer 1010. The first plurality of supports 1425 and the second plurality of supports 1430 may each be aligned into longitudinally extending rows. For example, the first plurality of supports 1425 may be aligned into rows that match the rows of the second plurality of supports 1430, so that the first plurality of supports 1425 may be opposingly aligned and stacked with the second plurality of supports 1430.

In some embodiments, the instillation pathway 1525 may be configured to fluidly communicate with the negative-pressure pathway 1405 through the recessed space 360 in the negative-pressure pathway 1405. In some embodiments, the recessed space 360 may be configured to fluidly communicate with the ambient environment through the aperture 355 in the second layer. For example, the instillation pathway 1525 may be configured to interact with the negative-pressure pathway 1405 so that at least a portion of the instillation pathway 1525 collapses upon application of negative pressure to the negative-pressure pathway 1405. In some embodiments, the negative-pressure pathway 1405 and the instillation pathway 1525 may each comprise enclosed conduits configured for fluid transfer from one end to another end of the bridge 160. For example, the negative-pressure pathway 1405 and the instillation pathway 1525 may each comprise a separate enclosed space for fluid flow from the proximal end 1510 to the distal end 1415 of the bridge 160. In some embodiments, the supports 365 may be located within the enclosed space of the negative-pressure pathway 1405.

In some embodiments, the negative-pressure pathway 1405 and the instillation pathway 1525 may be pneumatically isolated from each other and/or the ambient environment except through the recessed space 360 and/or the aperture 355 in the distal end 1415 of the bridge 160. For example, the instillation pathway 1525 may be pneumatically isolated from the negative-pressure pathway 1405 except through the recessed space 360 in the distal end of the negative-pressure pathway 1405. In some embodiments, the instillation pathway 1525 may interact with the negative-pressure pathway 1405 pneumatically through the recessed space 360, thereby providing fluid communication. In the example of FIG. 15B, the distal end of the instillation pathway 1525 may be in fluid communication with the negative-pressure pathway 1405 through the recessed space 360, allowing any negative pressure that is applied to the negative-pressure pathway 1405 to also operate on the instillation pathway 1525 in a way that may cause at least a portion of the instillation pathway 1525 to collapse. For example, the recessed space 360 in the distal end of the negative-pressure pathway 1405 may be in fluid communication with the open distal end of the instillation pathway 1525. In some embodiments, the recessed space 360 may comprise the aperture 355. For example, the recessed space 360 in FIG. 15B may comprise the aperture 355 in conjunction with the second aperture 1040. In some embodiments, the aperture 355 may be configured to allow fluid communication between the recessed space 360 and the ambient environment. In some embodiments, the negative-pressure pathway 1405 and/or the instillation pathway 1525 may be in fluid communication with the ambient environment through the aperture 355. For example, the negative-pressure pathway 1405 and the instillation pathway 1525 may be pneumatically isolated from the ambient environment except through the aperture 355 and/or the second aperture 1040.

In some embodiments, the instillation pathway 1525 and the negative-pressure pathway 1405 may interact through contact of the supports 365 of the negative-pressure pathway 1405 with the instillation pathway 1525. For example, as negative-pressure is applied to the negative-pressure pathway 1405, the supports 365 may clamp down on the instillation pathway 1525, which may collapse at least a portion of the instillation pathway 1525. In some embodiments, at least a portion of the instillation pathway 1525 may collapse across the width of the instillation pathway 1525 upon application of negative pressure, for example due to clamping of supports and/or suction within the instillation pathway from negative-pressure.

In some embodiments, collapse of the instillation pathway 1525 may be sufficient to close the instillation pathway 1525, substantially preventing fluid flow through the instillation pathway 1525. For example, collapse of the instillation pathway 1525 may operate to prevent siphoning of instillation fluid when negative pressure is applied to the negative-pressure pathway 1405. In some embodiments, the instillation pathway 1525 may comprise a collapsible conduit, for example configured to interact with the negative-pressure pathway 1405 so that the collapsible instillation conduit 1410 collapses along its entire length upon application of negative pressure to the negative-pressure pathway 1405. For example, the instillation pathway 1525 in FIG. 15B may comprise no internal support, such that there may be no instillation supports within the instillation pathway 1525. Instead, the instillation pathway 1525 may be configured to collapse, for example when there is no fluid pressure within the instillation pathway 1525 and/or when the instillation pathway 1525 experiences negative pressure. By way of example, the collapsible instillation conduit 1410 may comprise a thin polyurethane film tube, which may have a material thickness of the polyurethane material from approximately 30 to 80 micron.

In some embodiments, each of the supports 365 of the first spacer layer 1005 may comprise a hollow standoff 380, and the first layer 315 may be sealed to the first spacer layer 1005 to maintain internal pressure within the plurality of hollow standoffs 380. In some embodiments, each of the plurality of supports 365 may comprise a standoff 380 and a base, with the standoff having a closed surface extending away from the base. Similarly, each of the second plurality of supports 1430 of the second spacer layer 1010 may comprise a hollow standoff 380, and the second layer 320 may be sealed to the second spacer layer 1010 to maintain internal pressure within the standoffs 380 of the second plurality of supports 1430. In some embodiments, the first layer 315 and/or the second layer 320 may comprise a polyurethane film from approximately 80 to 120 micron in thickness. In some embodiments, the first spacer layer 1005 and/or the second spacer layer 1010 may be thermoformed structures with integral open pathway features, such as supports 365. In some embodiments, the thermoformed structures may comprise thermoplastic polyurethane, for example thermoplastic polyurethane film from approximately 200 to 500 microns in thickness. The supports 365 may comprise a variety of shapes, for example substantially circular, hexagonal, oval, triangular, and/or square. In some embodiments, the standoffs 380 may each comprise a blister, a bubble, or a cell. In some embodiments, all of the standoffs 380 may be similarly sized and/or shaped. In some embodiments, the supports 365 may comprise a diameter from approximately two to four millimeters and/or a height from approximately two to five millimeters.

In some embodiments, the first plurality of supports 1425 may be aligned with and in stacked relationship with the second plurality of supports 1430, and the instillation pathway 1525 may be located between at least some of the stacked first plurality of supports 1425 and second plurality of supports 1430. In some embodiments, the first plurality of supports 1425 and the second plurality of supports 1430 may work together to jointly support the negative-pressure pathway 1405. For example, the first plurality of supports 1425 may be stacked and opposingly aligned with the second plurality of supports 1430. In some embodiments, the first spacer layer 1005 and second spacer layer 1010 may be stacked, with the instillation pathway 1525 sandwiched therebetween. For example, the first plurality of supports 1425 of the first spacer layer 1005 may be stacked with the second plurality of supports 1430 of the second spacer layer 1010, with supporting faces substantially parallel and/or contacting. In some embodiments, the first plurality of supports 1425 and the second plurality of supports 1430 may jointly support the negative-pressure pathway to maintain an open pathway with a height substantially equal to the height of one of the first plurality of supports 1425 and one of the second plurality of supports 1430 taken together (e.g.

stacked to provide a cumulative height). In some embodiments, the instillation pathway 1525 may be located between and in stacked relationship with at least some of the first plurality of supports 1425 and at least some of the second plurality of supports 1430, for at least a portion of the negative-pressure pathway 1405.

Figure 15C:
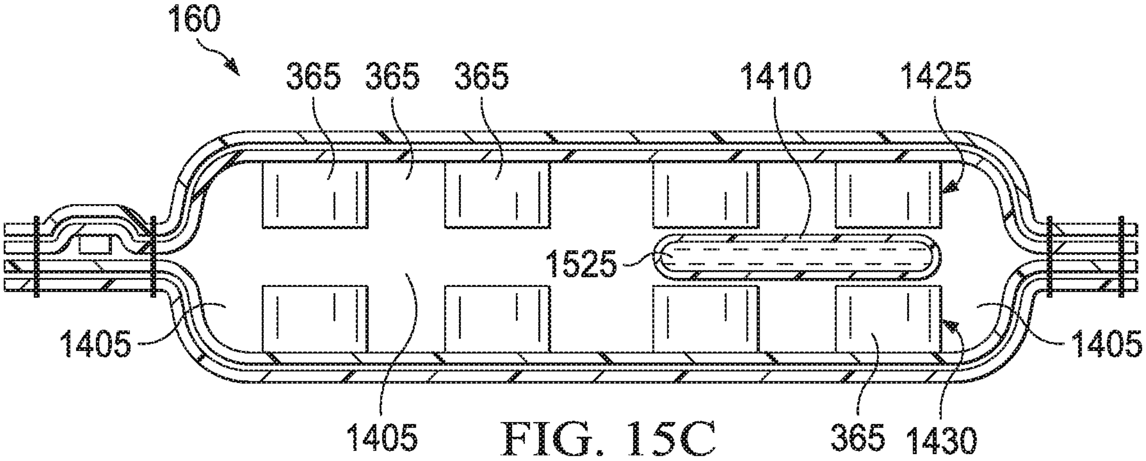
FIG. 15C is a schematic cross-section view of the bridge of FIG. 15A, illustrating instillation when negative pressure is off.

FIG. 15C is a schematic horizontal cross-section view of the bridge 160 of FIG. 15A, illustrating additional details that may be associated with some embodiments. Some embodiments of the negative-pressure pathway 1405 may be similar to the third pathway 350 of FIG. 3A and/or the third fluid conductor 1125 of FIG. 11A. In some embodiments, the negative-pressure pathway 1405 may be configured to maintain an open pathway despite application of negative-pressure and/or external compression loading. In some embodiments, the plurality of supports 365 are configured to maintain the negative-pressure pathway 1405 as an open pathway, for example allowing negative pressure to be applied to a tissue site through the negative-pressure pathway even when the negative-pressure pathway 1405 experiences compressive loads. For example, the negative-pressure pathway 1405 may be maintained in an open position, without collapsing in a way that may close off the negative-pressure pathway 1405, even if the patient is lying atop the bridge 160. In some embodiments, the instillation pathway 1525 may be configured with respect to the negative-pressure pathway 1405 so that the supports 365 of the negative-pressure pathway 1405 also ensure that the instillation pathway 1525 remains at least partially open for instillation. For example, the instillation pathway 1525 within the instillation conduit 1410 may be located with respect to the supports 365 of the negative-pressure pathway 1405 so that at least a portion of the instillation pathway 1525 may be maintained as open between the supports 365 during instillation, allowing instillation fluid flow through the instillation pathway 1525 even when the patient is lying atop the bridge 160. In some embodiments, the plurality of supports 365 may be configured to support the negative-pressure pathway 1405 substantially along its entire length and/or width. For example, the supports 365 may be co-extensive with the negative-pressure pathway 1405. In some embodiments, the supports 365 may be sealed to maintain an internal pressure. For example, the supports 365 may be maintained at a pressure at or above atmospheric pressure, which may aid in resisting compression or collapse.

As shown in in FIG. 15C, the instillation pathway 1525 may span a portion, but not all, of the width of the negative-pressure pathway 1405. In some embodiments, at least a portion of the first plurality of supports 1425 may be located on the opposite side of the instillation pathway 1410 from at least a portion of the second plurality of supports 1430. The remainder of the negative-pressure pathway 1405 may comprise another portion of the first plurality of supports 1425 stacked directly adjacent to another portion of the second plurality of supports 1430 (e.g. without the instillation pathway 1410 therebetween). For example, the instillation pathway 1525 may span the widths of two or more supports 365. In some embodiments, at least a portion of the instillation pathway 1525 may span one or more spaces between two or more rows of supports 365. In some embodiments, the instillation pathway 1525 may span substantially the entire width of the negative-pressure pathway 1405. In the example of FIG. 15C, the instillation pathway 1525 may be located within an expandable conduit. For example, the conduit may typically be substantially flat when no instillation fluid is located within it, but may expand out to open when instillation fluid flow is present.

FIG. 15C illustrates instillation through the instillation pathway 1525 when there is no compression applied to the bridge 160. The instillation pathway 1525 in FIG. 15C may expand and/or open during instillation fluid flow, for example pushing the first plurality of supports 1425 away from the second plurality of supports 1430. Instillation fluid may then be pumped through the instillation pathway 1525.

Figure 15D:
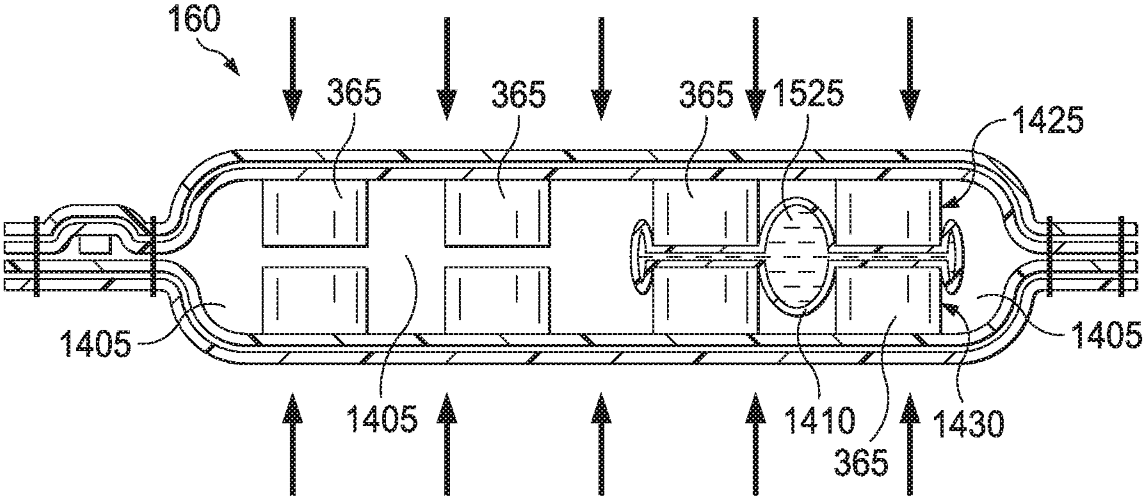
FIG. 15D is a schematic cross-section view of the bridge of FIG. 15A, illustrating instillation when the bridge is under compression.

FIG. 15D is a schematic cross-section view of the bridge 160 of FIG. 15A, illustrating additional details that may be associated with some embodiments. In the example of FIG. 15D, the instillation pathway 1525 may be configured to expand and/or open when the bridge 160 is under compression, to substantially fill spaces between the rows of supports 365 during instillation. This configuration may allow instillation even when the bridge 160 is under compression, ensuring that an open instillation pathway 1525 may be maintained despite compression. For example, the tube-like conduit of the instillation pathway 1525 may interact with the plurality of supports 365 so that the instillation conduit 1410 expands and/or opens into the spaces between the rows of supports 365, thereby allowing longitudinal fluid flow through at least a portion of the instillation pathway 1525 even when the bridge 160 is under sufficient compression so that the first plurality of supports 1425 and the second plurality of supports 1430 are in close proximity (e.g. substantially contacting). In some embodiments, the portions of the instillation pathway 1525 between the first plurality of supports 1425 and the second plurality of supports 1430 might be compressed flat between opposing supports 365 during compression, but the portions of the instillation pathway 1525 between the rows of supports 365 may expand and/or open to substantially fill longitudinally extending spaces between the rows of supports 365 during instillation.

Figure 15E:
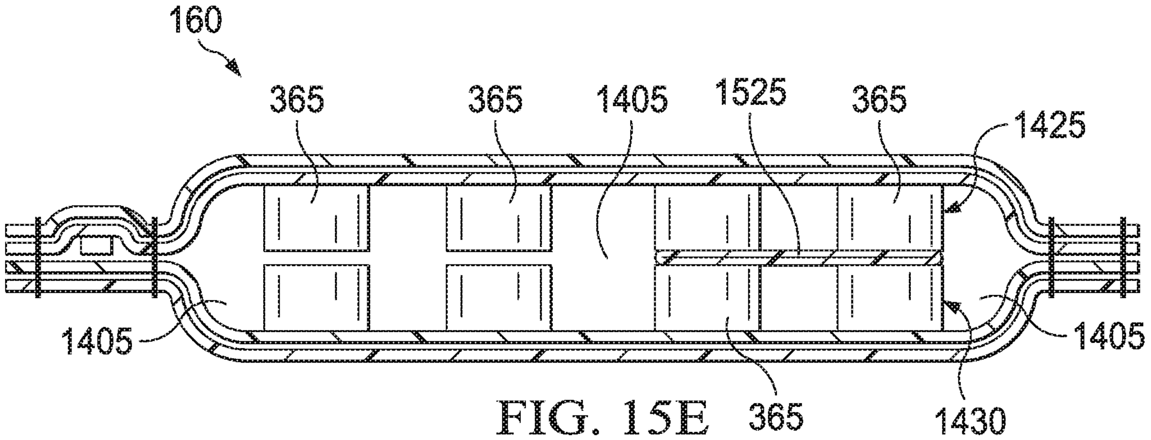
FIG. 15E is a schematic cross-section view of the bridge of FIG. 15A, illustrating negative pressure application when instillation is off.

FIG. 15E is a schematic cross-section view of the bridge 160 of FIG. 15A, illustrating additional details that may be associated with some embodiments. In the example of FIG. 15E, instillation is not occurring. Rather, negative pressure is being applied to the negative-pressure pathway 1405. The instillation pathway 1525 may collapse to be substantially flat and/or closed during negative-pressure therapy. For example, the portions of the instillation pathway 1525 clamped between opposingly aligned supports 365 may be substantially flat, and the portions of the instillation pathway 1525 spanning the spaces between the opposingly aligned supports 365 may also be drawn substantially flat due to negative pressure. For example, communication of negative pressure into the instillation pathway 1525 from the negative-pressure pathway 1405 during negative-pressure therapy may flatten the instillation pathway 1525. This configuration may maximize flow capability through the negative-pressure pathway 1405 during negative-pressure therapy by minimizing the size of the instillation pathway 1525 at such time. During negative-pressure therapy, fluid may be removed through the longitudinally extending rows between the plurality of supports 365, with only minor flat-profile disruption in spaces spanned by the flattened instillation pathway 1525. In some embodiments, the flat configuration of the instillation pathway 1525 during negative-pressure therapy may result in substantially no blockage of flow through the negative-pressure pathway 1405 during fluid removal. This may be true whether or not external compression is applied to the bridge 160. During negative-pressure therapy in some embodiments, the first plurality of supports 1425 may be drawn towards the second plurality of supports 1430, so that the supporting faces substantially contact. For example, some supporting faces of supports 365 may directly contact opposing support faces, while some supports 365 may only be separated from opposingly aligned supports 365 by a substantially flat instillation pathway 1525.

Figure 16:
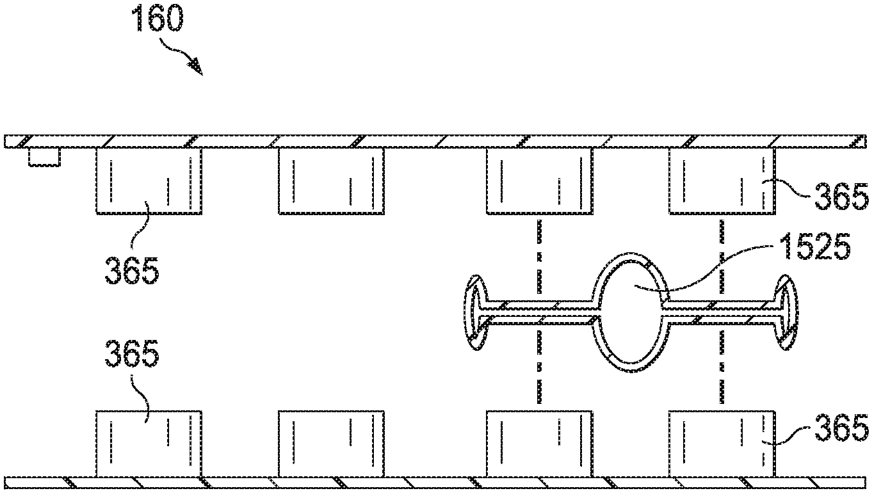
FIG. 16 is a partial assembly schematic view illustrating another example of an instillation conduit.

FIG. 16 is a partial assembly schematic view of another, similar bridge 160, illustrating additional details that may be associated with some embodiments. In some embodiments, the instillation pathway 1525 may have a shape matching the supports 365 spanning at least a portion of the width of the negative-pressure pathway 1405. In some embodiments, the instillation pathway 1525 may have a corrugated shape, for example flat where interacting with a row of supports 365, and non-flat (e.g. shaped or capable of expanding and/or opening to allow fluid flow) in spaces between rows of supports 365. Shaped instillation pathway embodiments may still be configured to be collapsible, however, in order to prevent siphoning of fluid during negative-pressure therapy. In some embodiments, the instillation pathway 1525 may comprise a plurality of collapsible longitudinal conduits located between the supports 365 in the enclosed space of the negative-pressure pathway 1405.

In some embodiments of the bridge 160, one or more of the layers may comprise or consist essentially of foam, such as closed-cell foam. In some embodiments, the plurality of supports 365 may comprise or consist essentially of foam, such as closed-cell foam. In some embodiments, the one or more support or spacer layers (e.g. having a plurality of supports extending from an inner surface) may comprise or consist essentially of foam, such as closed-cell foam. Some embodiments may comprise foam, such as closed-cell foam, and polymer film. Some embodiments may be formed entirely of foam, such as closed-cell foam.

Figure 17A:
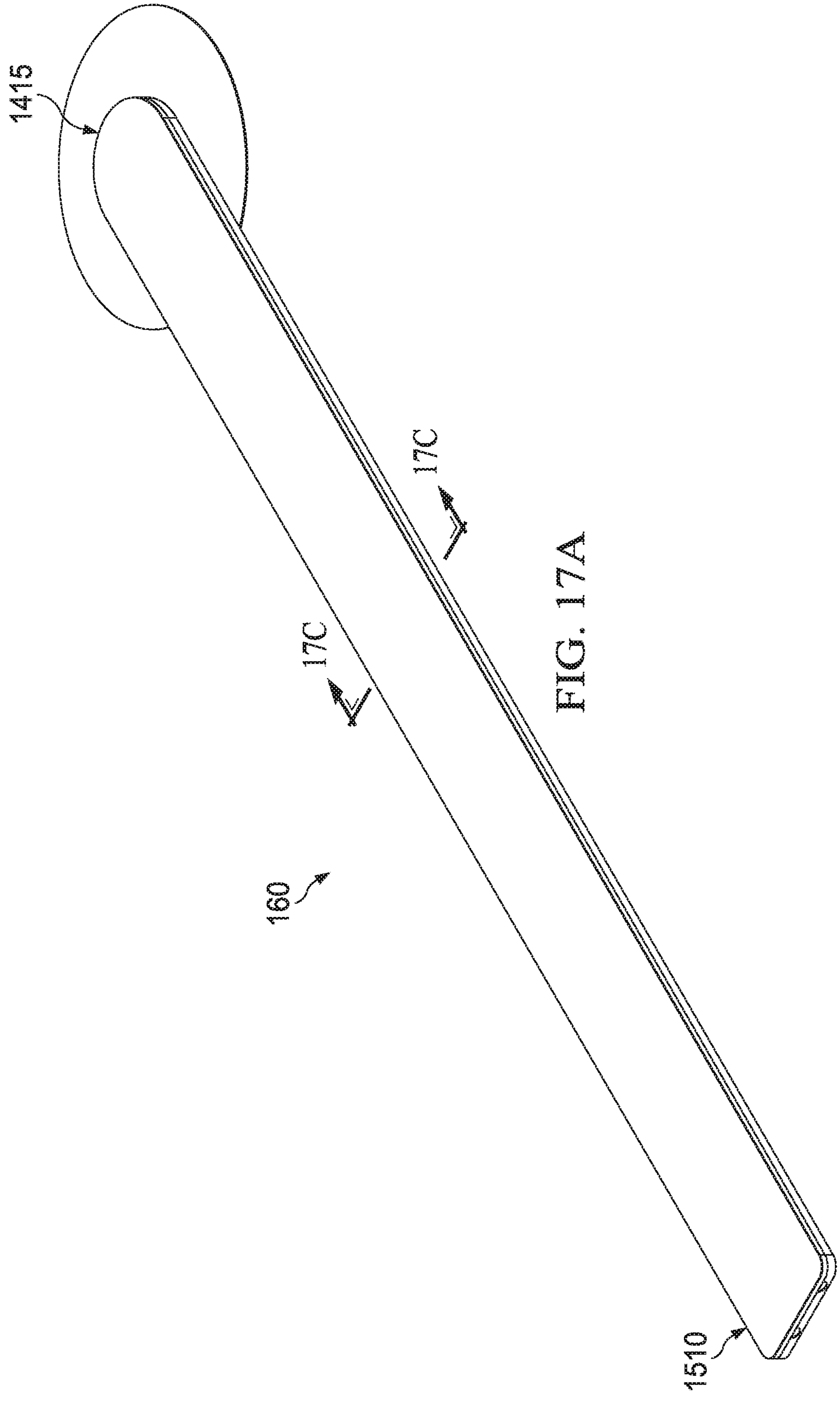
FIG. 17A is an isometric view of another bridge embodiment.

FIG. 17A is an isometric view of another exemplary bridge 160, illustrating additional details that may be associated with some embodiments. The illustrative bridge 160 shown in FIG. 17A may comprise one or more layers formed of foam, such as closed-cell foam. The bridge 160 may have a low-profile in some embodiments. In some embodiments, the bridge 160 may be relatively soft, for example without hard points that might cause patient discomfort. In some embodiments, the bridge 160 may have an elongate form, with the distal end 1415 configured for interaction with the tissue site and/or dressing, and the proximal end 1510 spaced longitudinally from the distal end 1415. The bridge 160 may operate as the fluid communicating dressing interface in some embodiments.

Figure 17B:
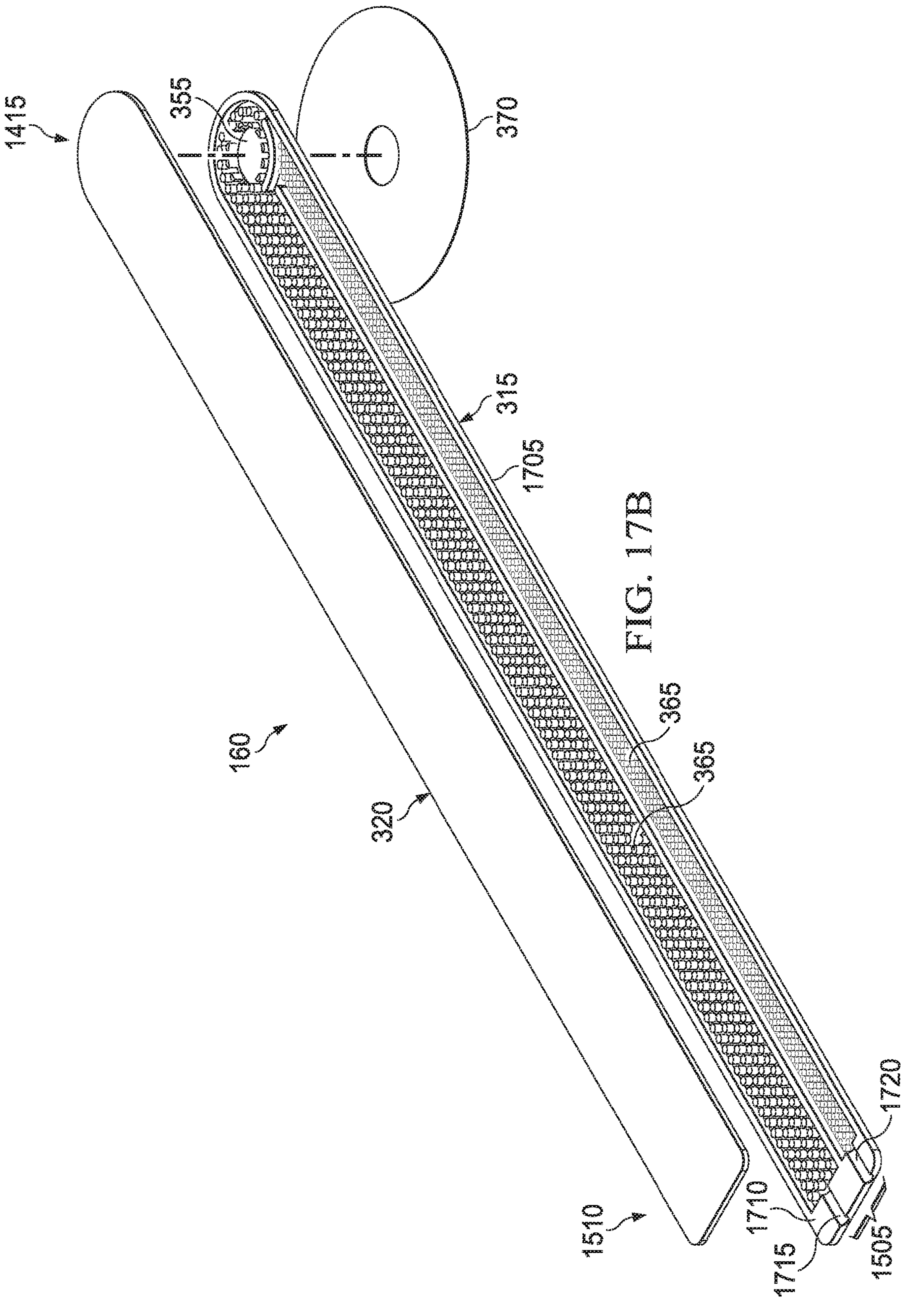
FIG. 17B is an assembly view of the bridge of FIG. 17A.

FIG. 17B is an assembly view of the bridge 160 of FIG. 17A, illustrating additional details that may be associated with some embodiments. In some embodiments, the bridge 160 may comprise the first layer 315 and the second layer 320, which may be stacked and coupled together about a perimeter to define an enclosed space. In some embodiments, the first layer 315 may comprise an outer surface 1705, an inner surface 1710, and a plurality of supports 365 extending from the inner surface 1710, and the first layer 315 may be formed of foam. For example, the first layer 315 may comprise a spacer layer of foam, having a plurality of supports extending from the inner surface. In some embodiments, the first layer 315 may be formed entirely of closed-cell foam. The second layer 320 may be disposed in stacked relationship with the first layer 315 and oriented to be adjacent to and/or covering the plurality of supports 365. In some embodiments, the enclosed space between the first layer 315 and the second layer 320 may form at least one fluid pathway. Some embodiments may have an aperture 355, for example in the distal end 1415 of the at least one fluid pathway, configured to provide fluid communication between the at least one fluid pathway and the dressing or tissue site. Some embodiments may have a port 1505, for example in the proximal end 1510 of the at least one fluid pathway, configured to provide fluid communication between the at least one fluid pathway and a negative-pressure source. In some embodiments, the at least one fluid pathway may extend and provide fluid communication between the port 1505 and the aperture 355.

In some embodiments, the port 1505 may comprise one or more openings configured to interface with the negative-pressure source, the instillation source, and/or the pressure sensor. For example, in FIG. 17B, the port 1505 may comprise a first port opening 1715 and a second port opening 1720, with each opening configured to provide fluid communication to (e.g. interface with) one of the fluid pathways. In some embodiments, the port openings may be located in the proximal end 1510, for example each extending longitudinally inward through at least a portion of the first layer 315 to the respective fluid pathway.

Some embodiments may also comprise a recessed space (not shown here) configured to provide fluid communication between the one or more fluid pathway and the aperture 355. In some embodiments with a plurality of fluid pathways, the recessed space may fluidly couple the fluid pathways (e.g. at their distal end). In some embodiments, the recessed space may comprise a portion of the one or more fluid pathway without supports that is located in proximity to and/or fluid communication with the aperture.

In some embodiments, plurality of supports 365 may be co-extensive with at least one fluid pathway. In FIG. 17B, the plurality of supports 365 may be co-extensive with both the first pathway and the second pathway, for example supporting the fluid pathways for substantially their entire length and width. In some embodiments, the plurality of supports 365 may be configured to support the at least one fluid pathway to resist collapse under negative pressure (e.g. of negative-pressure therapy) and/or under compression from a patient's body weight (e.g. if the patient lies atop the bridge). The supports 365 may be configured to maintain an open pathway. Except for the supports 365, the one or more fluid pathway in some embodiments may be open.

Some embodiments may comprise the affixation surface 370 located around the aperture 355, for example with adhesive configured to attach the bridge 160 to the dressing. In some embodiments, the affixation surface 370 may comprise a flat adhesive surface. In some embodiments, the affixation surface 370 may be wider than the remainder of the bridge 160. In some embodiments, the affixation surface 370 may comprise an adhesive drape ring, such as a ring-shaped double-sided adhesive film, with the tissue-facing side of the affixation surface 370 being coated with an adhesive for attachment to the dressing, and the opposite side being coupled to the distal end around the aperture 355 (e.g. by adhesive, heat seal, or welding).

Figure 17C:
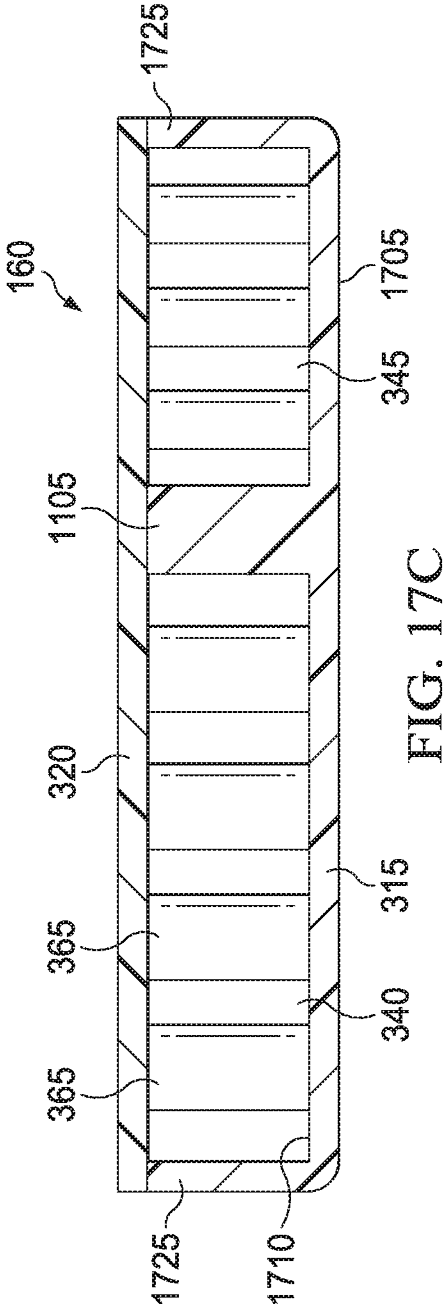
FIG. 17C is a cross-section view of the bridge of FIG. 17A.

FIG. 17C is a cross-section view of the bridge of FIG. 17A, illustrating additional details that may be associated with some embodiments. In some embodiments, each of the plurality of supports 365 may have a height that is substantially the same for all of the plurality of supports (e.g. all of the plurality of supports may have an identical height). In some embodiments, the first layer 315 or the second layer 320 may comprise a perimeter wall 1725 having a height equal to the height of the plurality of supports 365. For example, in FIG. 17C, the first layer 315 may comprise the perimeter wall 1725, which may extend substantially around the perimeter of the bridge 160, and the perimeter wall 1725 and the plurality of supports 365 may be substantially identical in height.

Some embodiments may comprise a barrier 1105 between the inner surface 1710 of the first layer 315 and the second layer 320. The barrier 1105 may divide the enclosed space between the first layer 315 and the second layer 320 into two or more fluid pathways. For example, in FIG. 17C, the barrier 1105 may form the first pathway 340 and the second pathway 345, which may each extend longitudinally (e.g. from the port to the recessed space), side-by-side, and in parallel. In some embodiments, the fluid pathways may be pneumatically isolated (e.g. by the barrier 1105 therebetween) except through the recessed space. For example, the barrier 1105 may extend from the port to the recessed space. In some embodiments, the barrier 1105 may have a height identical to that of the supports 365 and the perimeter walls 1725. In some embodiments, the perimeter wall 1725, the barrier 1105, and the supports 365 may all contact the second layer 320. In some embodiments, the second layer 320 may be coupled to the first layer 315 about the perimeter (e.g. perimeter walls 1725) and the barrier 1105. In some embodiments, the second layer 320 may be coupled to the plurality of supports 365. In some embodiments, the second layer 320 may be a substantially flat sheet, for example with no supports projecting outward from a surface.

In some embodiments, at least the first pathway 340 may be supported by the plurality of supports 365 to resist collapse under negative pressure (e.g. of negative-pressure therapy). In FIG. 17C, both pathways may be supported. In some embodiments, the first pathway 340 may be configured to be in fluid communication with a negative-pressure source through the port (e.g. configured to be a negative-pressure pathway), and the plurality of supports 365 may be configure to prevent collapse of the first pathway 340 when negative pressure is applied from the negative-pressure source. In some embodiments, the second pathway 345 may be configured to be in fluid communication with an instillation source or a pressure sensor through the port (e.g. configured to be an instillation pathway or a pressure-sensing pathway). In some embodiments, the plurality of supports 365 may be configured to also support the second pathway 345. In some embodiments, the supports in the first pathway 340 and the supports in the second pathway 345 may be substantially identical, while in other embodiments the supports in the first pathway 340 may be configured to be more supportive (e.g. larger diameter) than the supports in the second pathway 345. In some embodiments, the plurality of supports 365 may each have a tapered shape (not shown), with base portion wider than tip portion. In some embodiments, both the first pathway 340 and the second pathway 345 may be configured to be in fluid communication with the tissue site through the aperture.

In some embodiments, the second layer 320 may comprise or consist essentially of (e.g. be formed of) a film. For example, the second layer 320 may comprise or consist essentially of polyethylene film. In other embodiments, the second layer 320 may be formed of foam, such as closed-cell foam. In some embodiments, the closed-cell foam of the first layer 315 and/or the second layer 320 may be cross-linked. In some embodiments, the first layer 315 and the second layer 320 may be formed of the same closed-cell foam. In some embodiments, the first layer 315 and/or the second layer 320 may each be formed of one of the following closed-cell foams: ethylene-vinyl acetate (EVA) foam; cross-linked EVA foam with a density of 40-100 kg/$m^3$; cross-linked polyethylene foam; cross-linked ethylene copolymer foam; ethyl methyl acrylate (EMA) copolymer foam; cross-linked EMA copolymer foam; AZOTE foams by Zotefoams plc in Croydon, UK such as EVAZOTE foam (such as EV50 or VA35), SUPAZOTE foam (such as EM26), PLASTAZOTE foam (such as LD24 or LD33); and combinations thereof.

In some embodiments, the first layer 315 and the second layer 320 may be sealingly coupled together by one of the following: welding (such as heat-sealing, RF-welding, laser welding, contact/hot-plate welding, IR/radiant-heat welding) or adhesive (such as pressure-sensitive, impact, or hot melt). In some embodiments, the foam of the one or more support layers (e.g. the first layer 315, with supports 365, perimeter walls 1725, and/or one or more barriers 1105) may be formed into shape via thermoforming (such as vacuum-forming), compression molding, and/or embossing (such as roll embossing or ultrasonic embossing). In some embodiments, the entire first layer may be simultaneously formed via thermoforming, compression molding, and/or embossing of the foam. For example, the supports, perimeter walls, and one or more barriers may be formed by thermoforming, compression molding, or embossing a flat sheet of foam to create the elements on the inner surface of the first layer.

While FIGS. 17B and 17C illustrate the first layer 315 (e.g. the spacer layer) with supports 365 as the bottom or tissue-site-facing layer (e.g. with the aperture), other embodiments may be configured with the first layer as the top layer and the second layer as the bottom (e.g. tissue-site-facing) layer with the aperture. In some embodiments, both the first and the second layers may be spacer layers, each having a plurality of supports extending inward. For example, some embodiments may have a first plurality of supports extending from the inner surface of the first layer and a second plurality of supports (not shown here) extending from the inner surface of the second layer. In some embodiments, the first plurality of supports may be aligned with and in stacked relationship with the second plurality of supports. In some embodiments, the first plurality of supports may be coupled to the second plurality of supports (e.g. at contacting ends). In some embodiments, the first plurality of supports and the second plurality of supports may not be stacked. For example, the first plurality of supports and the second plurality of supports may be interleaved, with end surfaces contacting the base of the opposing layer. In some embodiments, each support may comprise a standoff of foam, extending from a foam base.

In some bridge embodiments, the first layer and the second layer may comprise mating tongue-and-groove elements (not shown) configured to assist with alignment during manufacture. In some embodiments, at least a portion of the at least one fluid pathway (e.g. the inner surface of the first and/or second layers) may be coated with an anticoagulant agent configured to reduce clotting and/or coagulation of exudate. For example, the anticoagulant agent may comprise or consist essentially of heparin. In some embodiments, at least a portion of the at least one fluid pathway (e.g. the inner surface of the first and/or second layers) may be coated with a hydrophobic surface treatment, such as a plasma coating. Some embodiments may also include an instillation pathway (not shown here, but which may be similar to the collapsible instillation pathway shown in FIG. 14), for example located within the negative pressure pathway, configured so that at least a portion of the instillation pathway collapses upon application of negative pressure to the negative-pressure pathway.

Figure 18:
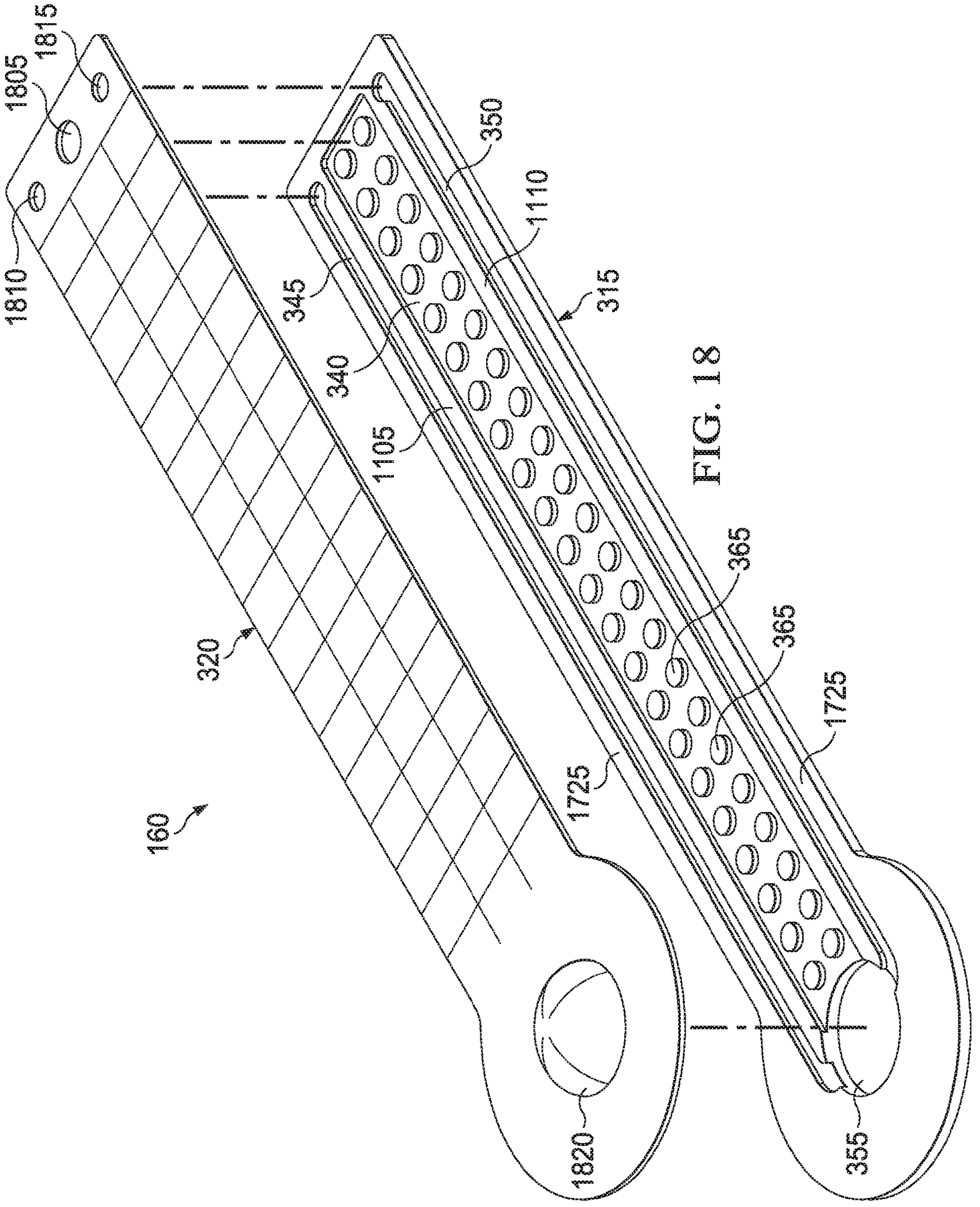
FIG. 18 is an assembly view of yet another bridge embodiment.

FIG. 18 is an assembly view of yet another exemplary bridge 160, illustrating additional details that may be associated with some embodiments. The bridge 160 of FIG. 18 may be similar to that of FIGS. 17A-C, but comprising three fluid pathways. In some embodiments, the bridge 160 may comprise two barriers, a first barrier 1105 and a second barrier 1110, configured to form three independent pathways (e.g. a first pathway 340, a second pathway 345, and a third pathway 350) which are pneumatically isolated except through their distal ends (e.g. via the recessed space and/or aperture 355). In some embodiments, the three pathways may extend side-by-side, for example substantially parallel, from the port to the distal end. In some embodiments, the plurality of supports 365 may all be located within the first pathway 340, and the second pathway 345 and the third pathway 350 may not contain any supports. In some embodiments, the second pathway 345 and/or third pathway 350 may be configured (e.g. with narrow width) so that the first barrier 1105, the second barrier 1110, and the perimeter walls 1725 adequately support the second pathway 345 and the third pathway 350 (e.g. to maintain the pathways as open and/or to prevent collapse during negative-pressure therapy and/or when a user lies atop the bridge). In some embodiments, the first pathway 340 may form the negative-pressure pathway, for example being in fluid communication with the negative-pressure source through the port; the second pathway 345 may form the instillation pathway, for example in fluid communication with the instillation fluid source through the port; and the third pathway 350 may form the pressure-sensing pathway, for example in fluid communication with the pressure sensor through the port.

In some embodiments, the port may be configured to provide separate, pneumatically-isolated fluid communication to the negative-pressure source, the instillation source, and/or the pressure sensor. For example, the port may comprise three port openings, as shown in FIG. 18, with each of the openings in fluid communication with a different one of the fluid pathways. For example, a first port opening 1805 may provide fluid communication with the first pathway 340, a second port opening 1810 may provide fluid communication with the second pathway 345, and the third port opening 1815 may provide fluid communication with the third pathway 350. In some embodiments, the port and the aperture 355 may be located in opposite layers. For example, depending on orientation of the apparatus with respect to the tissue site, the port may be located in first layer and aperture may be located in second layer; or the port may be located in second layer 320 and the aperture 355 may be located in first layer 315.

In some embodiments, the distal end 1415 may comprise a bulb element 1820 (e.g. dome-like) configured to collapse to be substantially flat with the remainder of the exterior/outer surface when experiencing negative pressure (e.g. from NP therapy), and to project outward (e.g. extending out beyond the outer surface) in the absence of negative pressure. For example, the bulb element 1820 may be formed in the distal end 1415 of the second layer 320, and may be shaped and located to cover the aperture 355 when the second layer 320 is coupled to the first layer 315. In some embodiments, the bulb element 1820 may function as a pressure indicator. For example, the bulb element 1820 may be a pressure indicator located over and/or proximate to the aperture 355 and/or in the distal end 1415. In some embodiments, the first pathway (e.g. the negative-pressure pathway) may comprise one or more additional pressure indicators, which can be distributed along the length of the fluid pathway. The pressure indicators may each be configured with a raised surface which collapses under negative pressure. For example, each pressure indicator may comprise a blister or raised channel that is configured to elastically deform. Each pressure indicator may be in fluid communication with the negative-pressure pathway, and may be configured to collapse at a threshold negative pressure. For example, the pressure indicators may each be biased against atmospheric pressure and configured to collapse at therapeutic levels of negative pressure. Without therapeutic levels of negative pressure, the pressure indicators may return to their normal expanded state (e.g. protruding from the exterior of the bridge). Delivery of negative pressure to the first fluid pathway may cause the pressure indicators to substantially collapse. A blockage in the bridge can prevent sufficient negative pressure from being delivered to all of the pressure indicators, and those pressure indicators not receiving therapeutic levels of negative pressure may not collapse or may return to their normal expanded state. In some embodiments, the pressure indicators may each comprise a spring element or other means for biasing the pressure indicator against atmospheric pressure. For example, open-cell foam, gauze, or other open-cell breathable materials may be inserted into the pressure indicators. In some embodiments, a hydrophobic filter may prevent transfer of exudate or other liquid into the pressure indicators. In some embodiments, the pressure indicators may be located in the second and/or outer layer. For example, if the second layer comprises a polymer film, the pressure indicators may each comprise a pocket of the film filled with open-cell foam and in fluid communication with the negative-pressure pathway, with the open-cell foam configured to push the pressure indicators outward in the absence of sufficient negative pressure.

In some embodiments, when the first layer is formed of closed-cell foam, the underside of the first layer 315 may be skived to remove the skin. This may reduce the surface area of foam in contact with the patient, for example to reduce perspiration buildup. In some embodiments, an external pattern (e.g. scoring or embossing or thermoformed indentations) may be disposed on the underside, and the pattern may be configured to allow airflow for comfort. For example, the pattern of indentations may form a hexagonal, square, triangular, or other tessellating pattern of 0.5 to 1.5 millimeter depressions which are spaced such that they occur with a gap of about 2-4 millimeters and cover at least a portion of the surface which will abut the patient's skin (e.g. the underside). The pattern may be configured to create an open area of approximately 50-60% of the contact area of the bridge 160 on the patient. Some embodiments may further comprise a wicking layer, such as a hydrophilic non-woven layer, attached to the underside of the first layer 315. Some embodiments may utilize micro-embossed patterns in the first layer 315 to aid with fluid transport and surface bonding.

Figure 19:
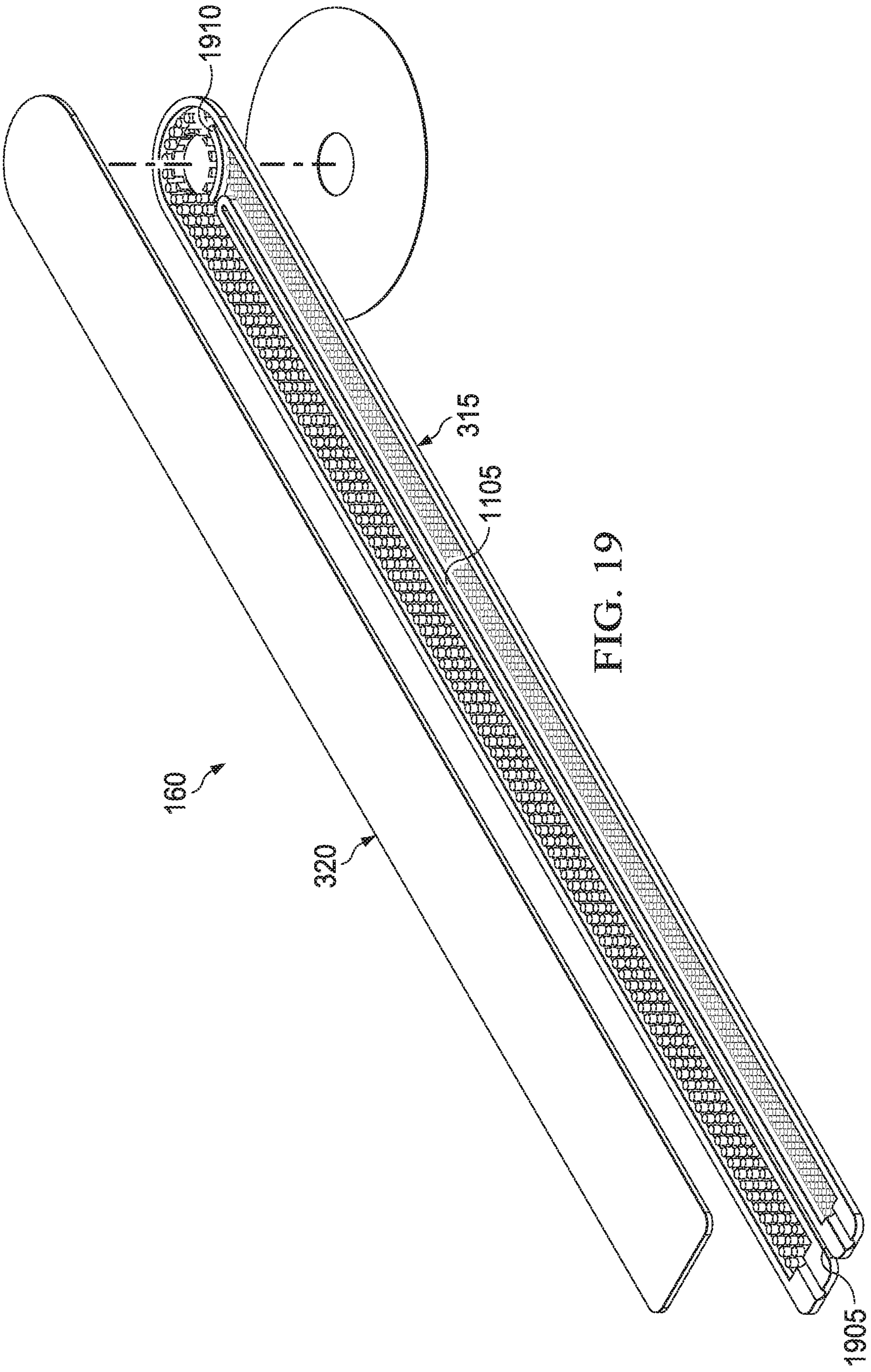
FIG. 19 is an assembly view of still another bridge embodiment.

FIG. 19 is an assembly view of still another exemplary bridge 160, illustrating additional details that may be associated with some embodiments. The bridge 160 of FIG. 19 may be similar to that of FIG. 17B, and may further comprise a slot 1905 separating the two fluid pathways. The slot 1905 may be configured to facilitate folding of the pathways with respect to each other and/or to improve flexibility in side-to-side orientation to achieve flexibility similar to a tube. The barrier 1105 (e.g. an internal wall) between the pathways may be configured to extend around the slot 1905 (e.g. around both sides of the slot and the distal end of the slot), to form the two fluid pathways separated by the slot 1905. In some embodiments, the barrier may have a height substantially equal to the height of the plurality of supports 365. For example, in FIG. 19 the supports 365 extend only from the first layer 315, and the barrier may also extend from the first layer 315 the same amount as the supports 365. Some embodiments may further comprise a baffle 1910 configured to reduce flow of fluid into the second (e.g. pressure sensing) pathway, while allowing (e.g. not significantly hindering) pressure communication to the second pathway. In other examples, a film with slits or slots may be configured to restrict liquid entry to the second pathway, while allowing for pressure communication.

Figure 20:
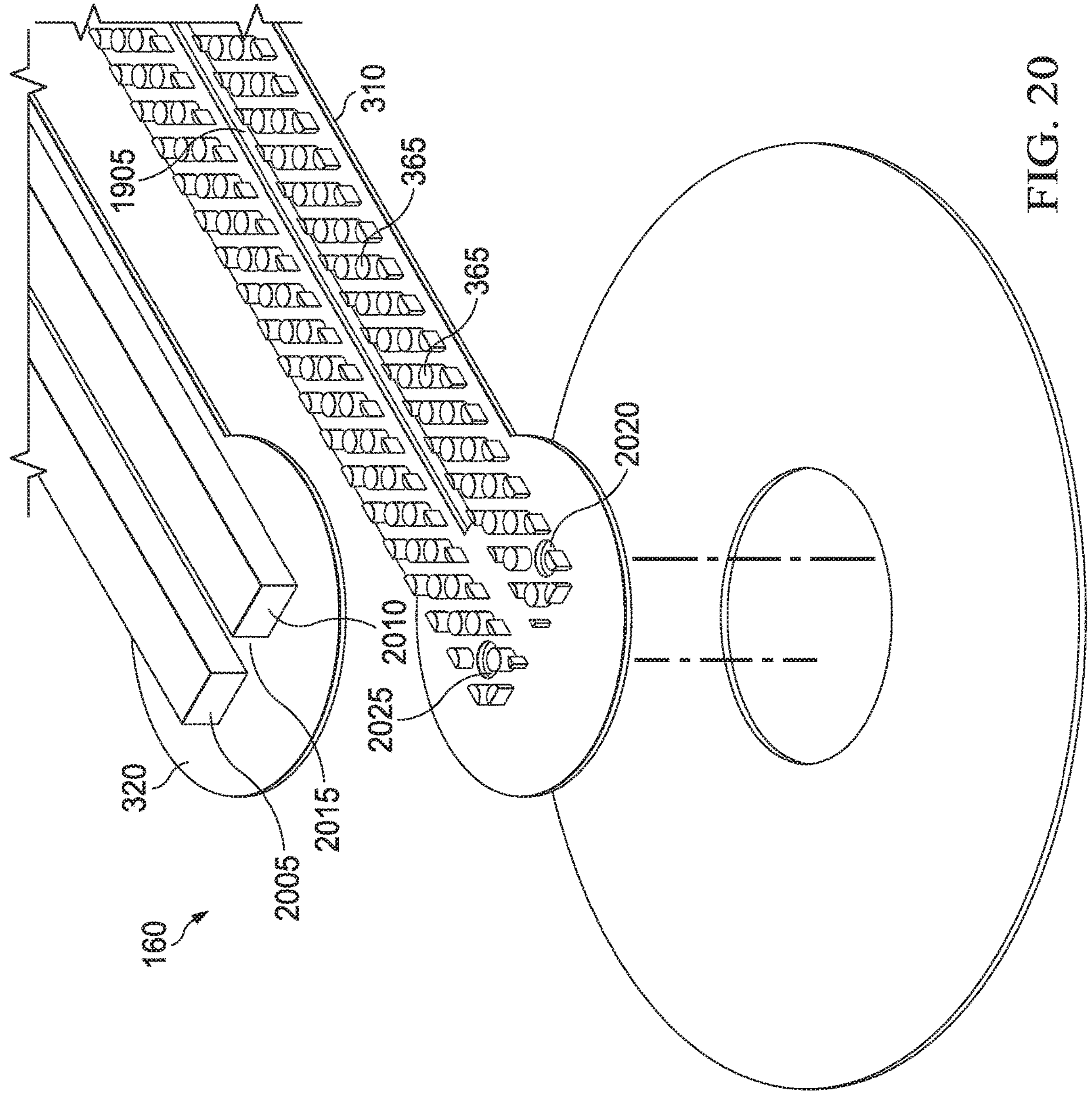
FIG. 20 is an assembly view of yet another bridge embodiment.

FIG. 20 is an assembly view of yet another exemplary bridge 160, illustrating additional details that may be associated with some embodiments. The bridge 160 of FIG. 20 may be similar to that of FIG. 19, except that the second layer 320 may not be shaped as a flat sheet. Rather, the second layer 320 may comprise two longitudinal tracks (e.g. a first track 2005 and a second track 2010), each configured to enclose one of the pathways (e.g. the supports 365 for the pathways), with a joining span 2015 between them. For example, the two longitudinal tracks may extend side-by-side from the port to the aperture. In some embodiments, each track may comprise the perimeter walls and the barriers defining the fluid pathways. In some embodiments, the second layer 320 may comprise the perimeter walls and the barriers. In some embodiments, the joining span 2015 may be configured to be sufficiently flexible and may be located with respect to the slot 1905 in the first layer 315 (e.g. spanning the slot), to enable folding of the two pathways with respect to each other. The joining span 2015 may couple the inner edge of the two tracks together. In some embodiments, the aperture may comprise a plurality of aperture openings, for example one for each fluid pathway. For example, the first aperture opening 2020 may be configured to provide fluid communication between the first fluid pathway and the dressing, and the second aperture opening 2025 may be configured to provide fluid communication between the second pathway and the dressing.

Figure 21B:
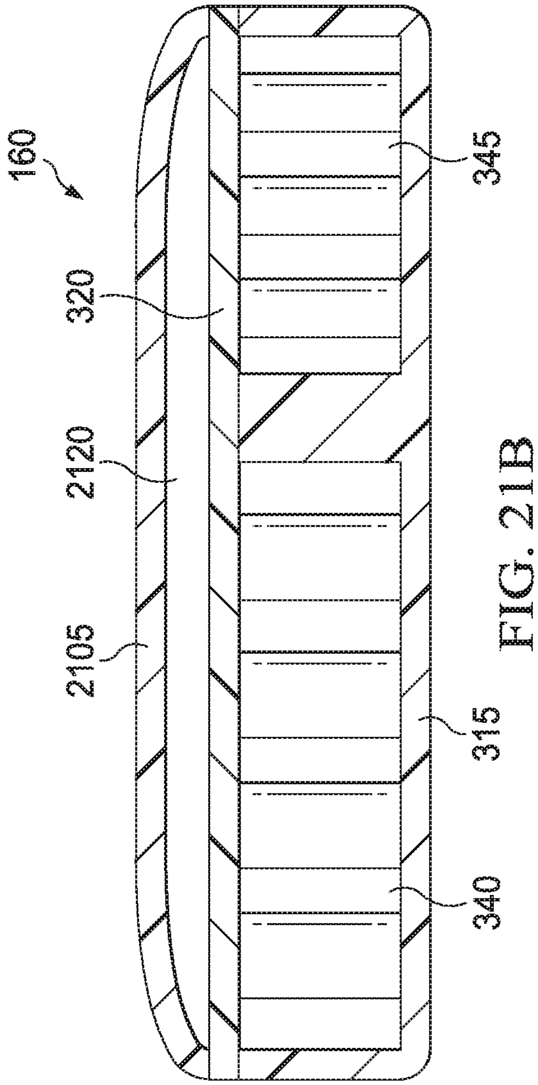
FIG. 21B is a cross-section view of the bridge embodiment of FIG. 21A.
Figure 21A:
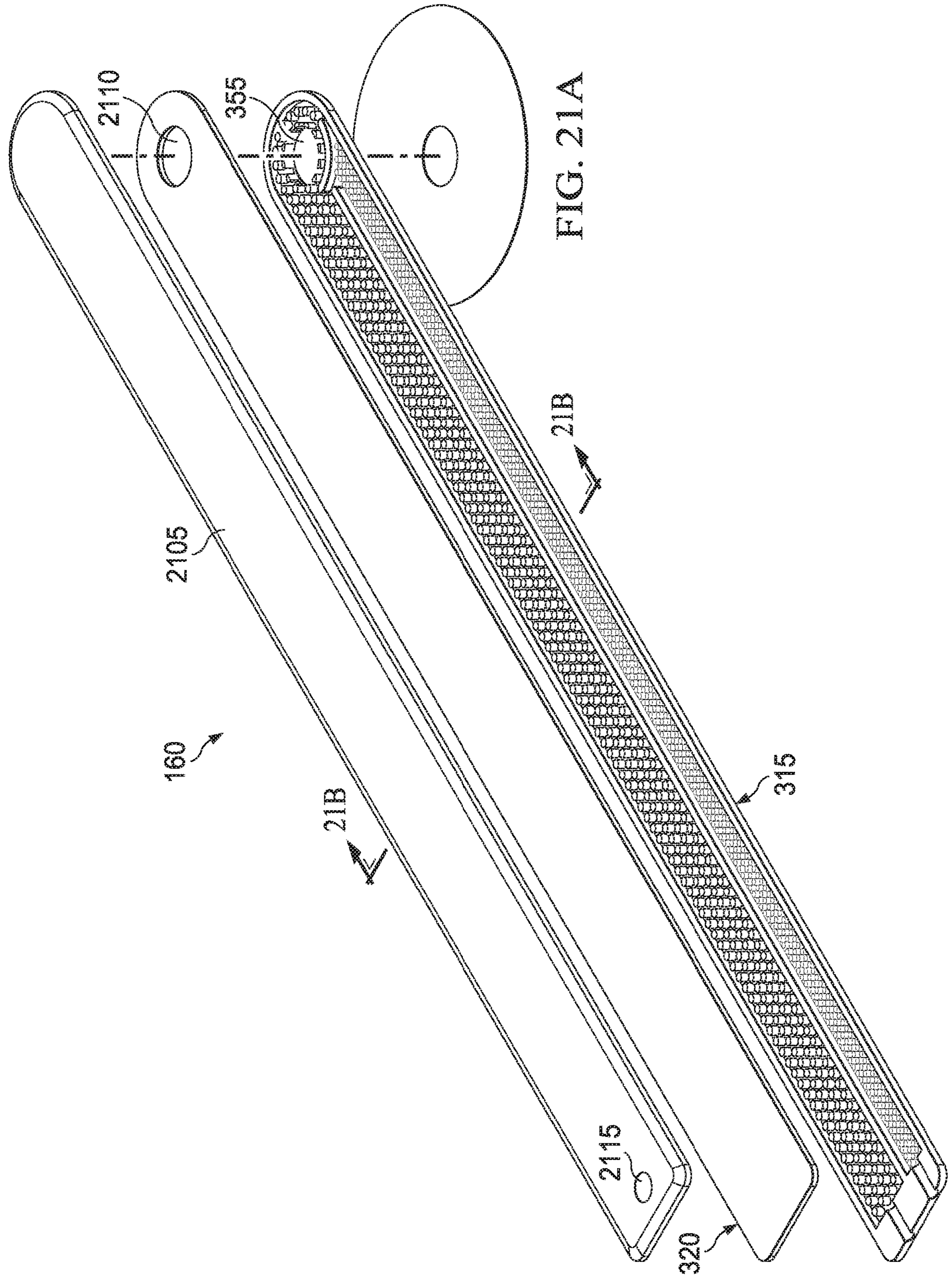
FIG. 21A is an assembly view of still another bridge embodiment.

FIG. 21A is an assembly view of still another exemplary bridge 160, illustrating additional details that may be associated with some embodiments. The bridge 160 shown in FIG. 21A may be similar to that of FIG. 17B, and may further comprise a third layer 2105. In some embodiments, the third layer 2105 may be in stacked relationship with and sealingly coupled to either the first layer 315 or the second layer 320. For example, in FIG. 21A, the third layer 2105 may be coupled to the second layer 320 about the perimeter, forming an additional fluid pathway (e.g. a third pathway) that may extend from the port to the recessed space (e.g. distal end). In some embodiments, the third fluid pathway may be pneumatically isolated from the one or more fluid pathways (e.g. the first pathway and the second pathway) except through the recessed space. In some embodiments, the recessed space (not shown here) may be formed by the aperture 355 (e.g. in the first layer 315) and/or an opening 2110 in the second layer 320 that is aligned with the aperture 355. The port may further comprise a third port opening 2115 in some embodiments, providing fluid communication with the third pathway. For example, the third port opening 2115 may be located in the distal end of the third layer 2105.

FIG. 21B is a cross-section view of the bridge 160 of FIG. 21A, illustrating additional details that may be associated with some embodiments. In some embodiments, the additional fluid pathway 2120 (e.g. the third pathway) may be in stacked relationship with the at least one fluid pathway (e.g. the first pathway 340 and second pathway 345). In some embodiments, the third layer 2105 may be a flat sheet and/or may not enclose or include any supports. The additional pathway 2120 may be configured to form the instillation pathway (e.g. in fluid communication with the instillation source through the port). This may allow the second pathway to serve as the pressure-sensing pathway (e.g. in fluid communication with the pressure sensor through the port).

In some embodiments, the third layer 2105 may comprise or consist essentially of the same materials as the second layer 320. For example, the third layer 2105 may comprise or consist essentially of closed-cell foam or polymer film. In some embodiments, the third layer 2105 may be coupled to either the first or second layer using the same techniques as used to couple the first layer 315 to the second layer 320.

In some embodiments, one or more of the fluid pathways may comprise a valve (not shown). For example, the valve in the negative-pressure pathway (e.g. first pathway 340) may comprise or consist essentially of a one-way valve, such as a flap valve or duck-bill valve, which may be configured to prevent reflux of fluid from the pathway to the tissue site. The pressure-sensing pathway (e.g. second pathway 345) may comprise a valve or fluid restriction, for example configured to minimize fluid entering the pressure-sensing pathway while allowing pressure communication. In some embodiments, a one-way valve in the instillation pathway (e.g. additional pathway 2120) may be configured to allow fluid flow from the pathway outward to the wound, while restricting fluid flow into the pathway. In some embodiments, the instillation pathway may be configured so that at least a portion of it is collapsible under negative pressure, and that configuration could essentially function as the valve.

Figure 22:
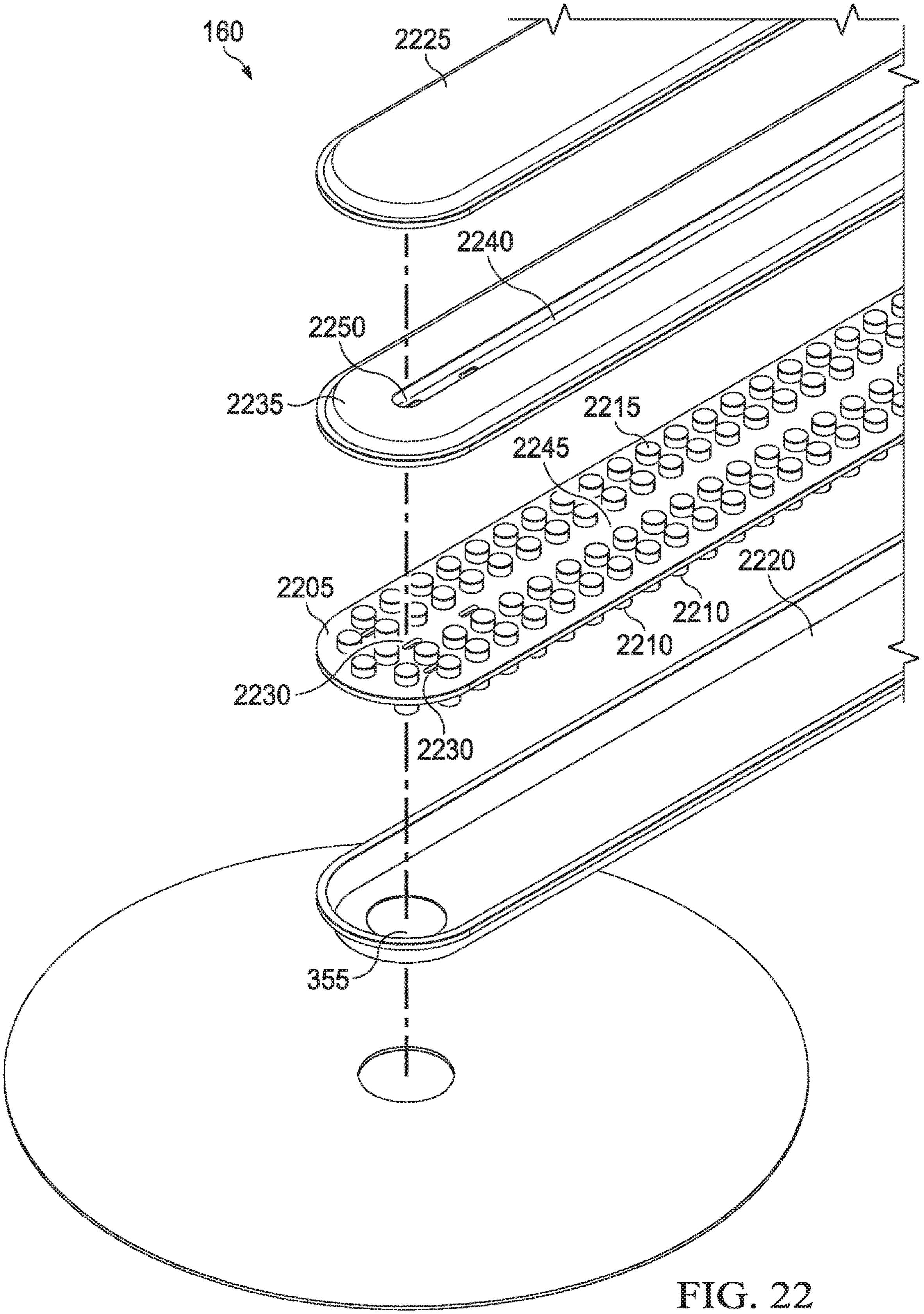
FIG. 22 is an assembly view of yet another bridge embodiment.

FIG. 22 is an assembly view of yet another exemplary bridge 160, illustrating additional details that may be associated with some embodiments. In some embodiments, a double-sided spacer layer 2205 may have a plurality of supports extending from each of two opposing surfaces (e.g. a top surface and a bottom surface). For example, the double-sided spacer layer 2205 may have a first plurality of spacer supports 2210 extending from the bottom surface, and a second plurality of spacer supports 2215 extending from the top surface. In some embodiments, the double-sided spacer layer 2205 may comprise or consist essentially of foam, such as closed-cell foam. In some embodiments, the double-sided spacer layer 2205 may be located between and coupled to at least two outer layers (e.g. a lower layer 2220 and an upper layer 2225), which may form at least a first fluid pathway between the lower layer 2220 and the bottom surface of the double-sided spacer layer 2205, and a second fluid pathway between the upper layer 2225 and the top surface of the double-sided spacer layer 2205. In some embodiments, the outer layers may comprise or consist essentially of film. In some embodiments, when the double-sided spacer layer 2205 is formed of closed-cell foam and is welded around the perimeter to both the outer layers, the first fluid pathway and the second fluid pathway may be stacked atop each other and may be pneumatically isolated except at the distal end. For example, the closed-cell foam double-sided spacer layer 2205 may prevent fluid transport between the two stacked fluid pathways, with the first fluid pathway disposed beneath the double-sided spacer layer 2205 (e.g. between the double-sided spacer layer 2205 and the lower layer 2220), and the second fluid pathway disposed above the double-sided spacer layer 2205 (e.g. between the double-sided spacer layer 2205 and the upper layer 2225). In some embodiments, the aperture 355 may be formed in the distal end of the first fluid pathway (e.g. in the lower layer 2220), and one or more spacer layer openings 2230 may provide fluid communication between the aperture 355 and the second fluid pathway. In some embodiments, the first fluid pathway may form the negative-pressure pathway (e.g. fluidly coupled to the negative-pressure source at the proximal end), and the second fluid pathway may form either the instillation pathway (e.g. fluidly coupled to the instillation fluid source at the proximal end) or the pressure-sensing pathway (e.g. fluidly coupled to the pressure sensor at the proximal end).

Some embodiments may also be configured to comprise a third fluid pathway. For example, FIG. 22 may comprise a separator layer 2235 stacked between and/or coupled to the top surface of the double-sided spacer layer 2205 and the upper layer 2225. In some embodiments, the separator layer 2235 may comprise a channel 2240, for example extending out from the top surface of the separator layer 2235 or formed as an elongate indentation in the separator layer 2235 (e.g. extending down from the bottom surface of the separator layer 2235). In some embodiments, the channel 2240 may comprise a barrier, which may be formed by welds and/or may extend around the channel perimeter to form the walls of the channel 2240 (e.g. which may be spaced apart and/or substantially parallel until the closed distal end). In some embodiments, the channel 2240 may be enclosed on the top by interaction (e.g. coupling) of the channel walls with the upper layer 2225. While the upper layer 2225 in FIG. 22 may be coextensive with the separator layer 2235, the lower layer 2220, and/or the double-sided spacer layer 2205, in some embodiments the upper layer may only span and couple to the channel walls. In some embodiments, the second plurality of spacer supports 2215 may be configured to form a gap 2245, and the channel 2240 may be configured to interact with the gap 2245. For example, the channel 2240 may be disposed within the gap 2245. In some embodiments, the instillation pathway may be formed within the channel 2240 and/or between the separator layer 2235 and the upper layer 2225, and/or may comprise one or more instillation openings 2250 in its distal end. In some embodiments, the pressure-sensing pathway may be formed between the top surface of the double-sided spacer layer 2205 and the separator layer 2235 (e.g. around the exterior of the channel). The instillation pathway within the channel 2240 may be pneumatically isolated from the surrounding pressure-sensing pathway and the negative-pressure pathway, except at the distal end (e.g. through the aperture). In some embodiments, the spacer layer openings 2230 may comprise one or more first spacer layer openings configured to provide fluid communication between the channel (e.g. when aligned with the instillation openings) and the aperture 355, and the spacer layer openings 2230 may also comprise one or more second spacer layer openings configured to provide fluid communication between the pressure-sensing pathway and the aperture 355.

In some embodiments, the separator layer may be formed by providing a film sheet, forming one or more instillation apertures in the film sheet, and forming (e.g. by welds) two longitudinal channel walls or barriers (which may be substantially parallel) on an outer surface of the film. In some embodiments, forming the separator layer may comprise providing a film sheet, forming the one or more instillation apertures in the film sheet, and forming an elongate indentation in the sheet which may extend from the proximal end to the instillation apertures in the distal end. The channel may then be formed as an enclosed fluid pathway when the separator layer is sandwiched between an outer layer and the double-sided spacer layer. In some embodiments, the walls of the channel may be disposed on the film so that the channel interacts with the gap, such that the channel in the assembled bridge may be located between the second plurality of spacer supports.

The systems, apparatuses, and methods described herein may provide significant advantages. For example, some embodiments may maintain separate instillation and negative-pressure treatment pathways. Some embodiments may have a low-profile and/or be conformable, for improved comfort if positioned under a patient for example. Some embodiments may be configured to minimize stiff edges, for example by minimizing or eliminating welded edges. Some embodiments may be configured to prevent occlusion, maintaining an open pathway for negative-pressure treatment and/or instillation fluid delivery so that the negative pressure and/or instillation fluid may be provided even when the device is under compressive load (for example, if the patient is lying atop the device). Some embodiments may improve access to certain wound sites. Some embodiments may be configured to minimize unintended siphoning of instillation fluid during negative-pressure treatment. The configuration of some embodiments may reduce contamination of instillation fluid, for example by preventing exudate from flowing into the instillation system. Some embodiments may allow wound pressure monitoring, which may for example reduce the risk of pressure drop between the pad and the wound. Some embodiments may be configured to simplify accurate placement and/or to indicate negative pressure and/or instillation fluid flow therethrough. Some embodiments may employ a single bridge which contains the negative-pressure pathway, the instillation pathway, and/or one or more pressure-sensing pathways, which may simplify instillation and use. Some embodiments may be configured to prevent excessive skin moisture buildup. Some embodiments may be configured to improve construction and/or minimize cost, for example allowing for high volume, low cost production.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 110, the container 115, or both may be eliminated or separated from other components for manufacture or sale. In other example configurations, the bridge 160 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for managing fluid at a tissue site, comprising:

a first layer comprising an outer surface, an inner surface, and a first plurality of supports extending from the inner surface, wherein the first layer is formed of foam;

a second layer in stacked relationship with the first layer and oriented to be adjacent to the first plurality of supports, wherein the first layer and the second layer define at least one fluid pathway therebetween;

a first barrier between the inner surface of the first layer and an inner surface of the second layer, wherein the at least one fluid pathway comprises a first fluid pathway and a second fluid pathway formed by the first barrier;

an aperture configured to provide fluid communication between the at least one fluid pathway and the tissue site;

a port configured to provide fluid communication between the at least one fluid pathway and a negative-pressure source:

the first fluid pathway is configured to be in fluid communication with a negative-pressure source through the port;

the second fluid pathway being configured to be in fluid communication with an instillation source or a pressure sensor through the port; and the first fluid pathway and the second fluid pathway are pneumatically isolated except through a recessed space configured to provide fluid communication between the aperture, the first fluid pathway, and the second fluid pathway.

2. The apparatus of claim 1, further comprising a second barrier between the inner surface of the first layer and the inner surface of the second layer, wherein:

the at least one fluid pathway further comprises a third fluid pathway formed by the second barrier;

the third fluid pathway is pneumatically isolated except through the recessed space; and the third fluid pathway is configured to be in fluid communication with a pressure sensor through the port.

3. The apparatus of claim 1, wherein the first plurality of supports are configured to support the first fluid pathway to resist collapse under negative pressure.

4. The apparatus of claim 1, wherein the first plurality of supports are coupled to the second layer.

5. The apparatus of claim 1, further comprising an affixation surface located on the outer surface around the aperture.

6. The apparatus of claim 1, wherein the first layer further comprises a slot between and separating the first fluid pathway and the second fluid pathway.

7. The apparatus of claim 1, further comprising a third layer in stacked relationship with the first layer and the second layer in order to form an additional fluid pathway extending between the port and the recessed space, wherein the additional fluid pathway is pneumatically isolated except at the recessed space.

8. The apparatus of claim 7, wherein the third layer comprises or consists essentially of a film.

9. The apparatus of claim 7, wherein the third layer comprises or consists essentially of closed-cell foam.

10. The apparatus of claim 1, wherein the at least one fluid pathway is coated with an anticoagulant agent.

11. The apparatus of claim 1, wherein the at least one fluid pathway is coated with a hydrophobic surface treatment.

12. The apparatus of claim 1, wherein one or more of the at least one fluid pathway comprises a valve.

13. The apparatus of claim 1, further comprising a bulb element configured to collapse to be substantially flat with the outer surface when experiencing negative pressure, and to project outward in the absence of negative pressure.

14. A system for managing fluid at a tissue site, comprising:

a negative-pressure source; and a bridge fluidly coupled to the negative-pressure source, comprising:

a spacer layer comprising an outer surface, an inner surface, and a plurality of supports extending from the inner surface, wherein the spacer layer is formed of foam;

a cover layer in stacked relationship with the spacer layer and oriented to be adjacent to the plurality of supports, wherein the spacer layer and the cover layer define at least one fluid pathway therebetween;

an aperture configured to provide fluid communication between the at least one fluid pathway and the tissue site; and a port configured to provide fluid communication between the at least one fluid pathway and the negative-pressure source.

15. The system of claim 14, further comprising an instillation source, wherein the at least one fluid pathway comprises a negative-pressure pathway in fluid communication with the negative-pressure source and an instillation pathway in fluid communication with the instillation source.

16. The system of claim 14, further comprising a pressure sensor, wherein the at least one fluid pathway comprises a negative-pressure pathway in fluid communication with the negative-pressure source and a sensing pathway in fluid communication with the pressure sensor.

17. The apparatus of claim 1, wherein the first plurality of supports are substantially perpendicular to the inner surface of the first layer.

18. The apparatus of claim 1, wherein the first plurality of supports extend inward from the inner surface of the first layer.

19. The apparatus of claim 1, wherein the first plurality of supports comprise a plurality of standoffs.

* * * * *